US012692558B2

(12) United States Patent
Abate et al.

(10) Patent No.: US 12,692,558 B2
(45) Date of Patent: Jul. 28, 2026

(54) POINT OF CARE AND IMPROVED DETECTION AND QUANTIFICATION OF BIOMOLECULES

(71) Applicants: THE REGENTS OF THE UNIVERSITY OF CALIFORNIA, Oakland, CA (US); CZ BIOHUB SF, LLC, San Francisco, CA (US)

(72) Inventors: Adam Abate, Oakland, CA (US); Harish Vasudevan, Oakland, CA (US); Peng Xu, Oakland, CA (US); Krzysztof Langer, Oakland, CA (US); Xiangpeng Li, Oakland, CA (US); Leqian Liu, Oakland, CA (US); Chen Sun, Oakland, CA (US); Daniel Weisgerber, Oakland, CA (US)

(73) Assignees: THE REGENTS OF THE UNIVERSITY OF CALIFORNIA, Oakland, CA (US); CZ BIOHUB SF, LLC, San Francisco, CA (US)

( * ) Notice: Subject to any disclaimer, the term of this patent is extended or adjusted under 35 U.S.C. 154(b) by 631 days.

(21) Appl. No.: 18/022,938

(22) PCT Filed: Aug. 27, 2021

(86) PCT No.: PCT/US2021/047948
§ 371 (c)(1),
(2) Date: Feb. 23, 2023

(87) PCT Pub. No.: WO2022/047154
PCT Pub. Date: Mar. 3, 2022

(65) Prior Publication Data
US 2023/0313321 A1      Oct. 5, 2023

Related U.S. Application Data

(60) Provisional application No. 63/135,920, filed on Jan. 11, 2021, provisional application No. 63/127,642, filed on Dec. 18, 2020, provisional application No. 63/071,900, filed on Aug. 28, 2020.

(51) Int. Cl.
*C12Q 1/68* (2018.01)
*C12Q 1/6888* (2018.01)
*C12Q 1/70* (2006.01)

(52) U.S. Cl.
CPC ............. *C12Q 1/70* (2013.01); *C12Q 1/6888* (2013.01)

(58) Field of Classification Search
None
See application file for complete search history.

(56) References Cited

U.S. PATENT DOCUMENTS

2006/0024721 A1    2/2006  Pedersen
2019/0218594 A1    7/2019  Abate et al.

FOREIGN PATENT DOCUMENTS

WO    WO-2010036352 A1 *  4/2010  ......... G01N 15/1459

OTHER PUBLICATIONS

Yen et al. (J. Am. Chem. Soc. 2019, 141, 1515-1525, including supplemental materials) (Year: 2019).*
ImageJ Documentation Wiki, Liquid Droplet Counter, 2019. Obtained from https://imagejdocu.list.lu/plugin/analysis/droplet_counter/start#:~:text=Start ImageJ%2C open your image, will output a measurement table On Oct. 24, 2025. 3 pages (Year: 2019).*
Al et al., Correlation of Chest CT and RT-PCR Testing for Coronavirus Disease 2019 (COVID-19) in China: A Report of 1014 Cases, Radiology, 296(2):E32-E40 (2020).
Alteri et al., Detection and quantification of SARS-CoV-2 by droplet digital PCR in real-time PCR negative nasopharyngeal swabs from suspected COVID-19 patients, Plos One, 15(9):e0236311 (2020).
Baker, Digital PCR hits its stride, Nat. Methods, 9(6):541-544 (2012).
Basu, Digital Assays Part I: Partitioning Statistics and Digital PCR, Slas. Technol., 22(4):369-386 (2017).
Broughton et al., CRISPR-Cas12-based detection of SARS-CoV-2, Nat. Biotechnol., 38(7):870-874 (2020).
Byrnes et al., Simple Polydisperse Droplet Emulsion Polymerase Chain Reaction with Statistical Volumetric Correction Compared with Microfluidic Droplet Digital Polymerase Chain Reaction, Anal. Chem., 90(15):9374-9380 (2018).
Chang et al., Single molecule enzyme-linked immunosorbent assays: theoretical considerations, J. Immuno. Methods., 378(1-2):102-15 (2012).
Chantrapomchai et al., Food Res. Int., 34(9):827-835 (2001).
Collier et al., Point of Care Nucleic Acid Testing for SARS-CoV-2 in Hospitalized Patients: A Clinical Validation Trial and Implementation Study, Cell Rep. Med., 1(5):1-7e3 (2020).
Deiana et al., Assessment of the direct quantitation of SARS-COV-2 by droplet digital PCR, Sci. Rep., 10(1):18764 (2020).
Dejoumette et al., Creating biocompatible oil-water interfaces without synthesis: direct interactions between primary amines and carboxylated perfluorocarbon surfactants, Anal. Chem., 85(21):10556-10564 (2013).
Dingle et al., Tolerance of droplet-digital PCR vs real-time quantitative PCR to inhibitory substances, Clin. Chem., 59(11):1670-1672 (2013).

(Continued)

*Primary Examiner* — Juliet C Switzer
(74) *Attorney, Agent, or Firm* — MARSHALL, GERSTEIN & BORUN LLP

(57) ABSTRACT

The present disclosure provides materials and methods for detecting the presence of a target, such as a nucleic acid, biomolecule or biological particle, or virus genome in a sample. The present disclosure further provides point of care detection methods that cane done quickly and simply, optionally without sophisticated instrumentation. The present disclosure further provides improved methods for detecting and quantifying detection signals from various emulsions.

12 Claims, 25 Drawing Sheets

Specification includes a Sequence Listing.

(56)            References Cited

OTHER PUBLICATIONS

Dobnik et al., Multiplex quantification of four DNA targets in one reaction with Bio-Rad droplet digital PCR system for GMO detection, Sci. Rep., 6:35451 (2016).

Gaikwad et al., Ultrasound emulsification: effect of ultrasonic and physicochemical properties on dispersed phase volume and droplet size, Ultrason Sonochem., 15(4):554-563 (2008).

Gandhi et al., Asymptomatic Transmission, the Achilles' Heel of Current Strategies to Control Covid-19, N. Engl. J. Med., 382(22):2158-2160 (2020).

Guo et al., Droplet microfluidics for high-throughput biological assays, Lab. Chip., 12(12):2146-2155 (2012).

Han et al., Application of digital PCR for assessing DNA fragmentation in cytotoxicity response, Biochim. Biophys. Acta, Gen. Subj., 1863(8):1235-1242 (2019).

Hatch et al., 1-Million droplet array with wide-field fluorescence imaging for digital PCR, Lab. Chip., 11(22):3838-3845 (2011).

Hatori et al., Particle-Templated Emulsification for Microfluidics-Free Digital Biology, Anal. Chem., 90(16):9813-9820 (2018).

Hayden et al., Comparison of droplet digital PCR to real-time PCR for quantitative detection of cytomegalovirus, J. Clin. Microbiol., 51(2):540-546 (2013).

Heid et al., Real time quantitative PCR, Genome Res., 6(10):986-994 (1996).

Heyries et al., Megapixel digital PCR, Nat. Methods, 8(8):649-51 (2011).

Hindson et al., Absolute quantification by droplet digital PCR versus analog real-time PCR, Nat. Methods, 10:1003-1005 (2013).

Holtze et al., Biocompatible surfactants for water-in-fluorocarbon emulsions, Lab. Chip., 8(10):1632-1639 (2008).

Hu et al., Absolute Quantification of H5-Subtype Avian Influenza Viruses Using Droplet Digital Loop-Mediated Isothermal Amplification, Anal. Chem., 89:745-750 (2017).

International Application No. PCT /US2021/047948, Invitation to Pay Additional Fees, mailed Dec. 9, 2021.

International Application No. PCT/US2021/047948, International Preliminary Report on Patentability, mailed Mar. 9, 2023.

International Application No. PCT/US2021/047948, International Search Report and Written Opinion, mailed Feb. 28, 2022.

Joung et al., Point-of-care testing for COVID-19 using SHERLOCK diagnostics, medRxiv, (2020).

Kellner et al., SHERLOCK: nucleic acid detection with CRISPR nucleases, Nat. Protoc., 14(10):2986-3012 (2019).

Kreutz et al., Theoretical design and analysis of multivolume digital assays with wide dynamic range validated experimentally with microfluidic digital PCR, Anal. Chem., 83(21):8159-8168 (2011).

Kucirka et al., Variation in False-Negative Rate of Reverse Transcriptase Polymerase Chain Reaction-Based SARS-CoV-2 Tests by Time Since Exposure, Ann. Intern. Med., 173(4):262-267 (2020).

Kuypers et al., Applications of digital PCR for clinical microbiology, Journal of Clinical Microbiology, 55(6):1621-1628 (2017).

Ladha et al., A 5-min RNA preparation method for COVID-19 detection with RT-qPCR, medRxiv, (2020).

Lamb et al., Rapid Detection of Novel Coronavirus (COVID-19) by Reverse Transcription-Loop-Mediated Isothermal Amplification, medRxiv, (2020).

Lance et al., Peering below the diffraction limit: robust and specific sorting of viruses with flow cytometry, Virol. J., 13:201 (2016).

Li et al., Stability issues of RT-PCR testing of SARS-CoV-2 for hospitalized patients clinically diagnosed with COVID-19, J. Med. Virol., 92(7):903-908 (2020).

Liao et al., Three-dimensional digital PCR through light-sheet imaging of optically cleared emulsion, Proc. Natl. Acad. Sci. U.S.A., 117(41):25628-25633 (2020).

Mackay et al., Real-time PCR in virology, Nucleic Acids Research, 30(6):1292-305 (2002).

Morinishi et al., Simple Bulk Readout of Digital Nucleic Acid Quantification Assays, J. Vis. Exp., (103):52925 (2015).

Nakayama et al., Pitfalls of DNA Quantification Using DNA-Binding Fluorescent Dyes and Suggested Solutions, Plos One, 11(3):e0150528 (2016).

Pan et al., Viral load of SARS-CoV-2 in clinical samples, Lancet Infect. Dis., 20(4):411-412 (2020).

Pavsic et al., Digital PCR for direct quantification of viruses without DNA extraction, Anal. Bioanal. Chem., 408(1):67-75 (2016).

Pohl et al., Principle and applications of digital PCR, Expert. Rev. Mol. Diagn., 4(1):41-47 (2004).

Quan et al., dPCR: A Technology Review, Sensors, 18(4):1271 (2018).

Sedlak et al., Clinical utility of droplet digital PCR for human cytomegalovirus, J. Clin. Microbiol., 52(8):2844-8 (2014).

Sedlak et al., Identification of chromosomally integrated human herpesvirus 6 by droplet digital PCR, Clin. Chem., 60(5):765-772 (2014).

Shen et al., Multiplexed quantification of nucleic acids with large dynamic range using multivolume digital RT-PCR on a rotational SlipChip tested with HIV and hepatitis C viral load, J. Am. Chem. Soc., 133(44):17705-17712 (2011).

Strain et al., Highly precise measurement of HIV DNA by droplet digital Pcr, PLoS One, 8(4):e55943 (2013).

Sun et al., Accurate bulk quantitation of droplet digital PCR, (2021), Retrieved from the Internet: URL:https://www.biorxiv.org/content/10.1101/2021.01.13.424628v1.

Suo et al., ddPCR: a more accurate tool for SARS-CoV-2 detection in low viral load specimens, Emerg. Microbes Infect., 9(1):1259-1268 (2020).

* cited by examiner

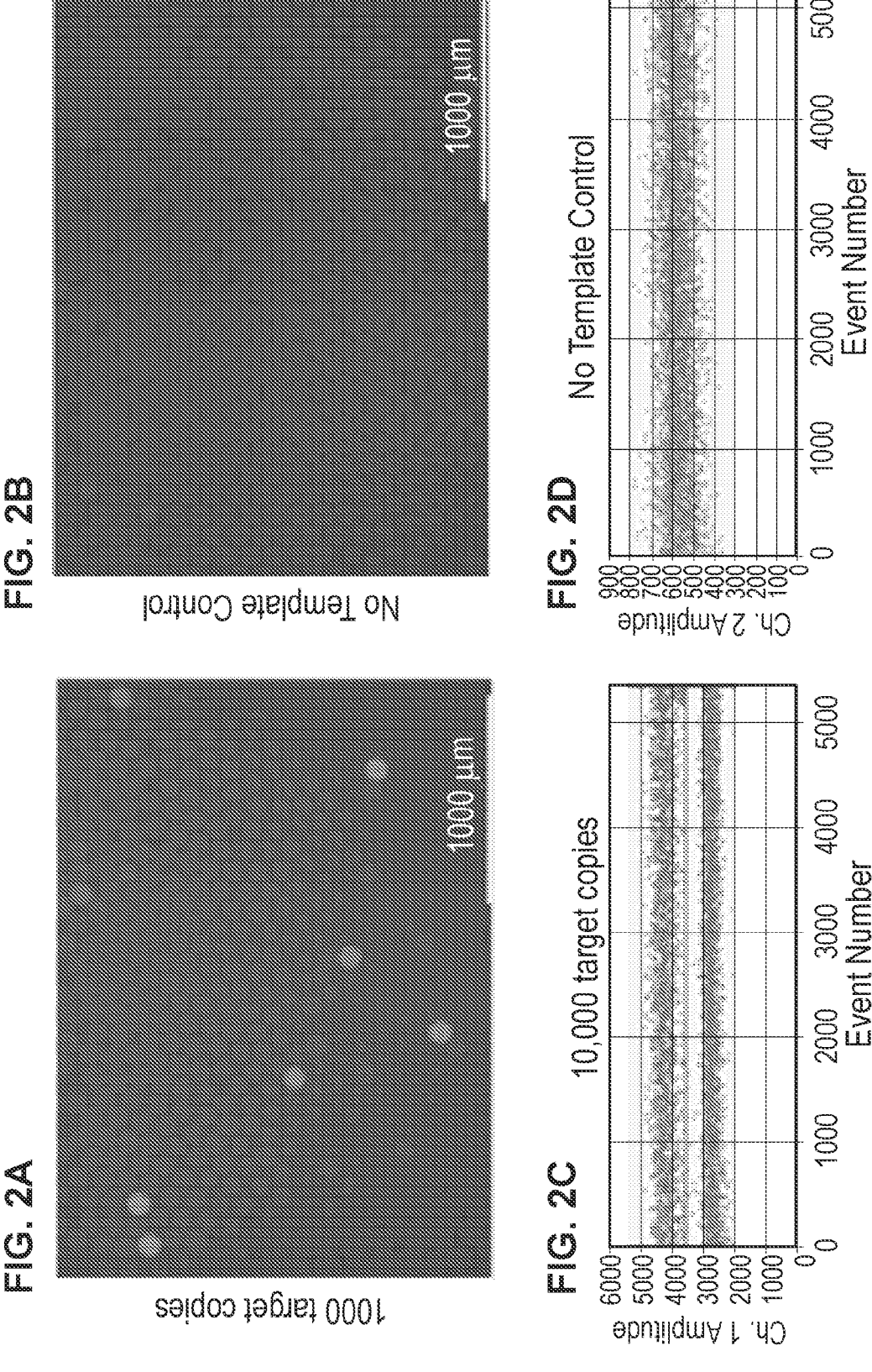

Figures 4A, 4B:
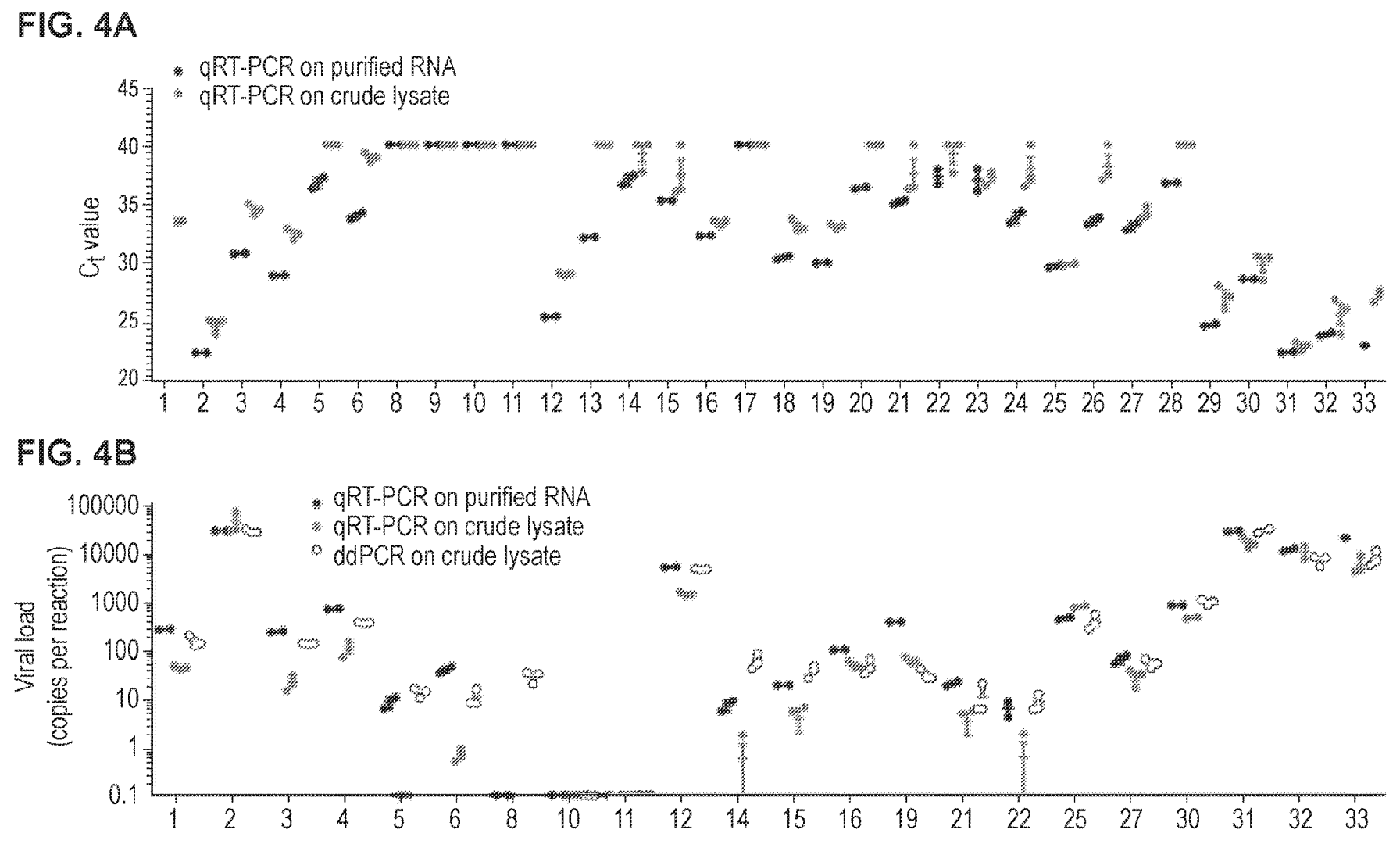

FIG. 4A qRT-PCR on purified RNA
qRT-PCR on crude lysate

Ct value

FIG. 4B qRT-PCR on purified RNA
qRT-PCR on crude lysate
ddPCR on crude lysate

Viral load
(copies per reaction)

FIG. 8

Simulation Result
(1 cm^2 scanning area, 120 um and 50 um sized droplets, and 20% precision)

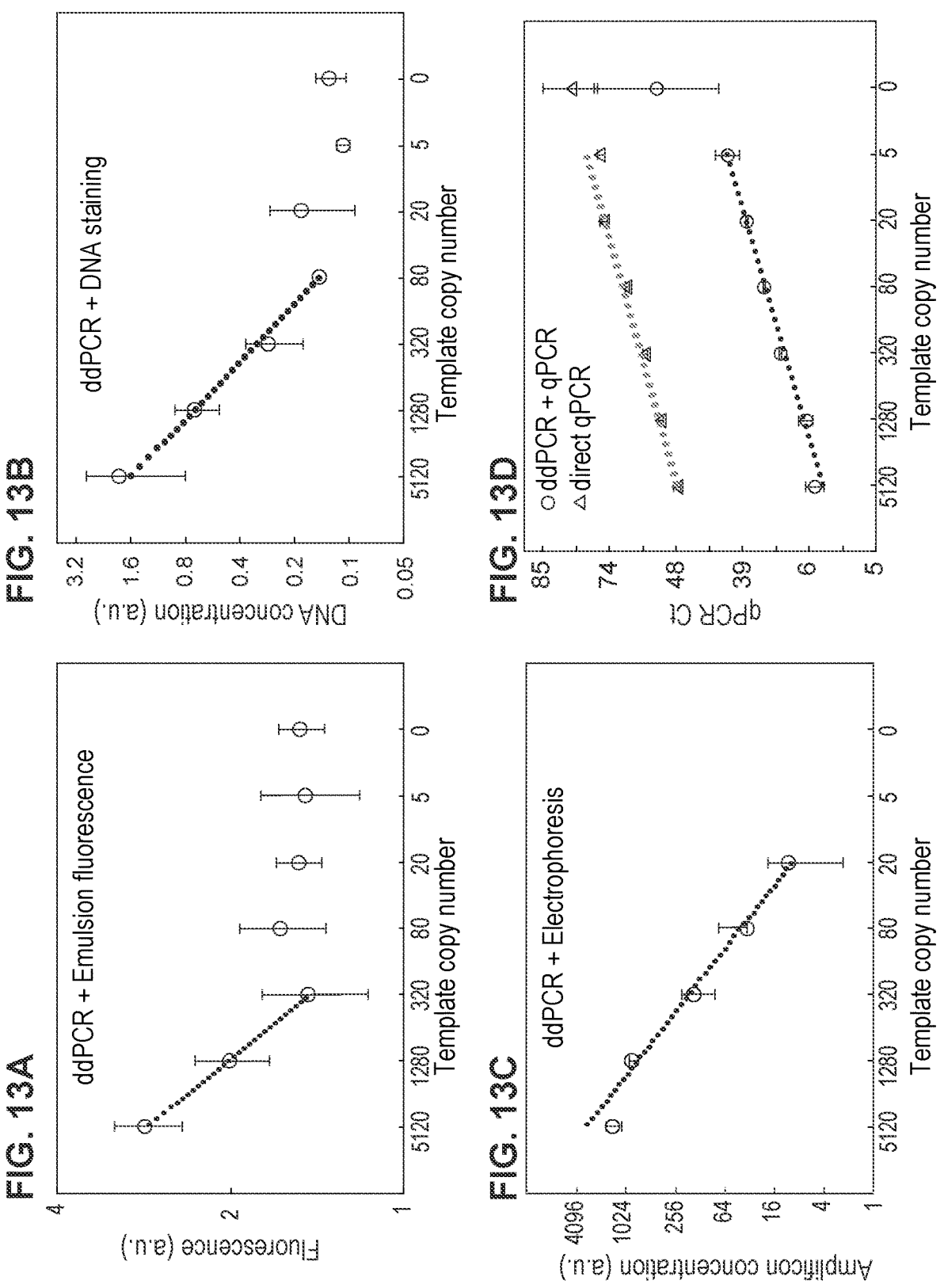
FIG. 13A ddPCR + Emulsion fluorescence
FIG. 13B ddPCR + DNA staining
FIG. 13C ddPCR + Electrophoresis
FIG. 13D ddPCR + qPCR
○ ddPCR
△ direct qPCR

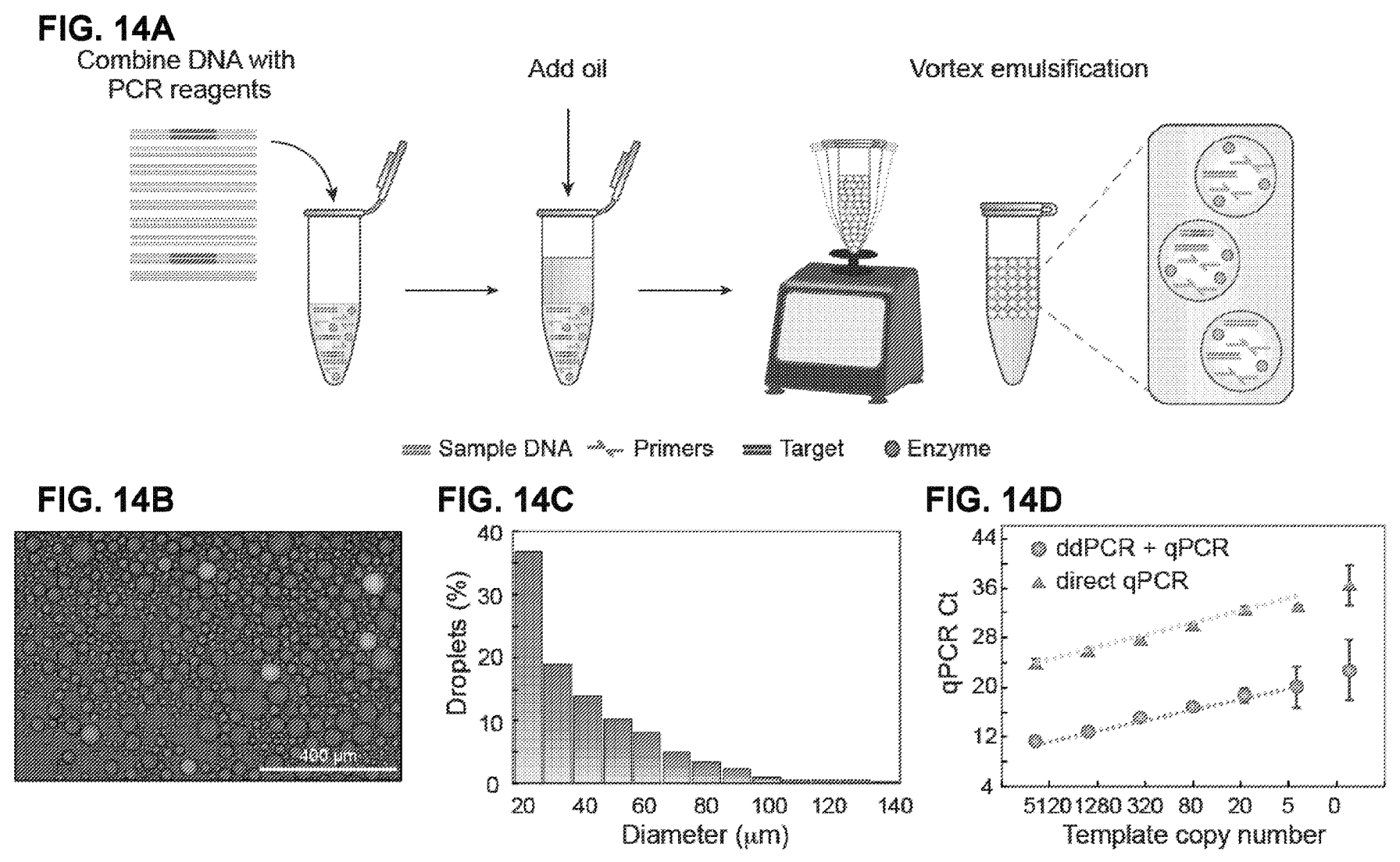

FIG. 14A Combine DNA with PCR reagents

Add oil

Vortex emulsification

==== Sample DNA  ~~~ Primers  === Target  ● Enzyme

Droplets (%)

Diameter (μm)

FIG. 14D

● ddPCR + qPCR
▲ direct qPCR qPCR Cq

Template copy number

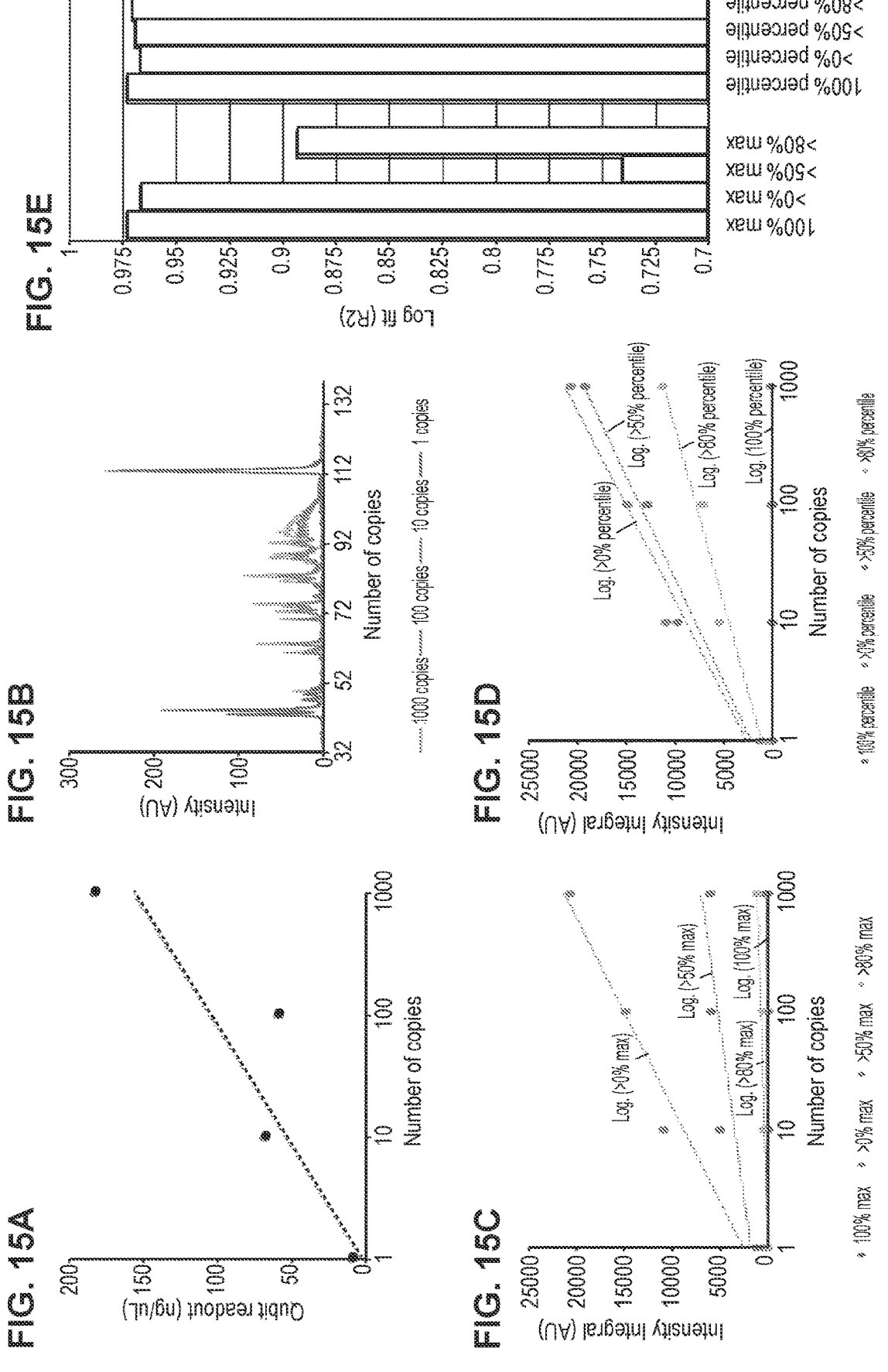

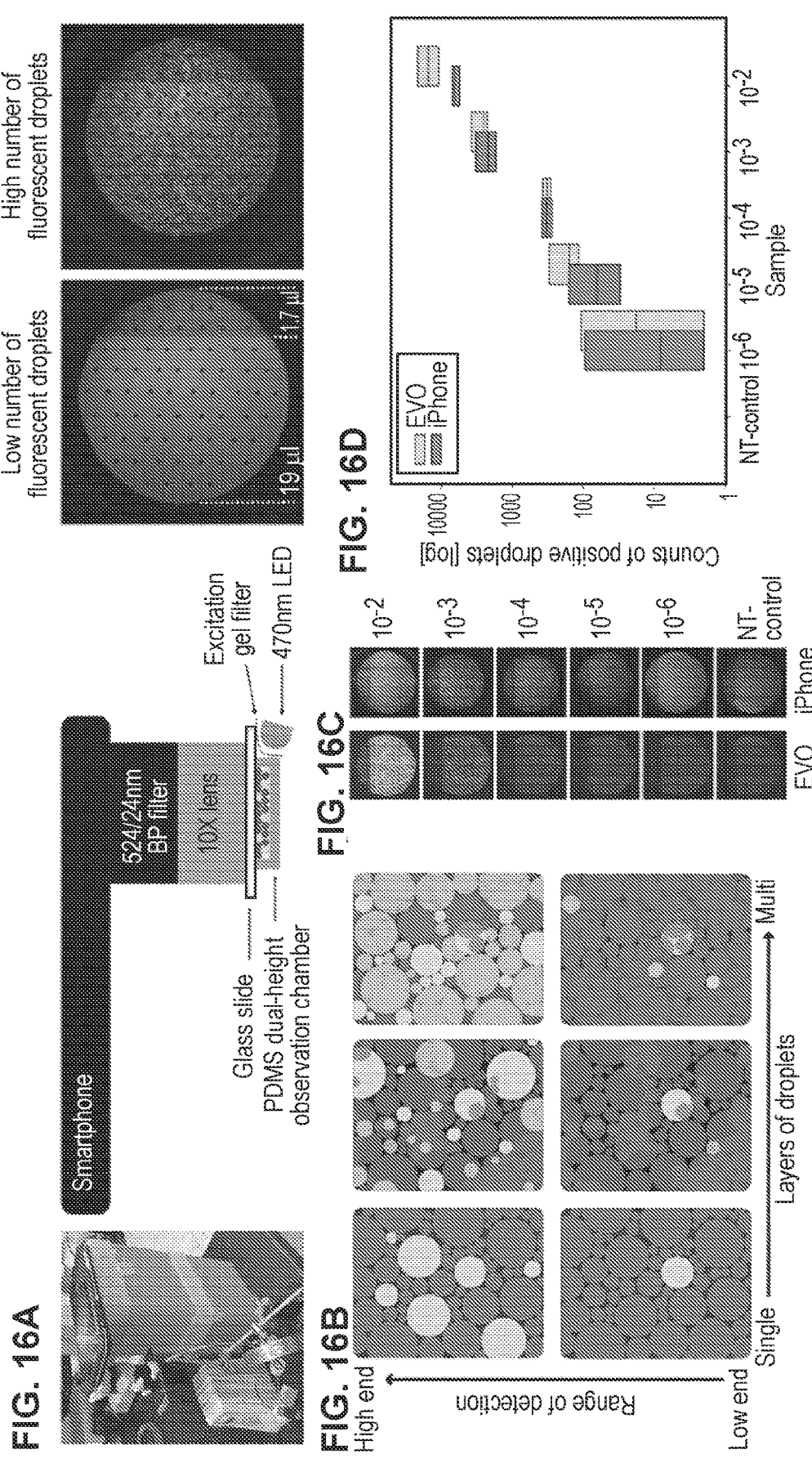

Hydrated Particle

Freeze-dry

Enlarged pores

Rehydrate by reaction reagents

Emulsify

Engulf reagents in pores

Sonication to improve sample quality and readability

Reaction

Initial sample

Sonic action

Sample with improved quality and readability

1

POINT OF CARE AND IMPROVED DETECTION AND QUANTIFICATION OF BIOMOLECULES

CROSS-REFERENCE TO RELATED APPLICATIONS

The present application is a U.S. National Phase of International Patent Application No. PCT/US21/47948 filed Aug. 27, 2021, which claims priority to U.S. Provisional Patent Application Nos. 63/071,900, 63/127,642, and 63/135,920 filed on Aug. 28, 2020, Dec. 18, 2020, and Jan. 11, 2021, respectively, their entirety of which are incorporated by reference herein.

STATEMENT REGARDING FEDERALLY SPONSORED RESEARCH

The invention was made with Government support under Grant Nos. AI129206, R01-EB019453-01 and R01-HG008978-01 awarded by The National Institutes of Health. The government has certain rights in the invention.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "55870PC_Seqlisting.txt", which was created on Aug. 16, 2021 and is 729 bytes in size. The subject matter of the Sequence Listing is incorporated herein in its entirety by reference.

FIELD

The present disclosure relates generally to methods for detecting biomolecules and biological particles, including nucleic acids.

BACKGROUND

Fast and simple detection of pathogens is critical for clinical purposes and population surveillance. Several methods are available to specifically detect nucleic acid, protein, or other molecules. However, sensitive detection assays typically require trained experts, sophisticated instruments, and/or need extended assay time for results. While point-of-care detection methods are easy and quick to perform, they often lack the sensitivity or selectivity required for clinic application.

Detection and quantification of DNA often relies on amplification from starting material, which is most commonly accomplished with polymerase chain reaction (PCR). PCR broadly enables many fundamental tasks in both basic research and clinical medicine including genotyping model organisms, high throughput sequencing, cancer diagnosis, and detection of microbial pathogens. Technically, PCR operates by sequentially doubling the amount of input DNA through multiple successive amplification cycles. Quantitative PCR (qPCR) builds on this technique by measuring amplification in real time and determining a threshold cycle number from which relative input DNA amount can be calculated. While the limit of detection of PCR is theoretically 1 input DNA copy, the high number of PCR cycles required to amplify low input DNA amounts reduces the sensitivity of such results.

Furthermore, the quantitative resolution, defined as the noise associated with the measurement of a given input DNA concentration, greatly increases at low DNA copy numbers due to many factors including non-specific amplification and stochastic effects of PCR inhibitors. Thus, detection and quantification from low amounts of starting DNA is not optimal with conventional PCR.

Diagnosis of COVID-19 caused by the SARS-CoV-2 virus has been met with difficulties due to the novel causative pathogen, lack of a complete understanding of the clinical sequelae, limited availability of testing resources, and variability in viral load across and within patients.

SUMMARY OF THE INVENTION

One embodiment of the present disclosure provides a method of detecting a target nucleic acid in a sample comprising: a. combining in a vessel (i) a sample comprising a target nucleic acid; (ii) a solution comprising reagents for amplifying and detecting the target nucleic acid; and (iii) an immiscible carrier; b. agitating the combined solution of (a) under conditions that allow encapsulation of the target nucleic acid with the reagents for amplifying and detecting the target nucleic acid in droplets, thereby forming a polydispersed emulsion; c. incubating the solution of step (b) under conditions that allow amplification of the target nucleic acid in the droplets; and d. detecting the presence of the target nucleic acid in the emulsion; wherein said detecting comprises simultaneously quantifying detection signals from multiple layers and from multiple individual droplet contents.

In another embodiment, a method of detecting a target nucleic acid in a sample is provided comprising: a. combining in a vessel (i) a sample comprising a target nucleic acid; (ii) a solution comprising reagents for amplifying and detecting the target nucleic acid; and (iii) an immiscible carrier; b. agitating the combined solution of (a) under conditions that allow encapsulation of the target nucleic acid with the reagents for amplifying and detecting the target nucleic acid in droplets, thereby forming a polydispersed emulsion; c. incubating the solution of step (b) under conditions that allow amplification of the target nucleic acid in the droplets; and d. merging the droplets and detecting the presence of the target nucleic in the emulsion; wherein said detecting comprises quantifying a bulk detection signal from the merged droplets.

In still another embodiment, a method of detecting a target nucleic acid in a sample is provided comprising: a. combining in a vessel (i) a sample comprising a target nucleic acid; (ii) a solution comprising reagents for amplifying and detecting the target nucleic acid; (iii) a collection of particles; and (iv) an immiscible carrier; b. agitating the combined solution of (a) under conditions that allow encapsulation of the target nucleic acid with the reagents for amplifying and detecting the target nucleic acid in droplets, thereby forming a monodispersed emulsion; c. incubating the solution of step (b) under conditions that allow amplification of the target nucleic acid in the droplets; and d. detecting the presence of the target nucleic acid in the emulsion; wherein said detecting comprises simultaneously quantifying detection signals from multiple layers and from multiple individual droplet contents.

In yet another embodiment, a method of detecting a target nucleic acid in a sample is provided comprising: a. combining in a vessel (i) a sample comprising a target nucleic acid; (ii) a solution comprising reagents for amplifying and detecting the target nucleic acid; (iii) a collection of particles; and (iv) an immiscible carrier; b. agitating the combined solution of (a) under conditions that allow encapsulation of the target nucleic acid with the reagents for amplifying and detecting the target nucleic acid in droplets, thereby forming a monodispersed emulsion; c. incubating the solution of step (b) under conditions that allow amplification of the target nucleic acid in the droplets; and d. merging the droplets and detecting the presence of the target nucleic in the emulsion; wherein said detecting comprises quantifying a bulk detection signal from the merged droplets.

In another embodiment the present disclosure provides a method of detecting a target biomolecule or biological particle in a sample comprising: a. combining in a vessel (i) a sample comprising a biomolecule or biological particle; (ii) a solution comprising reagents for detecting the biomolecule or biological particle; and (iii) an immiscible carrier; b. agitating the combined solution of (a) under conditions that allow encapsulation of the target biomolecule or biological particle with the reagents for detecting the target biomolecule or biological particle in droplets, thereby forming a polydispersed emulsion; c. incubating the solution of step (b) under conditions that allow detection of the target biomolecule or biological particle in the droplets; and d. detecting the presence of the biomolecule or biological particle in the emulsion; wherein said detecting comprises simultaneously quantifying detection signals from multiple layers and from multiple individual droplet contents.

In still another embodiment the present disclosure provides a method of detecting a target biomolecule or biological particle in a sample comprising: a. combining in a vessel (i) a sample comprising a target biomolecule or biological particle; (ii) a solution comprising reagents for detecting the target biomolecule or biological particle; and (iii) an immiscible carrier; b. agitating the combined solution of (a) under conditions that allow encapsulation of the target biomolecule or biological particle with the reagents for detecting the target biomolecule or biological particle in droplets, thereby forming a polydispersed emulsion; c. incubating the solution of step (b) under conditions that allow amplification of the target biomolecule or biological particle in the droplets; and d. merging the droplets and detecting the presence of the biomolecule or biological particle in the emulsion; wherein said detecting comprises quantifying a bulk detection signal from the merged droplets.

In another embodiment, a method of detecting a target biomolecule or biological particle in a sample is provided comprising: a. combining in a vessel (i) a sample comprising a target biomolecule or biological particle; (ii) a solution comprising reagents for detecting the target nucleic acid; (iii) a collection of particles; and (iv) an immiscible carrier; b. agitating the combined solution of (a) under conditions that allow encapsulation of the target biomolecule or biological particle with the reagents for detecting the target biomolecule or biological particle in droplets, thereby forming a monodispersed emulsion; c. incubating the solution of step (b) under conditions that allow detection of the target biomolecule or biological particle in the droplets; and d. detecting the presence of the target biomolecule or biological particle in the emulsion; wherein said detecting comprises simultaneously quantifying detection signals from multiple layers and from multiple individual droplet contents.

In yet another embodiment the present disclosure provides a method of detecting a target biomolecule or biological particle in a sample comprising: a. combining in a vessel (i) a sample comprising a target biomolecule or biological particle; (ii) a solution comprising reagents for amplifying and detecting the target nucleic acid; (iii) a collection of particles; and (iv) an immiscible carrier; b. agitating the combined solution of (a) under conditions that allow encapsulation of the target biomolecule or biological particle with the reagents for detecting the target biomolecule or biological particle in droplets, thereby forming a monodispersed emulsion; c. incubating the solution of step (b) under conditions that allow detection of the target biomolecule or biological particle in the droplets; and d. merging the droplets and detecting the presence of the biomolecule or biological particle in the emulsion; wherein said detecting comprises quantifying a bulk detection signal from the merged droplets.

In still other embodiment, an aforementioned method is provided wherein said method steps do not use a microwell, microdroplet array or microfluidic device. In other embodiments, the sample comprising the target nucleic acid has not undergone purification steps prior to combining in the vessel of step (a). In another embodiment, the sample comprising the target biomolecule or biological particle has not undergone purification steps prior to combining in the vessel of step (a). In another embodiment, the detecting comprises capturing one or more optical signals. In a related embodiment, the capturing comprises a colorimetric detection assay, fluorescent detection assay, turbidity, and luminescence.

In still other embodiment, an aforementioned method is provided wherein said detecting comprises quantifying a detection signal comprising a quantitation assay selected from the group consisting of sequencing, bioanalyzer, luorescent signal reading, and turbidity reading. In one embodiment, the detecting is carried out with a handheld camera.

In one embodiment, the present disclosure provides and aforementioned method wherein the target nucleic is present in the sample at a low copy number.

In still another embodiment, an aforementioned embodiment is provided wherein the collection of particles is selected from the group consisting of hydrogel beads, plastic beads, glass beads, ceramic beads, and magnetic beads. In one embodiment, the particles are freeze-dried and rehydrated prior to combining in the vessel of step (a).

In yet another embodiment, an aforementioned method is provided wherein the agitating comprises mixing the reagents by pipetting, shaking by hand, stirring, beating, bubbling, vortexing and sonicating. In still another embodiment, an aforementioned method further comprises the step of combining at least one bead to the combined solution of step (b) prior to agitating, wherein the bead is selected from the group consisting of a glass bead, a plastic bead, glass bead, ceramic bead, and magnetic bead.

In one embodiment, the sample comprising the target nucleic acid is a sample obtained from a human subject. In another embodiment, the sample comprising the target biomolecule or biological particle is a sample obtained from a human subject. In some embodiments, the sample is a saliva, blood, urine, or tissue sample.

In yet another embodiment, the present disclosure provides an aforementioned method wherein the solution comprising reagents for amplifying the target nucleic acid comprises reagents suitable for a polymerase chain reaction (PCR) or reagents suitable for a loop-mediated isothermal amplification (LAMP) reaction or reagents for a nucleic acid sequence-based amplification (NASBA) reaction, and optionally comprising a lysing reagent.

In still another embodiment, an aforementioned method is provided wherein the solution comprising reagents for detecting the target biomolecule comprises reagents suitable for a digital enzyme-linked immunosorbent assay (dELISA) reaction, digital oligo-linked immunosorbent assay (dOLISA), digital fluorescence energy transfer assay (dFRET), and digital luciferase reporter assay, and optionally comprising a lysing reagent. In one embodiment, the sample comprising a target biomolecule comprises a protein, and wherein said protein, prior to combining in the vessel of step (a), is bound by a capture antibody and a detection antibody, wherein said capture antibody is bound to a bead and wherein said detection antibody is bound to a detection agent. In still another embodiment, the lysing reagent, when present, is SDS. In still other embodiments, an aforementioned method is provided wherein the vessel in step (a) further comprises a surfactant. In one embodiment, the surfactant is Krytox or PEG-PFPE amphiphilic block copolymer.

In certain embodiments, an aforementioned method is provided wherein the target is a biomolecule, wherein said biomolecule is selected from the group consisting of a nucleic acid or a protein. In still another embodiment, the target is a biological particle, wherein said biological particle is selected from the group consisting of a virus or virus particle, a bacterial cell, a yeast cell, a parasitic cell, or a human cell. In another embodiment, the nucleic acid is from a virus or bacteria or parasite. In certain embodiments, the nucleic acid is from a virus selected from the group consisting of coronavirus, SARS-CoV-2, Huma Immunodeficiency Virus (HIV), Herpes Simplex Virus (HSV), Human Papilloma Virus (HPV), influenza virus, and Respiratory Syncytial Virus (RSV).

The present disclosure also provides an aforementioned method wherein the target nucleic acid is amplified by PCR, RT-PCR, qPCR, digital droplet PCR (ddPCR), LAMP and NASBA.

In one embodiment, an aforementioned method is provided wherein the target nucleic acid, biomolecule or biological particle is detected at a point of care. In one embodiment, 1, 2, 3, 4, 5, 6, 7, 8, 9 or 10 or more different targets are detected.

The present disclosure also provides an aforementioned method wherein said particles generate different compartments during the agitating step (b), wherein each compartment is associated with a different optical signal or different detection signal.

In one embodiment, an aforementioned method is provided wherein the droplets are between approximately 20 μm and 200 μm in size. In one embodiment, the droplets are between approximately 50 μm and 120 μm in size.

In still other embodiments, a method of quantifying a target biomolecule, a method of detecting a genetic abnormality, a method of detecting the presence of a nucleic acid associated with a pathogen, and a method of detecting the presence of SARS-CoV-2 RNA in a sample from a subject according the methods described above are also provided.

The present disclosure also provides methods and reagents for distinguishing a whole virus genome versus a fragmented virus genome in a sample. For example, in one embodiment, the present disclosure provides a method of distinguishing a whole virus genome versus a fragmented virus genome in a sample comprising: a. combining in a vessel (i) a sample comprising a viral genome; (ii) a solution comprising reagents for amplifying and detecting the viral genome; and (iii) an immiscible carrier; b. agitating the combined solution of (a) under conditions that allow encapsulation of the viral genome with the reagents for amplifying and detecting the viral genome in droplets, thereby forming a polydispersed emulsion; c. incubating the solution of step (b) under conditions that allow amplification of the viral genome in the droplets; and d. detecting the presence of the virus genome in the emulsion; wherein the solution comprising reagents for amplifying the viral genome comprises reagents suitable for a polymerase chain reaction (PCR) or reagents suitable for a loop-mediated isothermal amplification (LAMP) reaction, and optionally comprising a lysing reagent, and wherein said reagents comprise two sets of primer pairs, wherein a first primer pair is labeled with a first fluorophore and is capable of amplifying a 5' terminus of the viral genome, when present, and a second primer pair is labeled with a second fluorophore and is capable of amplifying a 3' terminus of the viral genome, when present, and wherein said detecting comprises simultaneously quantifying detection signals from multiple layers and from multiple individual droplet contents.

In still another embodiment, the present disclosure provides a method of distinguishing a whole virus genome versus a fragmented virus genome in a sample comprising: a. combining in a vessel (i) a sample comprising a viral genome; (ii) a solution comprising reagents for amplifying and detecting the viral genome; (iii) a collection of particles; and (iv) an immiscible carrier; b. agitating the combined solution of (a) under conditions that allow encapsulation of the viral genome with the reagents for amplifying and detecting the viral genome in droplets, thereby forming a monodispersed emulsion; c. incubating the solution of step (b) under conditions that allow amplification of the viral genome in the droplets; and d. detecting the presence of the virus genome in the emulsion; wherein the solution comprising reagents for amplifying the viral genome comprises reagents suitable for a polymerase chain reaction (PCR) or reagents suitable for a loop-mediated isothermal amplification (LAMP) reaction, and optionally comprising a lysing reagent, and wherein said reagents comprise two sets of primer pairs, wherein a first primer pair is labeled with a first fluorophore and is capable of amplifying a 5' terminus of the viral genome, when present, and a second primer pair is labeled with a second fluorophore and is capable of amplifying a 3' terminus of the viral genome, when present, and wherein said detecting comprises simultaneously quantifying detection signals from multiple layers and from multiple individual droplet contents.

In yet another embodiment, the present disclosure provides a method of distinguishing a whole virus genome versus a fragmented virus genome in a sample comprising: a. combining in a vessel (i) a sample comprising a viral genome; (ii) a solution comprising reagents for amplifying and detecting the viral genome; and (iii) an immiscible carrier; b. agitating the combined solution of (a) under conditions that allow encapsulation of the viral genome with the reagents for amplifying and detecting the viral genome in droplets, thereby forming a polydispersed emulsion; c. incubating the solution of step (b) under conditions that allow amplification of the viral genome in the droplets, wherein the solution comprising reagents for amplifying the viral genome comprises a first primer pair comprising a 5' forward primer and 5' reverse primer and a second primer pair comprising a 3' forward primer and a 3' reverse primer, wherein the 5' reverse primer and the 3' forward primer each comprise an identical artificial sequence, wherein following amplification of a 5' region and a 3' region from an intact viral genome, said 5' region and 3' region are capable of forming a concatenate molecule comprising the 5' region, the artificial sequence, and the 3' region, d. merging the droplets and performing a quantitative PCR reaction (qPCR)

with a third primer pair capable of amplifying the artificial sequence of the concatenated molecule; and e. detecting the presence of the virus genome in the emulsion wherein said detecting comprises quantifying a bulk detection signal from the merged droplets.

In still another embodiment, the present disclosure provides a method of distinguishing a whole virus genome versus a fragmented virus genome in a sample comprising: a. combining in a vessel (i) a sample comprising a viral genome; (ii) a solution comprising reagents for amplifying and detecting the viral genome; (iii) a collection of particles; and (iv) an immiscible carrier; b. agitating the combined solution of (a) under conditions that allow encapsulation of the viral genome with the reagents for amplifying and detecting the viral genome in droplets, thereby forming a monodispersed emulsion; c. incubating the solution of step (b) under conditions that allow amplification of the viral genome in the droplets, wherein the solution comprising reagents for amplifying the viral genome comprises a first primer pair comprising a 5' forward primer and 5' reverse primer and a second primer pair comprising a 3' forward primer and a 3' reverse primer, wherein the 5' reverse primer and the 3' forward primer each comprise an identical artificial sequence, wherein following amplification of a 5' region and a 3' region from an intact viral genome, said 5' region and 3' region are capable of forming a concatenate molecule comprising the 5' region, the artificial sequence, and the 3' region, d. merging the droplets and performing a quantitative PCR reaction (qPCR) with a third primer pair capable of amplifying the artificial sequence of the con- catentated molecule; and e. detecting the presence of the virus genome in the emulsion wherein said detecting com- prises quantifying a bulk detection signal from the merged droplets.

In some embodiments, an aforementioned method is provided wherein each droplet contains a single viral genome. In some embodiments, an aforementioned method is provided wherein the first fluorophore and second fluo- rophore emit different color when excited. In other embodi- ments, an aforementioned method is provided wherein the detecting the presence of the intact virus genome in the sample comprises quantifying the amount or number of intact viral genomes in the sample. In other embodiments, an aforementioned method is provided wherein said method steps do not use a microwell, microdroplet array or micro- fluidic device.

In still other embodiments, an aforementioned method is provided wherein said sample comprising the virus genome has not undergone purification steps prior to combining in the vessel of step (a). In other embodiments, an aforemen- tioned method is provided wherein said detecting comprises capturing one or more optical signals. In one embodiment, said capturing comprises a fluorescent detection assay. In yet other embodiments, an aforementioned method is provided wherein the virus genome is present in the sample at a low copy number. In other embodiments, the collection of par- ticles is selected from the group consisting of hydrogel beads, plastic beads, glass beads, ceramic beads, and mag- netic beads. In some embodiments, the particles are freeze- dried and rehydrated prior to combining in the vessel of step (a).

In yet other embodiments, an aforementioned method is provided wherein the agitating comprises mixing the reagents by pipetting, shaking by hand, stirring, beating, bubbling, vortexing and sonicating. In other embodiments, an aforementioned method is provided further comprising the step of combining at least one bead to the combined solution of step (b) prior to agitating, wherein the bead is selected from the group consisting of a glass bead, a plastic bead, glass bead, ceramic bead, and magnetic bead.

In other embodiments, an aforementioned method is provided wherein the sample comprising the target nucleic acid is a sample obtained from a human subject. In some embodiments, the sample is a saliva, blood, urine, or tissue sample.

In other embodiments, an aforementioned method is provided wherein the sample comprises a virus selected from the group consisting of coronavirus, SARS-CoV-2, Huma Immunodeficiency Virus (HIV), Herpes Simplex Virus (HSV), Human Papilloma Virus (HPV), influenza virus, and Respiratory Syncytial Virus (RSV).

In yet other embodiments, an aforementioned method is provided wherein the virus genome is amplified during one or more method steps by an amplification reaction selected from the group consisting of PCR, RT-PCR, qPCR, digital droplet PCR (ddPCR), LAMP and NASBA. In other embodiments, an aforementioned method is provided wherein the virus genome is detected at a point of care.

In still other embodiments, an aforementioned method is provided wherein the droplets are between approximately 20 μm and 200 μm in size. In other embodiments, the droplets are between approximately 50 μm and 120 μm in size.

In other embodiments of the present disclosure, a method of detecting a target nucleic acid in a sample is provided comprising: a. combining in a vessel (i) a sample comprising a target nucleic acid; (ii) a solution comprising reagents for amplifying and detecting the target nucleic acid; and (iii) an immiscible carrier; b. agitating the combined solution of (a) under conditions that allow encapsulation of the target nucleic acid with the reagents for amplifying and detecting the target nucleic acid in droplets, thereby forming a monodispersed emulsion; c. incubating the solution of step (b) under conditions that allow amplification of the target nucleic acid in the droplets; and d. detecting the presence of the target nucleic acid in the emulsion; wherein said detect- ing comprises simultaneously quantifying detection signals from multiple layers and from multiple individual droplet contents.

In another embodiment, a method of detecting a target nucleic acid in a sample is provided comprising: a. combin- ing in a vessel (i) a sample comprising a target nucleic acid; (ii) a solution comprising reagents for amplifying and detecting the biomolecule; and (iii) an immiscible carrier; b. agitating the combined solution of (a) under conditions that allow encapsulation of the target nucleic acid with the reagents for amplifying and detecting the target nucleic acid in droplets, thereby forming a monodispersed emulsion; c. incubating the solution of step (b) under conditions that allow amplification of the target nucleic acid in the droplets; and d. merging the droplets and detecting the presence of the target nucleic in the emulsion; wherein said detecting com- prises quantifying a bulk detection signal from the merged droplets.

In still another embodiment, a method of detecting a target biomolecule or biological particle in a sample is provided comprising: a. combining in a vessel (i) a sample comprising a target biomolecule or biological particle; (ii) a solution comprising reagents for detecting the target biomo- lecule; and (iii) an immiscible carrier; b. agitating the combined solution of (a) under conditions that allow encap- sulation of the target biomolecule or biological particle with the reagents for detecting the target biomolecule or biologi- cal particle in droplets, thereby forming a monodispersed emulsion; c. incubating the solution of step (b) under conditions that allow detection of the target biomolecule or biological particle in the droplets; and d. detecting the presence of the target biomolecule or biological particle in the emulsion; wherein said detecting comprises simultaneously quantifying detection signals from multiple layers and from multiple individual droplet contents.

In yet another embodiment, a method of detecting a target biomolecule or biological particle in a sample is provided comprising: a. combining in a vessel (i) a sample comprising a target biomolecule or biological particle; (ii) a solution comprising reagents for detecting the biomolecule; and (iii) an immiscible carrier; b. agitating the combined solution of (a) under conditions that allow encapsulation of the target biomolecule or biological particle with the reagents for detecting the target biomolecule or biological particle in droplets, thereby forming a monodispersed emulsion; c. incubating the solution of step (b) under conditions that allow detection of the target biomolecule or biological particle in the droplets; and d. merging the droplets and detecting the presence of the biomolecule or biological particle in the emulsion; wherein said detecting comprises quantifying a bulk detection signal from the merged droplets.

In some embodiments of the present disclosure, an aforementioned method is provided wherein the target nucleic acid is amplified by a method selected from the group consisting of PCR, RT-PCR, qPCR, digital droplet PCR (ddPCR), LAMP and NASBA; and wherein said quantifying the bulk detection signal comprises quantifying the number of amplicons using an amplification reaction selected from the group consisting of PCR, RT-PCR, qPCR, digital droplet PCR (ddPCR), LAMP, NASBA, bioanalyzer and Qubit. In one embodiment, the target nucleic acid is amplified by digital droplet PCR (ddPCR) and said quantifying the number of amplicons is qPCR. In another embodiment, the target nucleic acid is amplified by digital droplet PCR (ddPCR) and said quantifying the number of amplicons is by bioanalyzer. In still another embodiment, the target nucleic acid is amplified by digital droplet PCR (ddPCR) and said quantifying the number of amplicons is by Qubit.

In still other embodiments of the present disclosure, methods of detecting, and optionally quantitating, one or more polynucleotides are provided that make use of fragment length differences and/or fluorescence intensity.

In one embodiment, a method of detecting the presence of a target polynucleotide in a sample comprising: a. combining in a vessel (i) a sample comprising a target polynucleotide, (ii) a solution comprising reagents for amplifying a sequence of the target polynucleotide, and (iii) an immiscible carrier; b. agitating the combined solution of (a) under conditions that allow encapsulation of the target polynucleotide with the reagents for amplifying a sequence of the target polynucleotide in droplets, thereby forming a polydispersed emulsion; c. incubating the solution of step (b) under conditions that allow amplification of the target polynucleotide in the droplets to form specific and/or non-specific amplification products; and d. merging the droplets and detecting the presence of the target polynucleotide in the emulsion, wherein said detecting comprises measuring the length and, optionally, concentration of the amplification products. In some embodiments, the detecting comprises measuring the length and concentration of the amplification products.

In still another embodiment, the sample comprises 2, 3, 4, 5, 6, 7, 8, 9 or 10 or more target polynucleotides, wherein said detecting comprises measuring the lengths of the amplification products amplified from each target polynucleotide, and wherein the amplification products from each target polynucleotide comprise a unique target fingerprint. In still other embodiments, the target polynucleotide comprises DNA or RNA. In some embodiments, the target polynucleotide is from a virus or bacteria or parasite. In still another embodiment, the specific and/or non-specific amplification products are generated in step (c) by a method selected from the group consisting of LAMP, PCR, and RT-PCR.

In yet another embodiment, an aforementioned method is provided wherein the detecting in step (d) comprises measuring the length and, optionally, concentration of the amplification products using a method selected from the group consisting of capillary electrophoresis and a bioanalyzer. In another embodiment, the incubating conditions in step (c) comprises incubating the solution of step (b) in a volume of approximate 10 μL to 1 mL.

Another embodiment of the present disclosure provides a method of detecting the presence of a target polynucleotide in a sample comprising: a. combining in a vessel (i) a sample comprising a target polynucleotide; (ii) a solution comprising reagents for detecting the target polynucleotide, wherein said reagents comprise primers and wherein said primers each comprise at least one fluorophore; and (iii) an immiscible carrier; b. agitating the combined solution of (a) under conditions that allow encapsulation of the target polynucleotide with the reagents for detecting the target polynucleotide in droplets, thereby forming a polydispersed emulsion; c. incubating the solution of step (b) under conditions that allow amplification of the target polynucleotide in the droplets to form specific and/or non-specific amplification products comprising at least one fluorophore; and d. detecting the presence of the target polynucleotide in the emulsion, wherein said detecting comprises quantifying the fluorescent profile of the amplification products produced by the primers comprising the fluorophores.

In some embodiments, the sample comprises 2, 3, 4, 5, 6, 7, 8, 9 or 10 or more target polynucleotides. In some embodiments, the target polynucleotide comprises DNA or RNA. In some embodiments, the target polynucleotide is from a virus or bacteria or parasite. In yet another embodiment, the specific and/or non-specific amplification products are generated in step (c) by a method selected from the group consisting of LAMP, PCR, and RT-PCR.

The present disclosure further provides an aforementioned method wherein the detecting in step (d) comprises a method selected from the group consisting of fluorescent microscopy, FACS, microfluidic readers, and droplet readers. In still another embodiment, the incubating conditions in step (c) comprises incubating the solution of step (b) in a volume of approximate 10 μL to 1 mL.

The present disclosure also provides a method of detecting the presence of a target polynucleotide in a sample comprising: a. combining in a vessel (i) a sample comprising a target polynucleotide; (ii) a solution comprising reagents for detecting the target polynucleotide, wherein said reagents comprise fluorescently-labeled beads and primers, and wherein said primers each comprise at least one fluorophore; and (iii) an immiscible carrier; b. agitating the combined solution of (a) under conditions that allow encapsulation of the target polynucleotide with the reagents for detecting the target polynucleotide in droplets, thereby forming a polydispersed emulsion; c. incubating the solution of step (b) under conditions that allow amplification of the target polynucleotide in the droplets to form specific and/or non-specific amplification products comprising at least one fluorophore; and d. detecting the presence of the target polynucleotide in the emulsion; wherein said detecting comprises identifying droplets containing the fluorescently-labeled beads, and quantifying the fluorescent profile of the amplification products produced by the primers comprising the fluorophores.

In one embodiment, the primers are conjugated to the fluorescently-labeled beads. In still other embodiments, the sample comprises 2, 3, 4, 5, 6, 7, 8, 9 or 10 or more target polynucleotides. In other embodiments, the target polynucleotide comprises DNA or RNA. In still another embodiment, the target polynucleotide is from a virus or bacteria or parasite. In some embodiments, the specific and/or non-specific amplification products are generated in step (c) by a method selected from the group consisting of LAMP, PCR, and RT-PCR. In some embodiments, the detecting in step (d) comprises a method selected from the group consisting of fluorescent microscopy, FACS, microfluidic readers, and droplet readers. In still other embodiments, the incubating conditions in step (c) comprises incubating the solution of step (b) in a volume of approximate 10 µL to 1 mL.

BRIEF DESCRIPTION OF THE DRAWINGS

FIG. 3 shows that digital droplet PCR (ddPCR) provides robust SARS-CoV-2 viral load measurement across crude lysis conditions.

FIG. 4 shows that digital droplet PCR (ddPCR), but not bulk qRT-PCR, accurately quantifies SARS-CoV-2 viral load from patient nasopharyngeal samples without nucleic acid isolation. (FIG. 4A) $C_t$ values for qRT-PCR from purified RNA (black) versus RNA prepared from crude lysate (gray) shows decreased PCR efficiency without upfront nucleic acid purification of patient samples as evidenced by increase $C_t$ values (n=32 samples). (FIG. 4B) Absolute quantification by ddPCR from crude lysate show strong concordance with qRT-PCR from purified RNA in contrast to qRT-PCR from crude lysate (n=22 samples).

FIG. 8 shows the simulation results for expanding the dynamic range of the digital assay by mixing various sized droplets. Left: theoretical droplet counts within an imaging window with various mixing ratio. Middle: The upper and lower detection limit at 20% precision of large (dark/black) and small (gray) droplets with various mixing ratio. Left: Calculated dynamic range. The red and blue solid line indicates the dynamic range if only small and large droplets were used. The black dots represent the dynamic range of mixed large and small droplet with various mixing ratio. In the case of 50 um and 120 um diameter sized droplet, the widest dynamic range can be achieved by mixing 7% 50 um droplets and 93% 120 um droplets.

FIG. 13 shows bulk quantitation of ddPCR products. (a) Total fluorescence of ddPCR emulsions measured with a plate reader (Tecan); (b) Detection of stained total DNA recovered from ddPCR emulsions (Qubit); (c) Quantitation of amplicon peak with gel electrophoresis (Bioanalyzer) of ddPCR emulsions. (d) qPCR quantitation of ddPCR amplicons. ddPCR+qPCR shifts the qPCR C_t to lower cycles, allowing enhanced sensitivity compared to qPCR alone. n=3, error bars represent standard deviation.

FIG. 14 shows vortex emulsification with qPCR readout enables accurate bulk ddPCR. (FIG. 14A) The DNA sample is added to a tube, oil with stabilizing surfactant is introduced, and the mixture emulsified by vortexing. (FIG. 14B) Vortexed emulsions are thermally cycled. An aliquot is amplified with TaqMan probes to enable visualization. (FIG. 14C) Size distribution of the vortex emulsified droplets obtained by imaging (n=1323). (FIG. 14D) qPCR readout of vortex-emulsified ddPCR allows accurate quantitation of targets over a range of concentrations.

FIG. 15 shows an analysis of preliminary ddLAMP-bulk readout suggesting correlation between bulk readout and input concentration. (FIG. 15A) Qubit readout of ddLAMP product based on COVID input. (FIG. 15B) Bioanalyzer traces identifying size distribution of ddLAMP product based on COVID input. Integral of intensity based on the (FIG. 15C) max and (FIG. 15D) percentile of the ddLAMP product from the bioanalyzer data with associated logarithmic fits. (FIG. 15E) R2 analysis of logarithmic fit for the integral of intensity from the bioanalyzer.

FIG. 16A and FIG. 16B shows the results of a portable smartphone-based fluorescence reader and multi-layer chip for the ddLAMP imaging and quantification.

DETAILED DESCRIPTION

Figure 1:
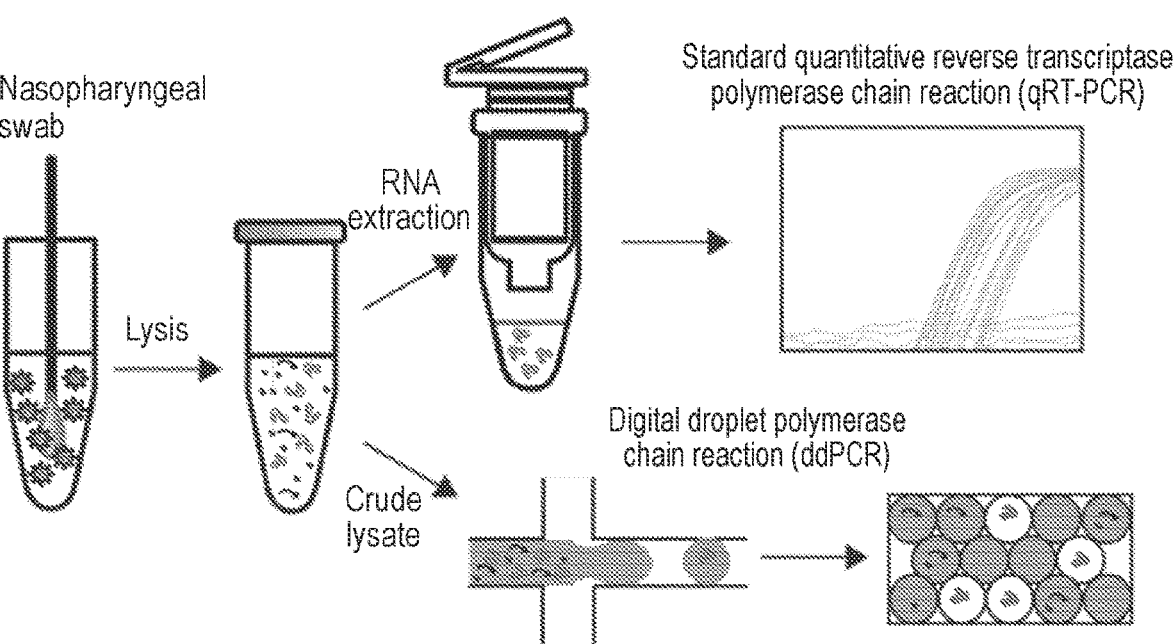
FIG. 1 shows a comparison of the CDC SARS-CoV-2 detection assay requiring RNA extraction followed by bulk qRT-PCR (top workflow) versus our ddPCR approach directly on crude lysate (bottom workflow). Gray molecules represent target nucleic acids while black molecules represent viral proteins and other reaction inhibitors present in unpurified cell lysate. Digital droplet PCR potentially improves viral load quantification by sequestering reaction inhibitors in separate droplet from target nucleic acid sequences.

Provided herein are methods for the generation and detection of droplets providing improved detection and quantification of biomolecules. These techniques include the generation of droplets using particle-templated emulsification, microfluidic chips, and vortexing. Improved detection leverages single or multiplexed fluorescent detection or an alternative bulk fingerprint readout as described in detail herein.

Particle-templated emulsification (PTE) allows for separation and encapsulation of samples during vortexing. See, e.g., WO/2019/139650, incorporated by reference in its entirety herein. However, while the aforementioned method generates a monodisperse emulsion that encapsulates target particles of interest without requiring the use of a microfluidic device, this method usually generates satellite droplets that may cause template loss and quantification bias.

In some droplet-based multivolume techniques, the method requires fabrication of microfluidic chips with multi-volume chambers or micropillar with multi-sized surface areas (See, e.g., Liu, W-W., et al., Anal. Chem. 2017, 89, 822-829; Shen, F., et al., J. Am. Chem. Soc., 2011, 133, 17705-17712; and Kreutz, J., et al., Anal. Chem., 2011, 83, 8159-8168)

The present disclosure addresses the aforementioned unmet need by providing methods and materials for detecting biomolecules and biological particles, including nucleic acids and viral genomes, that can be practiced at the point of care for a patient or human subject.

As described herein, in various embodiments the present disclosure provides timely bedside point of care detection for pathogens with minimal instrumentation. The invention allows the encapsulation, lysis, and verification/detection through the microfluidic-free particle templated emulsification of patient samples.

In one embodiment, a simple, direct nucleic acid isolation and preparation of patient samples is provided with minimal instrumentation. In some embodiments, the present disclosure provides co-encapsulating samples with lysis reagents such as SDS, thereby allowing lysis of, for example, pathogenic capsules and other vectors. The present disclosure thus provides in one embodiment a rapid method of sample isolation and processing that is highly conducive to non-laboratory settings possessing minimal equipment. Such settings include patient bedside point of care, airport testing, and on-site field testing.

In another embodiment, the present disclosure provides a methodology of combining samples and assay followed by vortexing to encapsulate. This enables different assays to be performed by exchanging reagents. Different pathogenic or chemical targets can be changed with the addition of different particles and reagent mixtures. This provides the ability to address a wide range of assays with one product and identical protocol; an ideal situation for point of care environments.

In still another embodiment of the present disclosure, transparent emulsions are achieved by matching the aqueous (particle) phase and oil phase index of refractions (e.g., merging). This merging is accompanied by a single colorimetric or fluorescent positive detection and thus allows for a single bulk verification of the assay outcome. Furthermore, a single positive indication reduces the result to a simple digital/binary interpretation (yes or no). As described herein, the direct bulk colorimetric or fluorescent verification can be performed via low tech imaging options, including Android and iPhones. This avoids the need for more complex, bulky, or expensive instrumentation allowing for a broader range of point of care environments to utilize this technology.

The methods described herein thus possesses several key innovations over existing technologies. By regulating the size of particles and thereby the attached primers and reagent volumes, a broader range of assay sensitivities can be achieved. The use of particle templated emulsification allows for thousands to millions of target samples to be encapsulated and assayed on a single target basis.

The present disclosure also provides, in various embodiments, methods to increase the sensitivity and expand the dynamic range of partition-based digital assays through the simultaneous use of different volume partitions with different sensitivities and dynamic ranges.

In various embodiments provided herein, droplets comprising, for example, a target nucleic acid or a target biomolecule, are generated following agitation as described herein. In still other embodiments, the droplets are formed using a microfluidic chip or device according to known techniques (e.g., passage of fluids through an orifice so as to generate partitioned fluid sections) (WO2010110842A1).

In some embodiments of the present disclosure, methods are provided based on digital droplet PCR (ddPCR) followed by conventional quantitative PCR (qPCR) to robustly amplify and quantify DNA from low concentration samples. By coupling an initial dPCR to a subsequent qPCR, the methods described herein obtain significantly more accurate and precise DNA quantification at the current limit of detection compared to conventional PCR. The present disclosure thus presents opportunities to enable analysis of low abundance DNA samples obtained across diverse contexts including cancer, infectious disease, and environmental microbial samples.

As described herein, the present disclosure addresses the critical challenge of robust DNA detection, amplification, and quantification from low abundance samples. Current methods are limited by numerous factors including false positives due to non-specific amplification, false negatives due to reaction inhibition, and poor quantitative resolution at low DNA input amounts. Such shortcomings not only directly impact DNA detection but also impairs downstream applications from low abundance DNA samples such as library construction for high throughput sequencing. Digital droplet PCR (ddPCR) partitions the input DNA molecules in a sample into thousands of nanoliter droplets, each of which functions as a separate reaction chamber. Partitioning improves the analytical sensitivity and selectivity of PCR by increasing the relative amount of target in each droplet and segregating potential PCR inhibitors into separate reaction chambers. In some embodiments the methods described herein take advantage of this inherent compartamentalization to perform initial DNA amplification with ddPCR followed by conventional PCR amplification in bulk using this preamplified input template DNA. In some embodiments, the methods of the present disclosure couple the sensitivity and selectivity of ddPCR with widely used conventional PCR or qPCR methods for readout.

Accurate detection and quantification of biomolecules are critical for biological and medical research as well as disease diagnosis and prognosis. Digital assays distribute target biomolecules such as DNA, RNA, viral particles, or proteins into many partitions such that each partition contains a number of molecules (0, 1, 2, etc.), theoretically following a Poisson distribution. After certain signal amplification reactions of the target molecules, those partitions with and without target biomolecules could be counted as positive and negative, thus the concentration could be 'digitally' measured by applying Poisson statistics ($C=\lambda/Vp$, where $C$ is the concentration of target molecule, Vd is the volume of individual partition, and X is the percentage of negative counts). The digital assays are accurate when $\lambda$ is within a range suitable for Poisson quantification (0.001-6). However, this requirement has several limitations. First, samples must be properly diluted to a concentration within a well-defined confidence interval. Thus, a high concentration sample typically requires a rerun with correctly diluted concentration, which cause reagent waste and extended assay time. Second, to minimize error, large number of partitions are required. Because current available techniques rely on detection methods based on fluorescent imaging or laser-induced fluorescence, the throughput of the detection methods is limited in terms of partitioning counts or need long time to process enough partitions. The present disclosure provides techniques that improve the detection sensitivity and widen the dynamic range of the digital assays and overcome the issues listed above, as described herein.

As described herein, one application of the present disclosure relates to the detection and/or quantitation of nucleic acid molecules from human patient samples where the patient is infected with a pathogen. For example, absolute viral load quantification directly from crude lysate and without nucleic acid purification, important for diagnosis and surveillance, is obtainable by the methods provided herein. For example, digital droplet PCR (ddPCR) accurately quantifies SARS-CoV-2 standards from purified RNA and multiple sample matrices, including commonly utilized universal transport medium (UTM). In addition, the present disclosure provides that ddPCR functions robustly at low input viral copy numbers on nasopharyngeal swab specimens stored in UTM without upfront RNA extraction. Additionally, the present disclosure shows that ddPCR, but not qPCR, from crude lysate shows high concordance with viral load measurements from purified RNA. ddPCR detected SARS-CoV-2 viral copies in a clinically suspicious case negative by conventional qPCR. The present disclosure thus demonstrates that ddPCR offers advantages to qPCR for pathogen detection, including SARS-CoV-2 detection, with higher sensitivity and robustness when using crude lysate rather than purified RNA as input. Digital droplet assays thus provide a method for nucleic acid measurement and infectious disease diagnosis requiring limited sample processing.

In still other embodiments of the present disclosure, methods are provided for the detection of nucleic acids from a sample which are simpler, faster, and more sensitive compared to what can be achieved with qPCR and conventional commercial digital droplet PCR platforms. For example, the multiplexed methods disclosed herein provide a simplified way to do complex and rapid multiplex analysis of a sample either using common core facility equipment (electrophoresis) or a simple one-tube, self-contained optical system akin to a smart-phone microscope. Further, in addition to multiplexing capacity, the use of droplets, in various embodiments and methods provided herein, provides a high-accuracy absolute quantification simultaneously for all targets being tested for. The use of droplets also means that such quantification is less affected by inhibitory compounds within the sample matrix.

Definitions

As used herein, the term "sample" or "biological sample" encompasses a variety of sample types obtained from a variety of sources, which sample types contain biological material. For example, the term includes biological samples obtained from a mammalian subject, e.g., a human subject, and biological samples obtained from a food, water, or other environmental source, etc. The definition encompasses blood and other liquid samples of biological origin, as well as solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides. The term "sample" or "biological sample" encompasses a clinical sample, and also includes cells in culture, cell supernatants, cell lysates, cells, serum, plasma, biological fluid, and tissue samples. "Sample" and "biological sample" includes cells, e.g., bacterial cells or eukaryotic cells; biological fluids such as blood, cerebrospinal fluid, semen, saliva, and the like; bile; bone marrow; skin (e.g., skin biopsy); and viruses or viral particles obtained from an individual.

As described more fully herein, in various aspects the subject methods may be used to detect and/or quantify a variety of components from such biological samples. Components of interest include, but are not necessarily limited to, cells (e.g., circulating cells and/or circulating tumor cells), viruses and viral genomes, polynucleotides (e.g., DNA and/or RNA), polypeptides (e.g., peptides and/or proteins), and many other components that may be present in a biological sample.

As used herein, the term "monodisperse," as applied to particles or droplets, refers to a variation in diameter or largest dimension of the particles such that at least 50% or more, e.g., 60% or more, 70% or more, 80% or more, 90% or more, 95% or more, or 99% or more of the template particles vary in diameter or largest dimension by less than a factor of 10, e.g., less than a factor of 5, less than a factor of 4, less than a factor of 3, less than a factor of 2, less than a factor of 1.5, less than a factor of 1.4, less than a factor of 1.3, less than a factor of 1.2, less than a factor of 1.1, less than a factor of 1.05, or less than a factor of 1.01. In some embodiments, monodisperse droplets have a diameter of about 1.0 pm to 1000 pm, inclusive, such as about 1.0 pm to about 750 pm, about 1.0 pm to about 500 pm, about 1.0 pm to about 250 pm, about 1.0 pm to about 200 pm, about 1.0 pm to about 150 pm, about 1.0 mih to about 100 mih, about 1.0 mih to about 10 mih, or about 1.0 mih to about 5 mhi, inclusive. In some embodiments, the internal volume of the monodisperse droplets may be about 0.01 pL or less, about 0.1 pL or less, 1 pL or less, about 5 pL or less, 10 pL or less, 100 pL or less, or 1000 pL or less. In some embodiments, the internal volume of the monodisperse droplets may be about 1 fL or less, about 10 fL or less, or 100 fL or less. In some embodiments, the internal volume of the monodisperse droplets may encompass a liquid volume which ranges between picoliters and femotliters (e.g., about 0.001 pL to about 1000 pL). In some embodiments, the internal volume of the monodisperse droplets extends at the nanoliter level or below the nanoliter level (e.g., strictly picoliter, strictly femtoliter, or combination thereof). Thus, the term "polydisperse" refers to an emulsion comprising non-uniform particles or droplets with unequal sizes.

The terms "polynucleotide" and "nucleic acid" and "target nucleic acid" refer to a polymer composed of a multiplicity of nucleotide units (ribonucleotide or deoxyribonucleotide or related structural variants) linked via phosphodiester bonds. A polynucleotide or nucleic acid can be of substantially any length, typically from about six (6) nucleotides to about $10^9$ nucleotides or larger. Polynucleotides and nucleic acids include RNA, cDNA, genomic DNA. In particular, the polynucleotides and nucleic acids of the present invention refer to polynucleotides encoding a chromatin protein, a nucleotide modifying enzyme and/or fusion polypeptides of a chromatin protein and a nucleotide modifying enzyme, including mRNAs, DNAs, cDNAs, genomic DNA, and polynucleotides encoding fragments, derivatives and analogs thereof. Useful fragments and derivatives include those based on all possible codon choices for the same amino acid, and codon choices based on conservative amino acid substitutions. Useful derivatives further include those having at least 50% or at least 70% polynucleotide sequence identity, and more preferably 80%, still more preferably 90% sequence identity, to a native chromatin binding protein or to a nucleotide modifying enzyme.

The term "oligonucleotide" refers to a polynucleotide of from about six (6) to about one hundred (100) nucleotides or more in length. Thus, oligonucleotides are a subset of polynucleotides. Oligonucleotides can be synthesized manually, or on an automated oligonucleotide synthesizer (for example, those manufactured by Applied BioSystems (Foster City, CA)) according to specifications provided by the manufacturer or they can be the result of restriction enzyme digestion and fractionation.

The term "primer" as used herein refers to a polynucleotide, typically an oligonucleotide, whether occurring naturally, as in an enzyme digest, or whether produced synthetically, which acts as a point of initiation of polynucleotide synthesis when used under conditions in which a primer extension product is synthesized. A primer can be single-stranded or double-stranded. In some embodiments, as is well known in the art, primers may be designed in "primer pairs" as described herein. In some embodiments, the present disclosure provides methods of using various primer sets or pairs to amplify regions or portions of a viral genome. In some embodiments, amplified regions may share a region of homology (e.g., a bridge) that can serve as a source for concatenation as is known in the art.

The term "nucleic acid array" as used herein refers to a regular organization or grouping of nucleic acids of different sequences immobilized on a solid phase support at known locations. The nucleic acid can be an oligonucleotide, a polynucleotide, DNA, or RNA. The solid phase support can be silica, a polymeric material, glass, beads, chips, slides, or a membrane. The methods of the present invention are useful with both macro- and micro-arrays.

The term "protein" or "protein of interest" (e.g., as it relates to a target biomolecule) refers to a polymer of amino acid residues, wherein a protein may be a single molecule or may be a multi-molecular complex. The term, as used herein, can refer to a subunit in a multi-molecular complex, polypeptides, peptides, oligopeptides, of any size, structure, or function. It is generally understood that a peptide can be 2 to 100 amino acids in length, whereas a polypeptide can be more than 100 amino acids in length. A protein may also be a fragment of a naturally occurring protein or peptide. The term protein may also apply to amino acid polymers in which one or more amino acid residues is an artificial chemical analogue of a corresponding naturally occurring amino acid. A protein can be wild-type, recombinant, naturally occurring, or synthetic and may constitute all or part of a naturally-occurring, or non-naturally occurring polypeptide. The subunits and the protein of the protein complex can be the same or different. A protein can also be functional or non-functional.

Generally, other nomenclature used herein and many of the laboratory procedures in cell culture, molecular genetics and nucleic acid chemistry and hybridization, which are described below, are those well-known and commonly employed in the art. (See generally Ausubel et al. (1996) supra; Sambrook et al, Molecular Cloning: A Laboratory Manual, Second Edition, Cold Spring Harbor Laboratory Press, New York (1989), which are incorporated by reference herein). Standard techniques are used for recombinant nucleic acid methods, polynucleotide synthesis, preparation of biological samples, preparation of cDNA fragments, isolation of mRNA and the like. Generally enzymatic reactions and purification steps are performed according to the manufacturers' specifications.

Methods

The present disclosure provides methods and materials for detecting and/or quantifying nucleic acids, biomolecules such as proteins, and biological particles such as viruses and cells. As described herein, the emulsions contemplated herein may be monodispersed or polydispersed. The methods also provides various means of agitating the samples/solutions described herein. By way of example, agitating can mean simple mixing of two solutions, pipetting, shaking or flicking the vessel by hand, vortexing and/or sonicating. In some embodiments, "agitating" includes mixing or passing fluids through an orifice so as to generate partitioned fluid sections, e.g., on or in a microfluidic chip or device. Other means of agitation are known to those of ordinary skill in the art.

"Detecting" as used herein generally means identifying the presence of a target, such as a target nucleic acid or protein. In various embodiments, detection signals are produced by the methods described herein, and such detections signals may be optical signals which may include but are not limited to, colorimetric changes, fluorescence, turbidity, and luminescence. Detecting, in still other embodiments, also means quantifying a detection signal, and the quantifiable signal may include, but is not limited to, transcript number, amplicon number, protein number, and number of metabolic molecules. In this way, sequencing or bioanalyzers are employed in certain embodiments.

As described herein, detecting may also include "quantitating" or "quantitation" (e.g., determination of the concentration, including concentration relative to other present nucleic acids or biomolecules). Further, the methods provided herein also include detecting the presence of a virus in a human sample, or detecting a mutation in a polynucleotide sequence, e.g., from a virus.

The "conditions" of the methods provided herein may preferably promote the inclusion of 1 target (e.g., nucleic acid) per droplet as described herein.

The present disclosure provides methods that generate, and then detect and/or quantitate, amplification products that include specific amplification products and/or non-specific amplification products. As used herein "specific" amplification products refers to targeted nucleic amplicons resulting from an amplification reaction, typically bracketed by primers specific to the target. "Non-specific" amplification products, as used herein, refers to byproduct nucleic amplicons that may result from successful specific amplification.

In various embodiments, a fluorescent profile that is produced by fluorophores is detected. As used herein, "fluorescent profile" means the fluorescent signal comprised of one or more wavelengths generated through the excitation of specific/defined concentrations and combinations of fluorescent probes used to identify a specific target. Various means of detecting fluorsecene or fluorescent profiles are known in the art and are provided herein, including, for example fluorescent microscopy, FACS, microfluidic readers, and droplet readers. Generally, any means of fluorescent microscopy can be applied. FACS (fluorescence activated cell sorting), for example, is possible with, for example, conversion to double emulsions. Reinjection of droplets into a microfluidic device using optics to fluorescently detect/analyze the droplets is also contemplated. Droplet readers (instruments like BioRad QX200) are microfluidic devices capable of detecting droplet fluorescence for analysis and are also contemplated herein.

As described herein, the detection step, which optionally includes capturing an image or quantifying a signal, comprises (1) simultaneously quantifying detection signals from multiple layers and from multiple individual droplet contents, or in other embodiments (2) quantifying a bulk detection signal from the merged droplets.

In various embodiments, one advantage of the present disclosure is the lack of need for instrumentations such as microwells, microdroplet arrays or microfluidic devices. Another advantage as described herein includes the lack of need to purify samples prior to processing or otherwise combining in the vessels for detection. Unlike prior techniques, the present methods optionally do not require nucleic acid purification steps prior to practicing the methods. Crude lysates can be used in some embodiments. As described herein, inhibitors of, for example, PCR or other reactions, are sequestered in droplets and, as a result, are unable to interfere with the desired reaction.

Numerous means for capturing images, and optionally quantifying data points within such images, are provided herein. For example, image capturing/quantifying devices include but are not limited to, fluorescent microscope, handheld phones, plate reader, imaging system, real-time PCR machine can be used.

In still other embodiments, the present disclosure provides methods wherein the target nucleic acid is present in the sample at a low copy number, for example, 1-50 copies.

Some methods of the present disclosure include particles that provide monodispersed emulsions. As described herein, particles include, but are not limited to, hydrogel beads, plastic beads, glass beads, ceramic beads, and magnetic beads. In certain embodiments, the hydrogel is selected from naturally derived materials, synthetically derived materials and combinations thereof. Examples of hydrogels include, but are not limited to, collagen, hyaluronan, chitosan, fibrin, gelatin, alginate, agarose, chondroitin sulfate, polyacrylamide, polyethylene glycol (PEG), polyvinyl alcohol (PVA), polyacrylamide/poly(acrylic acid) (PAA), hydroxyethyl methacrylate (HEMA), poly N-isopropyl acrylamide (NIP AM), and polyanhydrides, polypropylene fumarate) (PPF).

In some embodiments, the particles are freeze-dried and rehydrated prior to combining in the vessel.

In still other embodiments of the disclosure, at least one bead is combined in the vessel prior to agitating, thereby increasing the strength of agitation. Beads may be glass, plastic, glass, ceramic, magnetic in various embodiments.

According to some embodiments of the present disclosure, a lysing reagent is used in the detection methods. Lysing agents may include, for example chemical lysis, such as SDS, detergents, alkaline, and acid; biological lysis, such as lysis enzymes, viruses, and phages; and physical lysis such as beads beating, grinding, frozen-thaw, and sonication.

In certain aspects, a surfactant may be included in the vessels and methods described herein. Accordingly, a droplet may involve a surfactant stabilized emulsion, e.g., a surfactant stabilized single emulsion or a surfactant stabilized double emulsion. Any convenient surfactant that allows for the desired reactions to be performed in the droplets may be used, including, but not limited to, octylphenol ethoxylate (Triton X-100), polyethylene glycol (PEG), $C_{26}H_{50}O_{10}$ (Tween 20) and/or octylphenoxypolyethoxyethanol (IGEPAL). In other aspects, a droplet is not stabilized by surfactants. The surfactant used depends on a number of factors such as the oil and aqueous phases (or other suitable immiscible phases, e.g., any suitable hydrophobic and hydrophilic phases) used for the emulsions. For example, when using aqueous droplets in a fluorocarbon oil, the surfactant may have a hydrophilic block (PEG-PPO) and a hydrophobic fluorinated block (Krytox® FSH). If, however, the oil was switched to a hydrocarbon oil, for example, the surfactant may instead be chosen such that it had a hydrophobic hydrocarbon block, like the surfactant ABIL EM90.

Other surfactants can also be envisioned, including ionic surfactants. Other additives can also be included in the oil to stabilize the droplets, including polymers that increase droplet stability at temperatures above 35° C. Without intending to be bound by any particular theory, it is proposed that the preparation of a thermostable emulsions relies on the use of a surfactant that is able to form membranes or double emulsion interfaces that can optionally withstand high temperatures, such as those associated with standard PCR reactions. One way to accomplish this may be to use a surfactant with a relatively high molecular weight so that when assembled at the interface of a droplet or in a membrane configuration, the energy required to remove the surfactant from the interface (or break the membrane) is higher than can be provided by kT. Exemplary surfactants which may be utilized to provide thermostable emulsions are the "biocompatible" surfactants that include PEG-PFPE (polyethyleneglycol-perflouropolyether) block copolymers, e.g., PEG-Krytox® (see, e.g., Holtze et ak, "Biocompatible surfactants for water-in-fluorocarbon emulsions," Lab Chip, 2008, 8, 1632-1639, the disclosure of which is incorporated by reference herein), and surfactants that include ionic Krytox® in the oil phase and Jeffamine® (polyetheramine) in the aqueous phase (see, e.g., DeJoumette et ak, "Creating Biocompatible Oil-Water Interfaces without Synthesis: Direct Interactions between Primary Amines and Carboxylated Perfluorocarbon Surfactants", Anal. Chem. 2013, 85(21): 10556-10564, the disclosure of which is incorporated by reference herein). Additional and/or alternative surfactants may be used provided they form stable interfaces. Many suitable surfactants will thus be block copolymer surfactants (like PEG-Krytox®) that have a high molecular weight. These examples include fluorinated molecules and solvents, but it is likely that non-fluorinated molecules can be utilized as well.

The present disclosure provides methods of detecting a target in a sample, where the target may be, for example, a nucleic acid (RNA, DNA), biomolecules such nucleic acids, genes, proteins or polypeptides or epitopes, as well as biological particles such as cells (bacterial, human, parasite) and viruses.

Exemplary pathogenic bacteria or bacterial cells include, for example, members of the genus *Actinomyces, Bacillus, Bacteroides, Bordetella, Bartonella, Borrelia* (e.g., *B. burgdorferi* OspA), *Brucella, Campylobacter, Capnocytophaga, Chlamydia, Corynebacterium, Coxiella, Dermatophilus, Enterococcus, Ehrlichia, Escherichia, Francisella, Fusobacterium, Haemobartonella, Haemophilus* polypeptides, *Helicobacter, Klebsiella*, L-form bacteria, *Leptospira, Listeria, Mycobacteria, Mycoplasma, Neisseria, Neorickettsia, Nocardia, Pasteurella*, Peptococcus, *Peptostreptococcus*, Pneumococcus polypeptides (i.e., *S. pneumoniae* polypeptides), *Proteus, Pseudomonas, Rickettsia, Rochalimaea, Salmonella, Shigella, Staphylococcus*, group A *streptococcus* (e.g., *S. pyogenes*), group B *streptococcus* (*S. agalactiae*), *Treponema*, and *Yersinia*.

Exemplary pathogenic viruses or virus particles or viral genomes include, for example, adenovirus, alphavirus, calicivirus (e.g., a calicivirus capsid antigen), coronavirus polypeptides, distemper virus, Ebola virus polypeptides, enterovirus, flavivirus, hepatitis virus (AE), herpesvirus, infectious peritonitis virus, leukemia virus, Marburg virus, orthomyxovirus, papilloma virus, parainfluenza virus, paramyxovirus, parvovirus, pestivirus, picorna virus (e.g., a poliovirus), pox virus (e.g., a vaccinia virus), rabies virus, reovirus, retrovirus, and rotavirus. In certain embodiments, the virus is SARS-CoV-2, HIV, HSV, or HPV.

Exemplary parasites include protozoan parasites, for example, members of the *Babesia, Balantidium, Besnoitia, Cryptosporidium, Eimeria, Encephalitozoon, Entamoeba, Giardia, Hammondia, Hepatozoon, Isospora, Leishmania, Microsporidia, Neospora, Nosema, Pentatrichomonas, Plasmodium*. Examples of helminth parasites include, but are not limited to, *Acanthocheilonema, Aelurostrongylus, Ancylostoma, Angiostrongylus, Ascaris, Brugia, Bunostomum, Capillaria, Chabertia, Cooperia, Crenosoma, Dictyocaulus, Dioctophyme, Dipetalonema, Diphyllobothrium, Diplydium, Dirofilaria, Dracunculus, Enterobius, Filaroides, Haemonchus, Lagochilascaris, Loa, Mansonella, Muellerius, Nanophyetus, Necator, Nematodirus, Oesophagostomum, Onchocerca, Opisthorchis, Ostertagia, Parafilaria, Paragonimus, Parascaris, Physaloptera, Protostrongylus, Setaria, Spirocerca Spirometra, Stephanofilaria, Strongyloides, Strongylus, Thelazia, Toxascaris, Toxocara, Trichinella, Trichostrongylus, Trichuris, Uncinaria*, and *Wuchereria. Pneumocystis, Sarcocystis, Schistosoma, Theileria, Toxoplasma*, and *Trypanosoma* are also contemplated.

The present disclosure has, in various embodiments, the advantage of being implemented and practiced to completion at the point of care. "Point of care" may be, for example, at a hospital, school, airport, home or other environment where an immediate determination is important.

As described herein, the present detection methods include droplets, e.g., droplets of oil, of varying sizes. In one embodiment, the droplets are between approximately 10 μm and 300 μm or 20 μm and 200 μm in size. In another embodiment, the droplets are between approximately 50 μm and 120 μm in size.

Suitable subjects for the methods disclosed herein include mammals, e.g., humans. The subject may be one that exhibits clinical presentations of a disease condition, or has been diagnosed with a disease. In certain aspects, the subject may be one that has been diagnosed with an infection, e.g., COVID-19, or cancer, exhibits clinical presentations of infection or cancer.

Various embodiments of the present disclosure use a polymerase chain reaction (PCR)-based assay to detect the presence of certain oligonucleotides and/or genes, e.g., oncogene(s) present in cells or nucleic acids associated with a pathogen. Examples of PCR-based assays of interest include, but are not limited to, quantitative PCR (qPCR), quantitative fluorescent PCR (QF-PCR), multiplex fluorescent PCR (MF-PCR), digital droplet PCR (ddPCR) single cell PCR, PCR-RFLP/real time-PCR-RFLP, hot start PCR, nested PCR, in situ polony PCR, in situ rolling circle amplification (RCA), bridge PCR, picotiter PCR, emulsion PCR and reverse transcriptase PCR (RT-PCR). Other suitable amplification methods include the ligase chain reaction (LCR), transcription amplification, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR) and nucleic acid based sequence amplification (NABS A). A PCR-based assay may be used to detect the presence of certain nucleic acids or gene(s). In such assays, one or more primers specific to each gene of interest are reacted with the genome of each cell. To determine whether a particular gene is present, the PCR products may be detected through an assay probing the liquid of a droplet as described herein, such as by staining the solution with an intercalating dye, like SybrGreen or ethidium bromide, hybridizing the PCR products to a solid substrate, such as a bead (e.g., magnetic or fluorescent beads, such as Luminex beads), or detecting them through an intermolecular reaction, such as FRET. These dyes, beads, and the like are each examples of a "detection signal," a term that is used broadly and genetically herein to refer to any component that is used to detect the presence or absence of nucleic acid amplification products, e.g., PCR products.

Loop-mediated isothermal amplification (LAMP) and digital droplet LAMP (ddLAMP) is a single-tube technique for the amplification of DNA and a low-cost alternative to detect certain diseases and is also contemplated herein. Reverse Transcription Loop-mediated Isothermal Amplification (RT-LAMP) combines LAMP with a reverse transcription step to allow the detection of RNA. LAMP is an isothermal nucleic acid amplification technique. In contrast to the polymerase chain reaction (PCR) technology, in which the reaction is carried out with a series of alternating temperature steps or cycles, isothermal amplification is carried out at a constant temperature, and does not require a thermal cycler. In LAMP, the target sequence is amplified at a constant temperature of 60-65° C. using either two or three sets of primers and a polymerase with high strand displacement activity in addition to a replication activity. Typically, 4 different primers are used to amplify 6 distinct regions on the target gene, which increases specificity. An additional pair of "loop primers" can further accelerate the reaction. The amount of DNA produced in LAMP is considerably higher than PCR-based amplification. LAMP and RT-LAMP (<30 min) is much faster than PCR-based assays (>1 h).

In various embodiments, the methods provided herein use an immiscible carrier. Immiscible carriers, which form a non-aqueous phase in the emulsions described herein, include but are not limited to a fluorocarbon oil, a hydrocarbon oil, or a combination thereof; and the third fluid is an aqueous phase fluid. The non-aqueous phase may serve as a carrier fluid forming a continuous phase that is immiscible with water, or the non-aqueous phase may be a dispersed phase. The non-aqueous phase may be referred to as an immiscible carrier or oil phase including at least one oil, but may include any liquid (or liquefiable) compound or mixture of liquid compounds that is immiscible with water. The oil may be synthetic or naturally occurring. The oil may or may not include carbon and/or silicon, and may or may not include hydrogen and/or fluorine. The oil may be lipophilic or lipophobic. In other words, the oil may be generally miscible or immiscible with organic solvents. Exemplary oils may include at least one silicone oil, mineral oil, fluorocarbon oil, vegetable oil, or a combination thereof, among others. In exemplary embodiments, the oil is a fluorinated oil, such as a fluorocarbon oil, which may be a perfluorinated organic solvent. Examples of a suitable fluorocarbon oils include, but are not limited to, C9H5OF15 (HFE-7500), C21F48N2 (FC-40), and perfluoromethyldecalin (PFMD).

In certain embodiments, the present disclosure provides detecting and quantifying a bulk detection signal from a collection of pooled or merged droplets. For example, after ddPCR is done, the droplets are subjected to emulsion breaking by either chemical or physical forces. An aliquot of the merged droplets containing the ddPCR products is then quantified by qPCR or bioanalyzer or Qubit fluorometer.

In practicing certain subject methods, the manner in which nucleic acid synthesis and/or amplification products, e.g., isothermal nucleic acid amplification products or PCR products, can be detected may vary. A variety of different detection components may be used in practicing the subject methods, including using fluorescent dyes known in the art. Fluorescent dyes may typically be divided into families, such as fluorescein and its derivatives; rhodamine and its derivatives; cyanine and its derivatives; coumarin and its derivatives; Cascade Blue and its derivatives; Lucifer Yellow and its derivatives; BOD IP Y and its derivatives; and the like. Exemplary fluorophores include indocarbocyanine (C3), indodicarbocyanine (C5), Cy3, Cy3.5, Cy5, Cy5.5, Cy7, Texas Red, Pacific Blue, Oregon Green 488, Alexa fluor-355, Alexa Fluor 488, Alexa Fluor 532, Alexa Fluor 546, Alexa Fluor-555, Alexa Fluor 568, Alexa Fluor 594, Alexa Fluor 647, Alexa Fluor 660, Alexa Fluor 680, JOE, Lissamine, Rhodamine Green, BODIPY, fluorescein isothiocyanate (FITC), carboxy-fluorescein (FAM), phycoerythrin, rhodamine, dichlororhodamine (dRhodamine), carboxy tetramethylrhodamine (TAMRA), carboxy-X-rhodamine (ROX), LIZ, VIC, NED, PET, SYBR, PicoGreen, RiboGreen, and the like. Descriptions of fluorophores and their use, can be found in, among other places, R. Haugland, Handbook of Fluorescent Probes and Research Products, 9th ed. (2002), Molecular Probes, Eugene, Oreg.; M. Schena, Microarray Analysis (2003), John Wiley & Sons, Hoboken, N.J.; Synthetic Medicinal Chemistry 2003/2004 Catalog, Berry and Associates, Ann Arbor, Mich.; G. Hermanson, Bioconjugate Techniques, Academic Press (1996); and Glen Research 2002 Catalog, Sterling, VA. In some embodiments, the detection or quantification methods described herein use a combination of different detection components. By way of example, different fluorophores can be conjugated to primers that allow the detection of intact/whole viral genomes versus fragmented viral genomes as described herein.

In practicing certain subject methods, therefore, a component may be detected based upon, for example, a change in fluorescence. In certain aspects, the change in fluorescence is due to fluorescence resonance energy transfer (FRET). In this approach, a special set of primers may be used in which the 5' primer has a quencher dye and the 3' primer has a fluorescent dye. These dyes can be arranged anywhere on the primers, either on the ends or in the middles. Because the primers are complementary, they will exist as duplexes in solution, so that the emission of the fluorescent dye will be quenched by the quencher dye, since they will be in close proximity to one another, causing the solution to appear dark. After PCR, these primers will be incorporated into the long PCR products, and will therefore be far apart from one another. This will allow the fluorescent dye to emit light, causing the solution to become fluorescent.

In some embodiments, the methods described herein can be used to quantitate nucleic acids using, for example, digital PCR. In digital PCR, target nucleic acids from a solution are diluted such that, when the sample is isolated in compartments, most compartments encapsulate either zero or one target molecule, although higher loading rates can often be used, provided they can be modeled. Reagents sufficient for amplification of the target nucleic acids are also included in the compartments, and the compartments subjected to conditions suitable for amplification. The compartments can have a variety of structures, including fabricated microwells in a substrate or single-emulsion droplets.

Droplets that contain a target nucleic acid undergo amplification, while those that do not, do not undergo amplification, and therefore do not yield nucleic acid amplification products, including detection signals. If a detection component/signal is included, single or multiple emulsions that include the target may fill with a detectable signal, allowing them to be identified by, for example, imaging or flow dropometry. A powerful advantage of using double emulsions to perform such digital PCR is that the double emulsions can be suspended in an aqueous carrier phase that is miscible with the partitioned sample, and can therefore readily be detected and/or sorted using commercially available flow cytometers and fluorescence activated cell sorters (FACS). This allows for enrichments of target entities out of a sample that is not possible with other methods in which sorting is not easily accomplished.

In some embodiments, the disclosed methods can be used to quantitate nucleic acids in solution by counting the fraction of single or multiple emulsions that are fluorescent and undergo amplification and thus contain at least a single target nucleic acid, in most instances; false amplification may occur for stochastic reasons or, for example, the encapsulation of dust or other contaminants that interfere with the specificity of the amplification reaction. TaqMan® probes, molecular beacons, SYBR, and other kinds of detection components can also be included, allowing the use of multiple optical spectra for simultaneously detecting the amplification of different nucleic acid sequences in the target or due to multiple targets being encapsulated in the same monodisperse single-emulsion droplets, multiple-emulsion monodisperse droplets.

Like other PCR analysis methods, dPCR can be multiplexed using probes labeled with different fluorescent dyes.

Since dPCR acts on molecules in droplets, this provides unique measurement opportunities not possible with common methods, like the physical association of distinct sequences. This is valuable for a variety of important applications in genomic biology, including characterizing virus diversity, phasing microbial genomes, haplotyping cancer genomes, measuring mRNA splice forms, and characterizing length distributions of target molecules in solution.

In some embodiments, the disclosed methods and devices can be used to quantitate epitopes or detect proteins (including proteins on a virus or cell) in a sample using a digital ELISA procedure. In some embodiments, for example, epitopes bound to a solid substrate, such as a planer substrate surface or the surfaces of beads, can be additionally bound with an affinity reagent labeled with an enzyme catalyst. The sample can be washed to remove unbound affinity reagents and enzymes. The labeled epitopes or a portion thereof can then be released in solution in a variety of ways. For ease, the enzyme catalyst may be bound to the affinity reagent through a bond that can be degraded chemically or with the application, for example, of heat or light. Alternatively, the interaction between the affinity reagent and the epitope can be broken, or the interaction between the epitope and the substrate can be broken. If the binding occurs on beads, then the beads can be suspended in solution after the washing step, thereby suspending the enzyme catalysts. The suspended enzyme catalysts can then be encapsulated in the emulsions described herein, with reagents sufficient to detect the enzyme catalyst, such as a substrate that the enzyme catalyst can convert into a fluorescent product. The emulsions described herein can then be incubated under conditions suitable for catalysis, resulting in an emulsion containing a large amount of reaction product when the catalyst is present and a low amount when it is not. The number of fluorescent droplets can then be quantitated compared to the dim droplets, providing a measure of the number of catalyst molecules present in the sample. This information can then be used to infer the concentration of epitopes or proteins in the original sample.

Digital oligo-linked immunosorbent assays (dOLISA) are also contemplated herein. The methods described herein can be used for sensitive detection and absolute quantification of RNA molecules. Assay approaches of interest also include, but are not limited to, those described by Chang, et al., J. Immuno. Methods. 378(1-2), 102-15 (2012), the disclosure of which is incorporated herein by reference. This application is applied to extremely low concentrations of analytes and the binding characteristics can deviate from typical immunoassay or ELISA platforms. Theoretical analysis clarifies what performance metrics (detection sensitivity, assay speed, etc.) can be expected from a set of experimental parameters. The method involves binding of target protein molecules to antibodies conjugated to a bead surface. The amount of bound proteins (capture efficiency) in equilibrium state is determined by the dissociation constant KD, setting the upper bound for capture efficiency. The binding reaction is a dynamic process governed by the on and off rates (kon and kOff) and the time-dependent evolution of the system can be simulated by numerically solving the differential equation that describes the kinetics. Without the intention of being bound by any theory, the binding kinetics depends primarily on kon value while KD value has a negligible effect on it. The slow kinetics can be rescued if a higher concentration of antibodies can be provided for binding. In some embodiments, kon rate dictates the required duration of incubation to achieve desired detection efficiency. In the case of dOLISA, the secondary antibody is conjugated with a DNA oligo. The ternary complex (Ab-Ligand-oligoAb) is encapsulated into 0.1-10 million droplets, e.g., such that there are single DNA template molecules per droplet, droplet PCR amplification in the presence of a fluorogenic reagent is performed, and the fluorescent droplets are counted.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a conformation switching probe" includes a plurality of such conformation switching probes and reference to "the microfluidic device" includes reference to one or more microfluidic devices and equivalents thereof known to those skilled in the art, and so forth. It is further noted that the claims may be drafted to exclude any element, e.g., any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. This is intended to provide support for all such combinations.

Example 1

Digital Droplet PCR Accurately Quantifies
SARS-CoV-2 Viral Load from Crude Lysate
without Nucleic Acid Purification Accurate diagnostic testing for COVID-19 is essential, yet false negative results persist with current COVID-19 tests, particularly during early stages of infection prior to symptom onset (Kucirka, L. M., Lauer, S. A., Laeyendecker, O., Boon, D. & Lessler, J. Variation in False-Negative Rate of Reverse Transcriptase Polymerase Chain Reaction-Based SARS-CoV-2 Tests by Time Since Exposure. *Ann. Intern. Med.* (2020). doi:10.7326/m20-1495). In addition, SARS-CoV-2 viral load varies throughout an individual patient's disease course (Pan, Y., Zhang, D., Yang, P., Poon, L. L. M. & Wang, Q. Viral load of SARS-CoV-2 in clinical samples. *Lancet Infect. Dis.* 20, 411-412 (2020). Indeed, repeat testing of patient specimens can yield disparate viral loads without a change in clinical status, increasing the false negative rate and complicating patient management. Given the key role of diagnostic testing in guiding public health initiatives and strong relationship between viral load and transmissibility (Gandhi, M., Yokoe, D. S. & Havlir, D. V. Asymptomatic Transmission, the Achilles' Heel of Current Strategies to Control Covid-19. *N. Engl. J. Med.* (2020). doi:10.1056/nejme2009758), these observations underscore the importance of accurate approaches for SARS-CoV-2 quantification.

The gold standard for COVID-19 diagnosis is quantitative reverse transcriptase PCR (qRT-PCR) as recommended by the US Centers for Disease Control and Prevention (CDC) (Centers for Disease Control and Prevention. Real-time RT-PCR Panel for Detection 2019-nCoV. https://www.cdc.gov/coronavirus/2019-ncov/lab/rt-pcr-detection-instructions.html (2020)). Although robust in many settings (Mackay, I. M., Arden, K. E. & Nitsche, A. Real-time PCR in virology. Nucleic Acids Research 30, (2002)), qRT-PCR is limited by its reliance on a standard curve, sensitivity to inhibitors in clinical samples, and inconsistent performance at low concentrations. Furthermore, current COVID-19 qRT-PCR tests require multiple upstream processing steps, including sample collection, viral lysis, and RNA purification, a workflow limited by shortages in laboratory supplies and RNA extraction kits leading to bottle necks in COVID-19 testing. To mitigate these shortcomings, numerous tests are under development, including loop-mediated isothermal amplification (LAMP) (Lamb, L. E., Bartolone, S. N., Ward, E. & Chancellor, M. B. Rapid Detection of Novel Coronavirus (COVID-19) by Reverse Transcription-Loop-Mediated Isothermal Amplification. *medRxiv* 2020.02.19.20025155 (2020). doi:10.1101/2020.02.19.20025155, and Zhang, Y. et al. Rapid Molecular Detection of SARS-CoV-2 (COVID-19) Virus RNA Using Colorimetric LAMP. *medRxiv* 2, 2020.02.26.20028373 (2020)) and CRISPR-based assays (Broughton, J. P. et al. CRISPR-Cas12-based detection of SARS-CoV-2. *Nat. Biotechnol.* 1-5 (2020). doi:10.1038/s41587-020-0513-4, and Kellner, M. J., Koob, J. G., Gootenberg, J. S., Abudayyeh, O. O. & Zhang, F. SHERLOCK: nucleic acid detection with CRISPR nucleases. *Nat. Protoc.* 14, 2986-3012 (2019)). Although promising, these methods generally require upfront nucleic acid purification. Experimental approaches attempt to analyze crude lysate directly (Ladha, A. et al. A 5-min RNA preparation method for COVID-19 detection with RT-qPCR. *medRxiv* (2020). doi:10.1101/2020.05.07.20055947, and Joung, J. et al. Point-of-care testing for COVID-19 using SHERLOCK diagnostics. *medRxiv* (2020). doi:10.1101/2020.05.04.20091231), but the resulting viral load measurements are not quantitative and overall assay performance remains unknown. Thus, a robust method to quantify SARS-CoV-2 viral load directly from crude lysate would both simplify testing and provide additional information to potentially guide clinical management.

As shown herein, digital droplet PCR (ddPCR) enables accurate SARS-CoV-2 RNA quantification from viral lysate without nucleic acid purification. It provides absolute viral counts from crude lysate, obviating the need for a standard curve while being resistant to reaction inhibition. In addition, it was found that ddPCR, but not qRT-PCR, yields accurate measurement of SARS-CoV-2 viral load when applied directly to crude lysate without RNA extraction. In addition, ddPCR from crude lysate provides comparable viral load estimates to qRT-PCR from purified nucleic acid. Finally, ddPCR detects SARS-CoV-2 RNA in a clinically suspicious case negative by conventional qRT-PCR. Taken together, these data indicate that ddPCR robustly quantifies SARS-CoV-2 RNA from crude viral lysate, thus representing a complementary approach to conventional qRT-PCR in clinically ambiguous scenarios where ultra-high sensitivity is needed or when RNA purification cannot be incorporated within the diagnostic workflow.

Materials and Methods

SARS-CoV-2 quantitative reverse transcriptase polymerase chain reaction. N1 and N2 nucleocapsid primers from the CDC assay were obtained from Integrated DNA Technologies (IDT). For primer sequences, please see https://www.cdc.gov/coronavirus/2019-ncov/downloads/rt-pcr-panel-primer-probes.pdf. PCR cycling conditions including reverse transcription were run per the CDC EUA-approved protocol with the Promega GoTaq Probe 1-Step RT-qPCR system (Catalog #A6120). In brief, a 20 µL reaction comprising 10 µL GoTaq, 0.4 µL GoScript, 1.5 µL primer master mix, 3.1 µL water, and 5 µL input RNA (or crude lysate) was reverse transcribed by incubating at 45° C. for 15 minutes followed by 95° C. for 2 minutes per CDC protocol. The reaction was then thermocycled for 45 cycles of 95° C. for 20 seconds (denaturation) and 55° C. for 30 seconds (annealing) on either the ABI 7500 Fast DX (Applied Biosystems) or the QuantStudio 5 Real-Time PCR System (Thermo Fisher).

Digital droplet polymerase chain reaction. The N1 nucleocapsid primers from the CDC assay were used for all ddPCR data with the 1-step RT-ddPCR Advanced Kit for Probes (Bio-Rad Catalog #1864022). In brief, a 20 µL reaction comprising 2 µL reverse transcriptase, 1 µL DTT, 1.5 L primer master mix, 5.5 µL water, and 5 µL input RNA (or crude lysate) was used for each sample. Droplets were generated with the QX200 Droplet Digital PCR System (Bio-Rad), sealed, and reverse transcription was performed by incubating at 50° C. for 60 minutes followed by 95° C. for 10 minutes per manufacturer's protocol. The reaction was then thermocycled with the same conditions as used for the CDC EUA-approved bulk qRT-PCR assay described above, and then read with the QX200 Droplet Reader (Bio-Rad) with thresholds between positive and negative drops set by QuantaSoft Software and confirmed by manual inspection. For qualitative assessment of fluorescence, thermocycled drops were imaged using the EVOS Cell Imaging System (Thermo Fisher).

SARS-CoV-2 RNA and viral standard preparation. In vitro transcribed SARS-CoV-2 RNA standards obtained from Twist biosciences (Catalog #102916) were used for standard curve calculation across qRT-PCR and ddPCR. Replication defective virus was obtained from Seracare via the AccuPlex SARS-CoV-2 Reference Material Kit (Catalog #0505-0126), and purified RNA was generated from these standards with the Qiagen DSP Viral RNA Mini Kit (Catalog #61904) as described in the CDC EUA approved protocol. For crude lysate, samples were processed either using the QuickExtract lysis buffer (Lucigen Catalog #QE09050) as previously described (Ladha, A. et al. *medRxiv* (2020). doi:10.1101/2020.05.07.20055947) simply heated for 5 minutes at 95° C., or added directly to UTM for downstream analysis.

Human nasopharyngeal swab sample collection and preparation from COVID positive patients. Clinical nasopharyngeal swab samples from patients infected with SARS-CoV-2 were collected in UTM and acquired by the Chiu laboratory with approval of the University of California San Francisco (UCSF) Institutional Review Board. The approved study was a no-subject contact bio-banking protocol using remnant clinical samples with waiver of consent. RNA purification and crude lysis extraction was performed as described above. For qRT-PCR from purified RNA, samples were diluted 1:4 given they were concentrated two-fold during purification and not mixed 1:1 with Quick Extract buffer in order to provide direct comparison to crude lysis conditions. Of the 33 original clinical samples obtained for analysis, 32 had sufficient material for qRT-PCR from both purified RNA and crude lysate while 22 had sufficient material for adequate dropmaking and subsequent comparison across all three assays (qRT-PCR from purified RNA, qRT-PCR from crude lysate, and ddPCR from crude lysate).

Results

Digital droplet PCR quantifies target nucleic acid sequences using many partitioned reactions. In contrast to qRT-PCR, in which concentrations are inferred from amplification rates relative to a standard curve, ddPCR cycles the sample to endpoint, after which target molecules are counted directly by enumerating positive droplets. This approach provides several advantages over qRT-PCR, including more precise measurements and absolute quantification without the need for a standard curve (Vogelstein, B. & Kinzler, K. W. Digital PCR. *Proc. Natl. Acad. Sci. U.S.A* 96, 9236-9241 (1999), and Kuypers, J. & Jerome, K. R. Applications of digital PCR for clinical microbiology. *Journal of Clinical Microbiology* 55, 1621-1628 (2017)). Moreover, ddPCR can detect a variety of viral pathogens including human immunodeficiency virus (HIV) (Strain, M. C. et al. Highly Precise Measurement of HIV DNA by Droplet Digital PCR. *PLoS One* 8, e55943 (2013)), cytomegalovirus (CMV) (Sedlak, R. H., Cook, L., Cheng, A., Magaret, A. & Jerome, K. R. Clinical Utility of Droplet Digital PCR for Human Cytomegalovirus. *J. Clin. Microbiol.* (2014). doi:10.1128/ JCM.00803-14), and human herpes virus 6 (HHV-6) (Sedlak, R. H. et al. Clin. Chem. 60, 765-772 (2014)). In COVID-19 patients, ddPCR of purified RNA extracts demonstrates advantages for diagnosis and monitoring, particularly in patients exhibiting low viral load (Yu, F. et al. *Clin. Infect. Dis.* (2020). doi:10.1093/cid/ciaa345; Suo, T. et al. *medRxiv* 2020.02.29.20029439 (2020). doi:10.1101/ 2020.02.29.20029439; and Dong, L. et al. *medRxiv* (2020)). Although recent studies suggest ddPCR may be resistant to lysate-based inhibition Hu, Y., Xu, P., Luo, J., He, H. & Du, W. Anal. Chem. 89, 745-750 (2017)), fidelity from crude viral lysate without RNA extraction for SARS-CoV-2 viral load quantification remains unknown.

The performance of conventional qRT-PCR and ddPCR was compared for SARS-CoV-2 detection (FIG. 1). The standard qRT-PCR workflow for SARS-CoV-2 testing requires sample collection via nasopharyngeal swab, placement of swabs into sterile tubes containing universal transport medium (UTM), and nucleic acid extraction to obtain purified RNA free of PCR inhibitors (FIG. 1, top workflow). The subsequent qRT-PCR result is thus critically dependent on the amount and quality of template RNA extracted, potentially resulting in false negatives at low input viral copy numbers. A simpler approach would be to omit the RNA extraction step, thus performing quantification directly on cell lysate. However, inhibitors present in unpurified cell lysate decrease reaction efficiency and interfere with accurate quantification, potentially leading to false negatives. ddPCR can circumvent this shortcoming by partitioning the target nucleic acid and sequestering inhibitory molecules in separate droplets, permitting normal reaction kinetics and accurate viral quantification (FIG. 1, bottom workflow). From a practical perspective, such an approach would simplify the overall workflow and obviate the need for a standard curve.

Figure 2F:
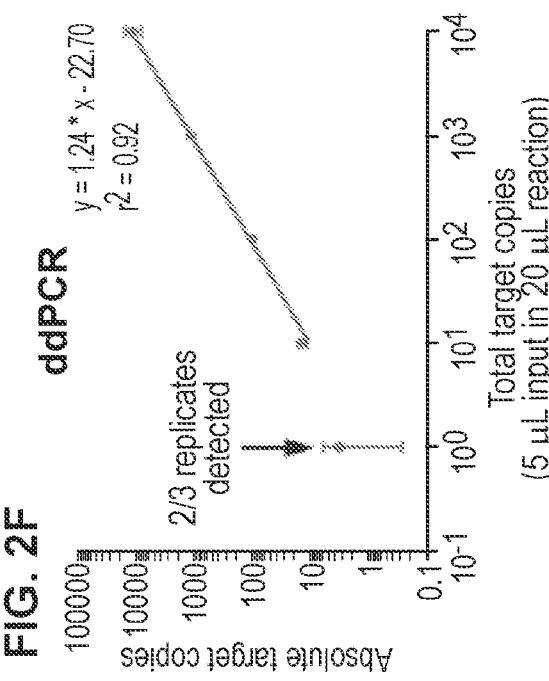
FIG. 2 shows that Digital droplet PCR (ddPCR) reliably quantifies SARS-CoV-2 RNA standards.
(FIG. 2A) Fluorescence microscopy images of ddPCR using CDC N1 primer set with 1000 input copies of SARS-CoV-2 RNA and (FIG. 2B) no template control.
(FIG. 2C) Fluorescence intensities as measured by BioRad QX200 Droplet Reader for 10,000 input target copies and (FIG. 2D) no template control.
(FIG. 2E) Quantitative reverse transcription PCR (qRT-PCR) standard curve using CDC N1 primer set and SARS-CoV-2 RNA shows expected linear relationship between input viral copy number and cycle threshold (Ct) value with an estimated limit of detection (LoD) of 10 copies per reaction. (f) ddPCR standard curve for SARS-CoV-2 RNA reveals accurate viral copy number measurement with an estimated LoD of 10 copies per reaction.
Figure 2E:
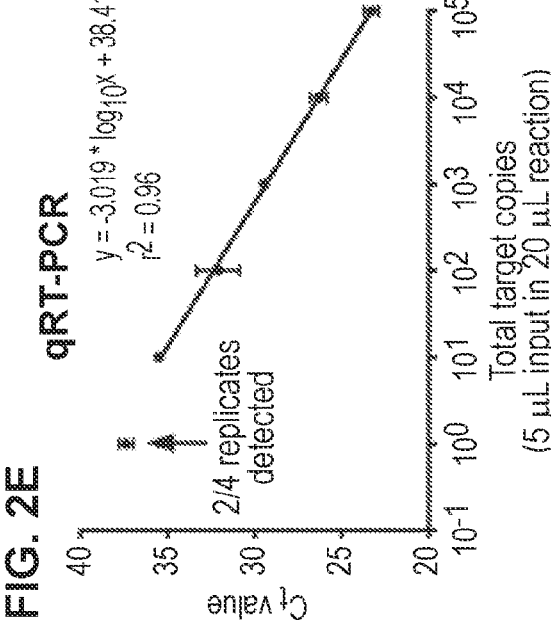

The nucleocapsid N1 primer was used in the CDC qRT-PCR assay for ddPCR and the ddPCR assay was used on purified, in vitro transcribed SARS-CoV-2 RNA standards (Twist Biosciences, Catalog #102916). Visualization of droplet fluorescence reveals a clear qualitative difference between positive and negative drops (FIG. 2*a*) with minimal background fluorescence with a no template control (FIG. 2*b*). Quantitative analysis of fluorescence intensity similarly shows clear separation with an approximately two-fold increase in fluorescence of positive compared to negative drops (FIG. 2*c*), again with minimal false positives in the no-template control (FIG. 2*d*). To confirm the linearity and dynamical range of ddPCR, SARS-CoV-2 RNA standards analyzed by conventional qRT-PCR (FIG. 2*e*) versus ddPCR (FIG. 2*f*) was compared. Both bulk qRT-PCR ($r^2$=0.96) and ddPCR ($r^2$=0.92) robustly quantify input RNA across the tested range and exhibit similar limits of detection at 10 copies per reaction, consistent with published reports (Yu, F. et al. *Clin. Infect. Dis.* (2020). doi:10.1093/cid/ciaa345; Suo, T. et al. *medRxiv* 2020.02.29.20029439 (2020). doi:10.1101/ 2020.02.29.20029439; and Dong, L. et al. *medRxiv* (2020)).

Figures 3A, 3B, 3C, 3D:
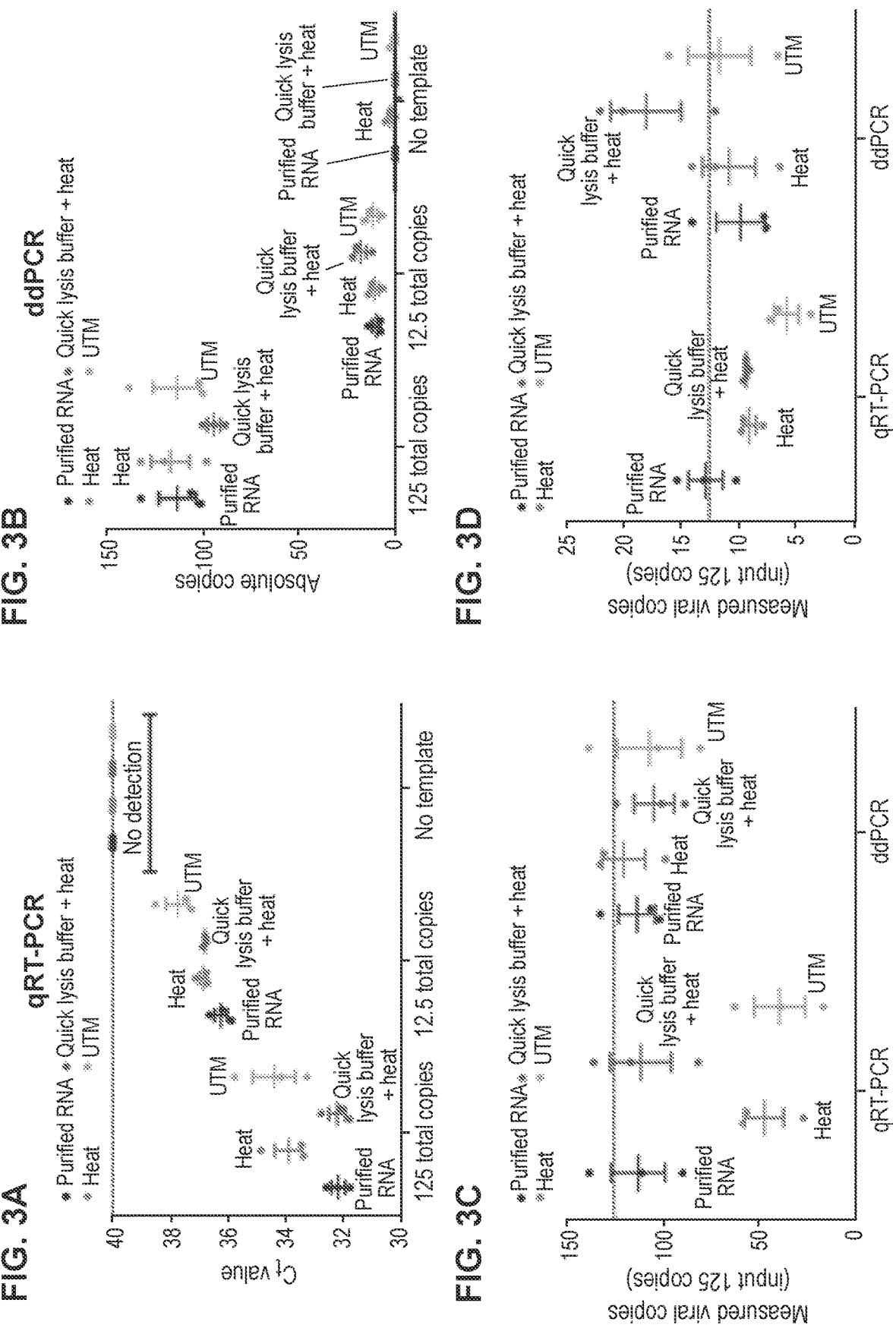
(FIG. 3A) Quantitative reverse transcription PCR (qRT-PCR) of Serocare SARS-CoV-2 viral standards across lysis conditions reveals decreased PCR efficiency at low copy numbers and in presence of universal transport medium (UTM).
(FIG. 3B) ddPCR of Serocare SARS-CoV-2 viral standards across lysis conditions reveals accurate viral load quantification across all tested conditions.
(FIG. 3C) Comparison of relative quantification by qRT-PCR and absolute quantification by ddPCR at 125 input copies and (FIG. 3D) 12.5 input copies shows decreased viral load measurements by qRT-PCR in the presence of UTM.

Unlike purified standards, crude lysate from patient samples contains target viral nucleic acids mixed with numerous inhibitory molecules. Thus, novel approaches aiming to directly analyze patient samples without nucleic acid purification implement lysis strategies, such as heating input samples or utilizing extraction buffers that stabilize reaction enzymes and neutralize inhibitors. To determine how such workflows impact assay performance, qRT-PCR and ddPCR quantification of SeraCare SARS-CoV-2 viral standards was compared using three crude lysis workflows without RNA purification: (1) incubation at 95° C. for 5 minutes only (heat lysis), (2) addition of QuickExtract buffer in a 1:1; ratio followed by incubation at 95° C. for five minutes, or (3) directly from UTM. Conventional qRT-PCR detects SeraCare SARS-CoV-2 standards across all three crude lysis conditions as well as purified RNA at both 125 and 12.5 input copies per reaction using an assay cycle threshold ($C_t$) of less than 40 per CDC recommendations (FIG. 3*a*). However, increased $C_t$ values were observed for all tested crude lysate conditions in the absence of upfront RNA purification except for QuickExtract buffer at 125 input copies, suggesting decreased efficiency when amplifying template from crude lysate by qRT-PCR. In contrast, ddPCR accurately and reproducibly quantifies input viral copy number across all conditions (FIG. 3*b*). Intriguingly, UTM inhibits bulk qRT-PCR but does not affect ddPCR, suggesting ddPCR may be useful for retrospective analysis of patient samples stored in UTM. No false positives are present in the QuickExtract buffer samples analyzed by ddPCR, suggesting adequate digestion of background nucleic acid. When compared to estimated SARS-CoV-2 viral load by relative quantification from qRT-PCR standard curves, ddPCR offers more accurate viral load measurement both at 125 input copies per reaction (FIG. 3*c*) and 12.5 input copies per reaction (FIG. 3*d*). Taken together, this shows that ddPCR, but not qRT-PCR, accurately quantifies SARS-CoV-2 viral load from crude lysate without RNA purification at low input copy numbers and in the presence of UTM.

Figures 4C, 4D:
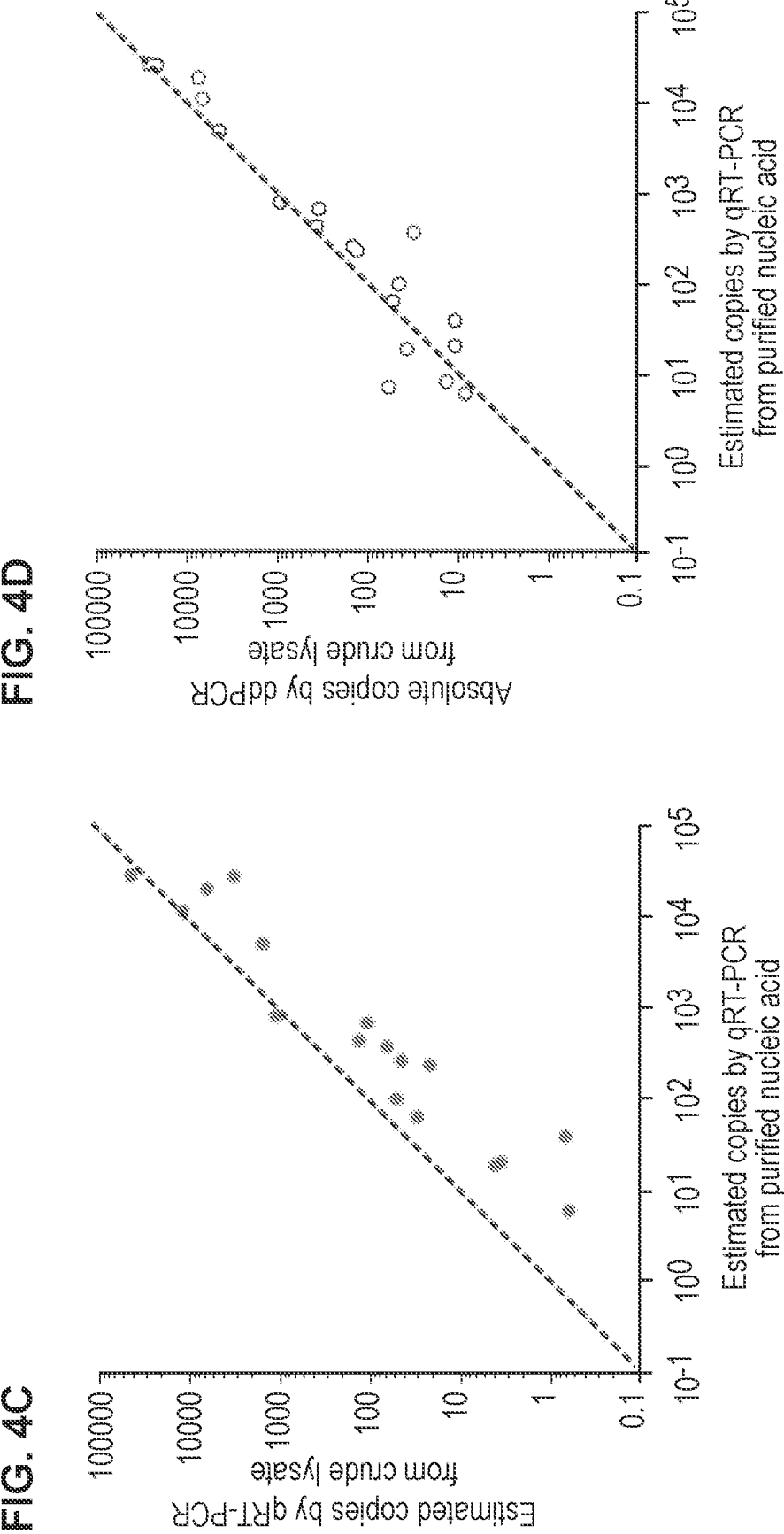
(FIG. 4C) Relative quantification of viral load by qRT-PCR from purified RNA versus crude lysate demonstrates systematic underestimation of viral load.
(FIG. 4D) Absolute quantification of viral load by ddPCR from crude lysate shows strong correlation with relative quantification by qRT-PCR from purified RNA. In panels (FIG. 4C) and (FIG. 4D), graphed y=x line provides a reference for perfect agreement between the two assays. All crude lysis was carried out via 1:1 dilution QuickExtract buffer followed by heating at 95° C. for 5 minutes as described in text.

To evaluate both qRT-PCR and ddPCR methods for SARS-CoV-2 RNA quantification from patient samples collected by nasopharyngeal swab and stored in UTM, 33 clinical specimens collected from patients suspected of having COVID-19 were tested. When comparing qRT-PCR from purified RNA versus crude lysate, the Ct values obtained following amplification from crude lysis are consistently increased compared to Ct values from purified RNA, suggesting decreased reaction efficiency and subsequently, inaccurate estimate of viral load, from crude lysate (FIG. 4*a*). In contrast, absolute quantification of SARS-CoV-2 viral load by ddPCR from crude lysate shows consistency with relative quantification by qRT-PCR from purified RNA rather than viral load estimates obtained by qRT-PCR from crude lysate (FIG. 4*b*). Direct inspection of fluorescence intensities confirms clear separation between positive and negative drops in patient samples without false positives in the no-template control, consistent with robust detection by ddPCR. Finally relative quantification by qRT-PCR directly from crude lysate, while positively correlated with measurements from purified RNA, consistently underestimates SARS-CoV-2 viral load in clinical patient samples and, moreover, fails to amplify any viral sequences from patients 5 and 8 (FIG. 4*c*). In contrast, absolute quantification by ddPCR demonstrates strong correlation with estimates from qRT-PCR performed from purified RNA, highlighting the improved assay fidelity with ddPCR compared to qRT-PCR when working from crude lysate. In sum, ddPCR demonstrates better correlation with the current gold standard of qRT-PCR from purified RNA for quantitation of SARS-CoV-2 viral load.

Conclusions

The COVID-19 pandemic underscores the importance of diagnostic testing for novel pathogens with assays that minimize sample processing and reagent requirements while maintaining accuracy. Here, it is shown that ddPCR allows accurate SARS-CoV-2 quantification from crude lysate while conventional bulk qRT-PCR, the current gold standard, appears more sensitive to inhibition. When analyzing crude lysate from patient samples, the result is higher rates of false negatives by qRT-PCR with viral loads near the limit of detection. In contrast, ddPCR is robust to inhibition and accurately quantifies viral load without nucleic acid purification. While the clinical relevance of patients harboring virus at low titers with $C_t$ values >36 remains unclear, robust detection of such individuals may facilitate identification of asymptomatic spreaders, monitoring disease progression, and evaluating the efficacy of antiviral therapy.

While these results are consistent with previous reports that ddPCR is more resistant to reaction inhibition than bulk qPCR (Hu, Y., Xu, P., Luo, J., He, H. & Du, W. *Anal. Chem.* 89, 745-750 (2017)), the underlying mechanism remains poorly understood. Sequestration of inhibitors in empty droplets facilitates may thus lead to more efficient PCR amplification in droplets containing template. In this scenario, the fidelity of droplet assays in crude lysate would likely be independent of the specific molecular biology used for nucleic acid detection, and thus, such resistance to inhibition may extend to other assays such as isothermal and CRISPR-based target detection. Indeed, droplet LAMP for influenza exhibits increased resistance to reaction inhibition (Hu, Y., Xu, P., Luo, J., He, H. & Du, W. *Anal. Chem.* 89, 745-750 (2017)).

Detection of low titer SARS-CoV-2 RNA by ddPCR in patients negative by the 'gold standard' clinical qRT-PCR assay raises a potential concern of false positive results. While current qRT-PCR COVID-19 testing appears prone to false negatives (Li, Y. et al. *Med. Virol.* (2020). doi:10.1002/jmv.25786; Xiao, A. T., Tong, Y. X. & Zhang, S. J. *Med. Virol.* (2020). doi:10.1002/jmv.25855; Ai, T. et al. *Radiology* 200642 (2020). doi:10.1148/radiol.2020200642; and West, C. P., Montori, V. M. & Sampathkumar, P. *Mayo Clin. Proc.* (2020). doi:10.1016/j.mayocp.2020.04.004), it nevertheless remains possible ddPCR demonstrates the opposite predilection for false positives. This was controlled by including bona fide no template controls for all assay runs. Furthermore, the finding of similar limit of detection but improved precision with ddPCR compared to qRT-PCR is consistent with prior work in cancer (Hindson, C. M. et al. *Nat. Methods* 10, 1003-1005 (2013)). Importantly, comparison of ddPCR to qRT-PCR from purified nucleic acid extracts in larger COVID-19 patient cohorts similarly demonstrates detection of SARS-CoV-2 RNA by ddPCR in patients negative by qRT-PCR (Suo, T. et al. *medRxiv* 2020.02.29.20029439 (2020). doi:10.1101/2020.02.29.20029439; Dong, L. et al. *medRxiv* (2020)).

The present disclosure highlights the potential advantages of ddPCR for SARS-CoV-2 RNA detection from clinical samples, particularly to obtain quantitative results from crude lysate, thus obviating the need for nucleic acid purification. Taken together, the present data support the role of ddPCR as a potential alternative to bulk qPCR in settings requiring nucleic acid quantification at low input copy numbers without upfront nucleic acid extraction.

Example 2

Digital Droplet LAMP Assay for the Detection of SARS-CoV-2

This Example describes materials and methods for using a ddLAMP assay for the detection of SARS-CoV-2.

Figure 5:
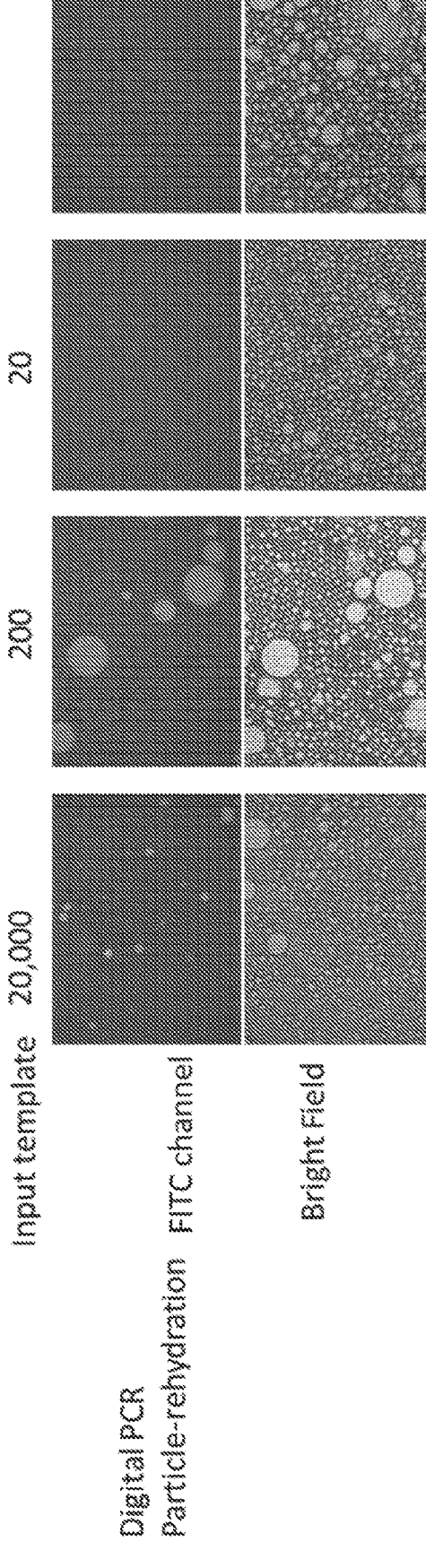
FIG. 5 shows that the droplet digital PCR assay can specifically detect SARS-COV-2 and the number of positive droplets correlates with the input template amount.

Polyacrylamide beads from Bio-Rad with an average diameter of 60 um were re-hydrated and washed with $H_2O$, and the amount of beads was used to replace the volume of H2O in the 20 μL of CDC PCR assay. The primer/probes for the PCR assay were specifically targeting the N gene of SARS-COV-2, and serial diluted SARS-COV-2 DNA was used as the template. After incubate the reagents with beads for 5 min, the beads were spun down at 1000 g for 1 min and the supernatant was removed. 100 μl of HFE containing 2% surfactant (2% (w/w) PEG-PFPE amphiphilic blockcopolymer surfactant (008-Fluoro-surfactant, RAN Biotech-nologies)) was then added to each reaction, and then shaken by vortexing for 1 min. The emulsion was formed and the bottom oil was replaced by 45 μl of FC40 containing 5% surfactant. The reaction was taken place in the thermocycler with the following program: 95 C 3 min, 95° C. 20 s, 55° C. 30 s, go to step 2 for 45 cycles. After thermocycling, the emulsions were transferred to slides for imaging. Fluorescence and bright field images were taken by EVOS microscope. The data showed that the droplet digital PCR assay can specifically detect SARS-COV-2 and the number of positive droplets correlates with the input template amount (FIG. 5).

Figure 6:
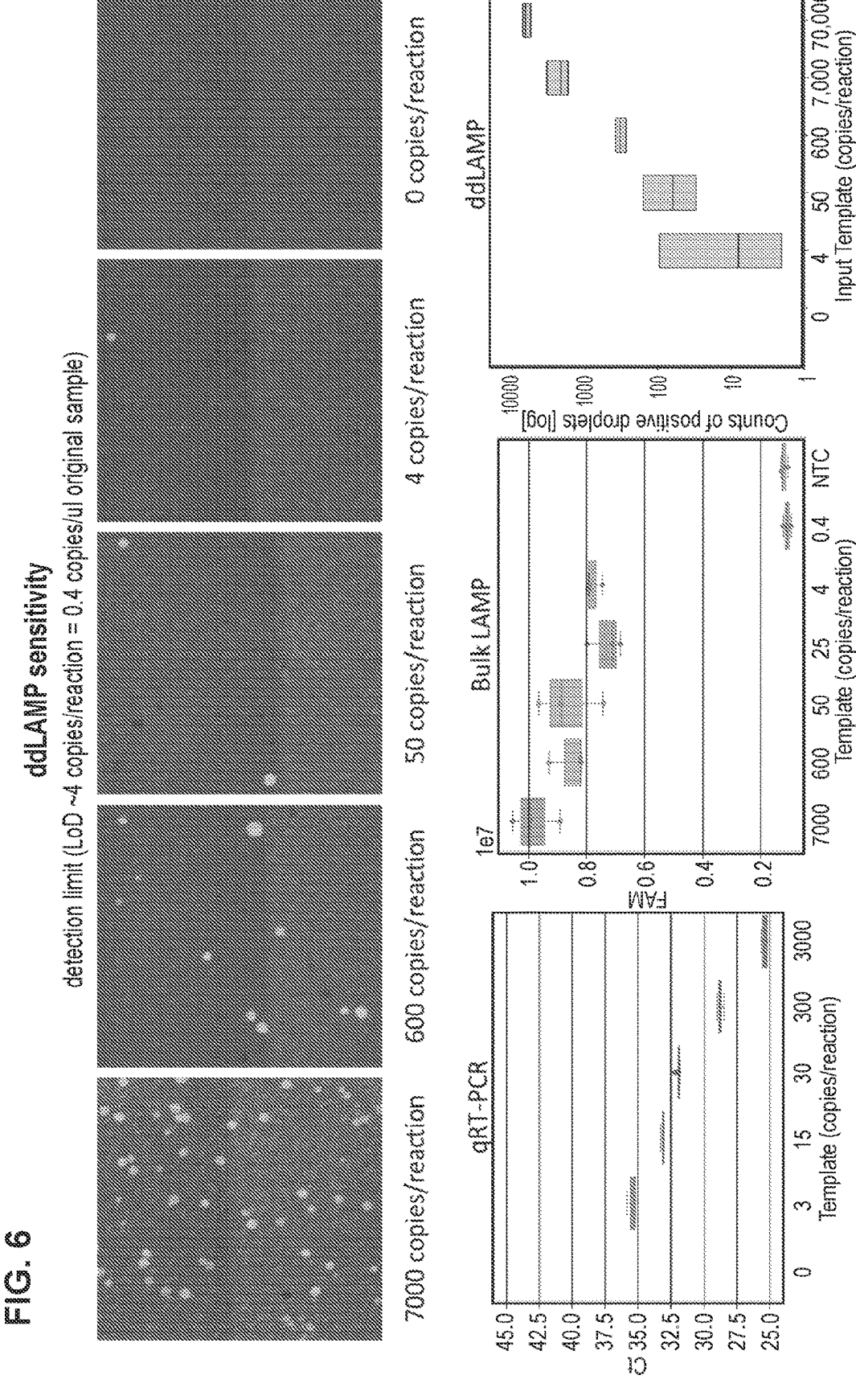
FIG. 6 shows that the ddLAMP assay has equivalent detection sensitivity to qRT-PCR and bulk LAMP with the Limit of detection of 4 copies/reaction.

Next, a 25 μL LAMP assay containing FAM labeled primers specifically targeting the N gene of SARS-COV-2 was performed with the template of serial diluted SARS-COV-2 RNA, respectively. 100 ul of HFE containing 2% surfactant was then added to each reaction, and then shaken by hand up and down for 30 s. The emulsion was formed and the bottom oil was replaced by 45 µl of FC40 containing 5% surfactant. The reaction was taken place in the 65 C incubator for 30 min and cooled to room temperature for 5 min before imaging. Fluorescence images were taken by EVOS microscope. The same serial diluted templates were also used for qRT-PCR and bulk LAMP. The data showed that the ddLAMP assay has equivalent detection sensitivity to qRT-PCR and bulk LAMP with the Limit of detection of 4 copies/reaction (FIG. 6).

Figure 7:
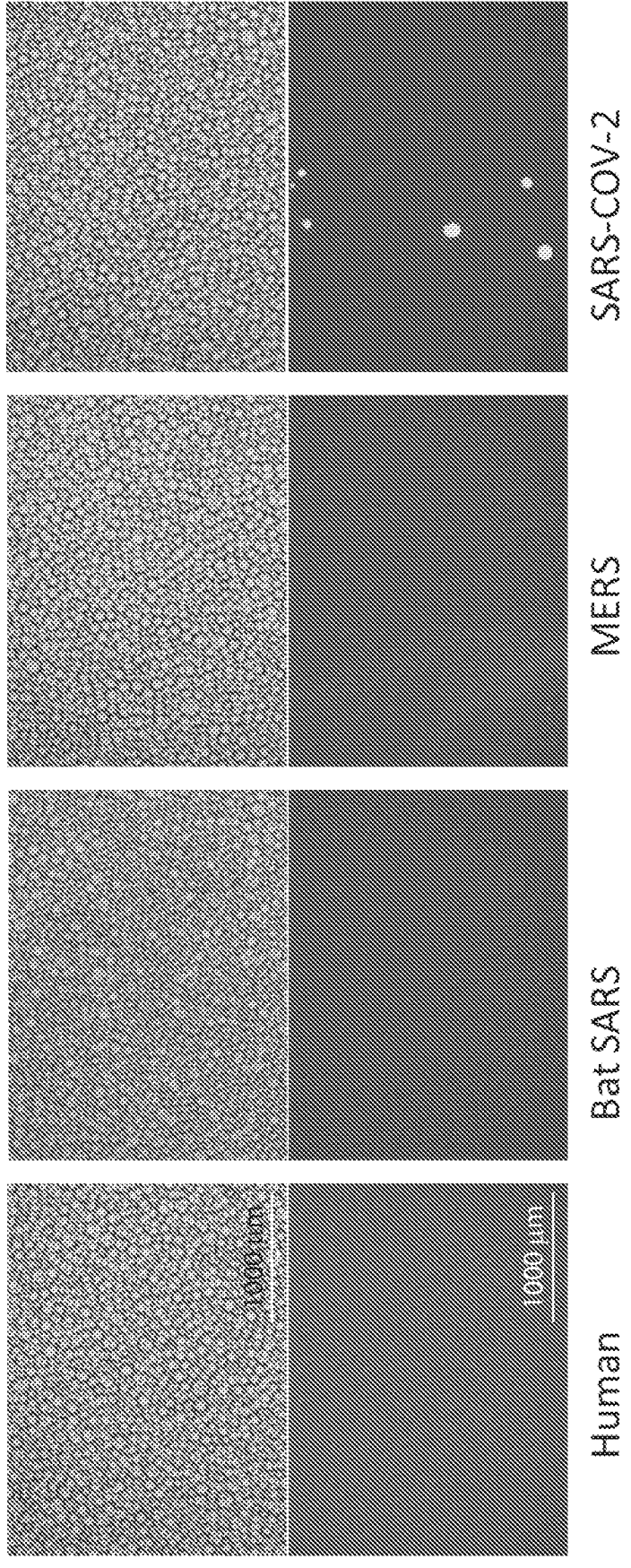
FIG. 7 shows the LAMP assay can specifically detect SARS-COV-2 but not other templates.

Finally, a 25 µL LAMP assay containing FAM labeled primers specifically targeting the N gene of SARS-COV-2 was performed with the template of human DNA, bat sourced SARS DNA, MERS DNA and SARS-COV-2 RNA, respectively. Then 100 µl of HFE containing 2% surfactant was added to each reaction, and then shaken by hand up and down for 30 s. The emulsion was formed and the bottom oil was replaced by 45 µl of FC40 containing 5% surfactant. The reaction was taken place in the 65 C incubator for 30 min and cooled to room temperature for 5 min before imaging. Fluorescence and bright field images were taken by EVOS microscope. The data showed that the LAMP assay can specifically detect SARS-COV-2 but not other templates (FIG. 7).

Example 3

Expanding the Dynamic Range of the Digital Assay by Mixing Various Sized Droplets By combining different partitioning of various sizes (reagent volumes, a broader range of assay sensitivities can be achieved. The total number of partitions could be reduced thus reduce the readout time and increase the throughput of digital assays.

This Example describes a simulation of a digital assay dynamic range by mixing various sized droplets.
Simulation Setup 2 different sized droplets (120 um diameters as large, and 50 um diameters as small) are generated and the percentage of the total volume of small droplets ranges from 0 to 1 (small/large).

A fixed imaging window was used to image the droplets.
Droplet Counts Calculation The volume of the droplet based on the volume is calculated using Eq1:

$$V_{droplet} = \frac{4}{3}\pi\left(\frac{d_{droplet}}{2}\right)^3 \qquad \text{(Eq 1)}$$

In this simulation $d_{small}$=50 and $d_{large}$=120.

Assume the small droplets take $P_{small}$ (Percentage) of the total volume of all droplets, thus the volume percentage of large droplets is $P_{large}$=1−$P_{small}$.

The droplet count ratio between small and large droplets are calculated as in Eq2:

$$R_{small/large} = \frac{P_{small}/V_{droplet\_large}}{(1-P_{small})/V_{droplet\_small}} \qquad \text{(Eq 2)}$$

The area taken by each droplet in the imaging window is calculated with Eq3:

$$A_{droplet} = \pi\left(\frac{d_{droplet}}{2}\right)^2 \qquad \text{(Eq 3)}$$

The total area of the imaging window is $A_{total}$=1 cm² (or $10^8$ um²). Assume the droplet are tightly packed without space in between, the counts of small and large droplets ($n_{small}$ and $n_{large}$) are:

$$n_{small} = \left\lfloor \frac{A_{total}/(1 + 1/R_{small/large})}{A_{droplet\_small}\left(\frac{d_{large}}{d_{small}}\right)^2} \right\rfloor, \text{ and} \qquad \text{(Eq 4)}$$

$$n_{large} = \left\lfloor \frac{A_{total}/(1 + R_{small/large})}{A_{droplet\_large}\left(\frac{d_{small}}{d_{large}}\right)^2} \right\rfloor, \text{ for } P_{small} \neq 0 \text{ or } 1;$$

$$n_{small} = \left\lfloor \frac{A_{total}}{A_{droplet\_small}} \right\rfloor, \text{ and } n_{large} = 0, \text{ for } P_{small} = 1;$$

$$n_{small} = 0, \text{ and } n_{large} = \left\lfloor \frac{A_{total}}{A_{droplet\_large}} \right\rfloor, \text{ for } P_{small} = 0$$

Poisson Statistics for Digital Assay

In digital assays, the molecules are distributed into a large number of partitions such as droplet in a way that each partition has a number of molecules (n=0, 1, 2, 3 or more) following a Poisson distribution:

$$Pr(n) = \frac{\lambda^n e^{-\lambda}}{n!}, \qquad \text{(Eq 5)}$$

where Pr(n) is the probability that a droplet contain n copy of molecules and the mean number of molecules per droplet is X.

PCR reaction on those partitions generate signals in the partitions containing one or more molecules (positive) and no signals in those partitions contain zero molecules (negative). The mean number of negative partitions is:

$$Pr(0) = e^{-\lambda} = \frac{N_{neg}}{N_{total}} \qquad \text{(Eq 6)}$$

The concentration of the target molecules can be calculated:

$$C = \frac{\lambda}{V_{droplet}} = \frac{-\ln\left(\frac{N_{neg}}{N_{total}}\right)}{V_{droplet}} \qquad \text{(Eq 7)}$$

The dynamic range (R) of the digital assay is the detectable concentration in $\log_{10}$ units:

$$R = \log_{10}\frac{\lambda_u}{\lambda_l} \qquad \text{(Eq 8)}$$

The lower and upper detection limits $\lambda_l$ and $\lambda_u$ are determined by the detection precision requirement.

Precision is defined as the relative spread of the confidence interval around $\lambda$ compared to the true value of $\lambda$:

$$P = \frac{\max(|\lambda - \lambda_{CI_u}|, |\lambda_{CI_l} - \lambda|)}{\lambda} \quad \text{(Eq 9)}$$

For a 95% confident interval, the confidence interval around $\lambda$ is calculated as follows:

$$\lambda_{CI_u} = \lambda * e^{-1.96\frac{\sqrt{e^\lambda - 1}}{\lambda\sqrt{n}}} \quad \text{(Eq 10)}$$

$$\lambda_{CI_l} = \lambda * e^{1.96\frac{\sqrt{e^\lambda - 1}}{\lambda\sqrt{n}}} \quad \text{(Eq 11)}$$

Substituting Eq 10 and Eq 11 into Eq 9 produce the precision expression:

$$P = \frac{\max\left(\left|\lambda - \lambda * e^{-1.96\frac{\sqrt{e^\lambda - 1}}{\lambda\sqrt{n}}}\right|, \left|\lambda * e^{1.96\frac{\sqrt{e^\lambda - 1}}{\lambda\sqrt{n}}} - \lambda\right|\right)}{\lambda} = \quad \text{(Eq 11)}$$

$$\max\left(\left|1 - e^{\pm 1.96\frac{\sqrt{e^\lambda - 1}}{\lambda\sqrt{n}}}\right|\right)$$

Simulation to Find the Best Mixing Ratio of Two Sized Droplets

A python program was written according to the equations listed above for simulation. 2 different sized droplets (120 um diameters as large, and 50 um diameters as small) were simulated and the percentage of the total volume of small droplets ranges from 0 to 1 (small/large).

The droplets were analyzed in a imaging window of 1 cm^2.

The precision was set to be 20%.

Figure 8:
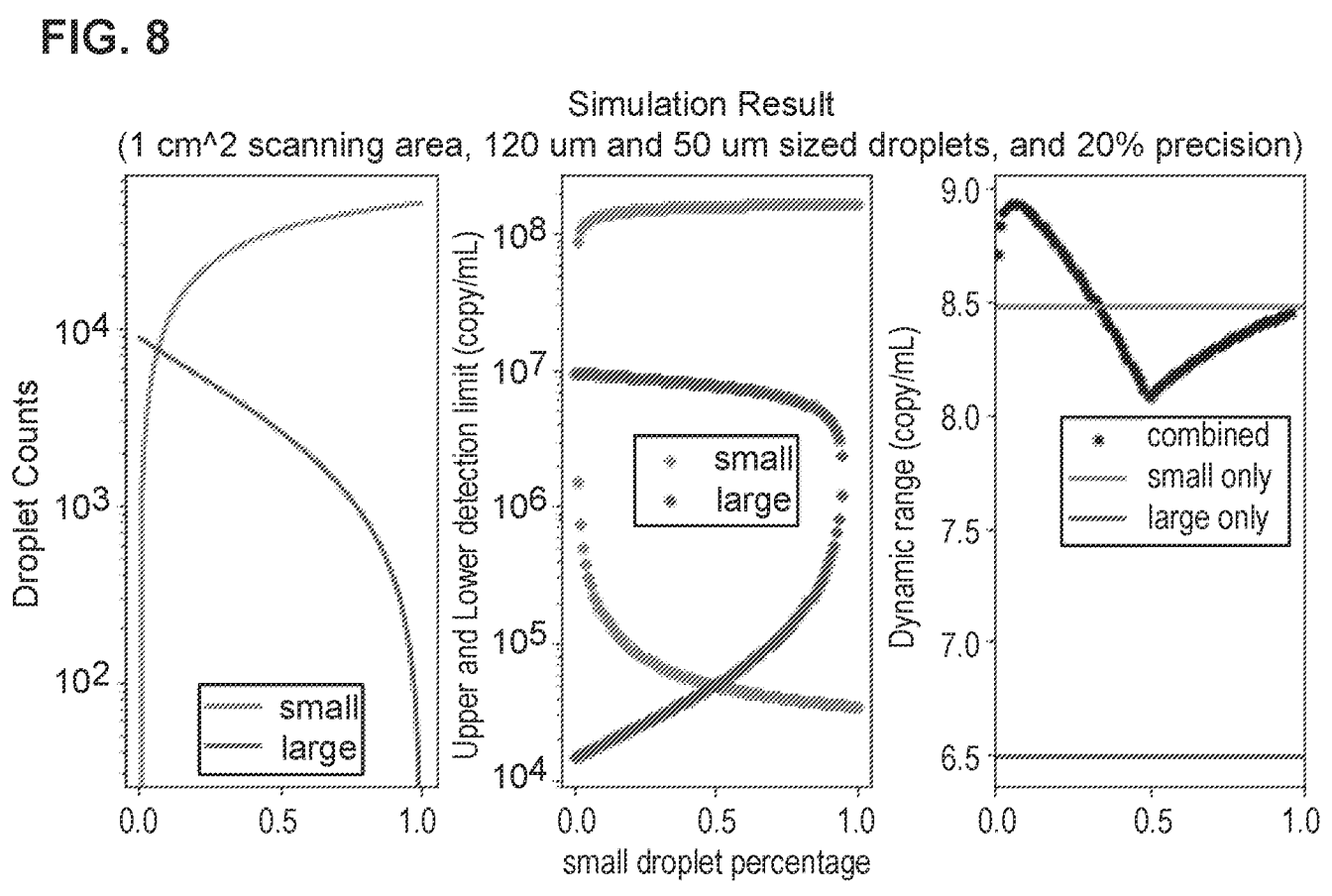

The simulation result is shown in FIG. 8. When the droplets are mixed with 7% 50 um droplets and 93% 120 um droplets, the widest dynamic range is achieved.

Example 4

Bulk Readouts from Digital Assays

Digital assays/reactions such as those described herein are preferable because of their high sensitivity. However, readouts from digital reactions usually require additional methods that can detect each individual reaction separately. The present Example describes a method of using qPCR as a readout for ddPCR. Other than qPCR, other bulk readout methods can also be applied including, but not limited to, a bioanalyzer to quantify ddPCR amplicons, and a fluorescent plate reader to quantify total fluorescence form ddPCR. Another presented Example describes a method of using a bioanalyzer (gel electrophoresis) as readout for ddLAMP. Other than bioanalyzer, other bulk readout method can also be applied including, but not limited to, qPCR.

Figure 9:
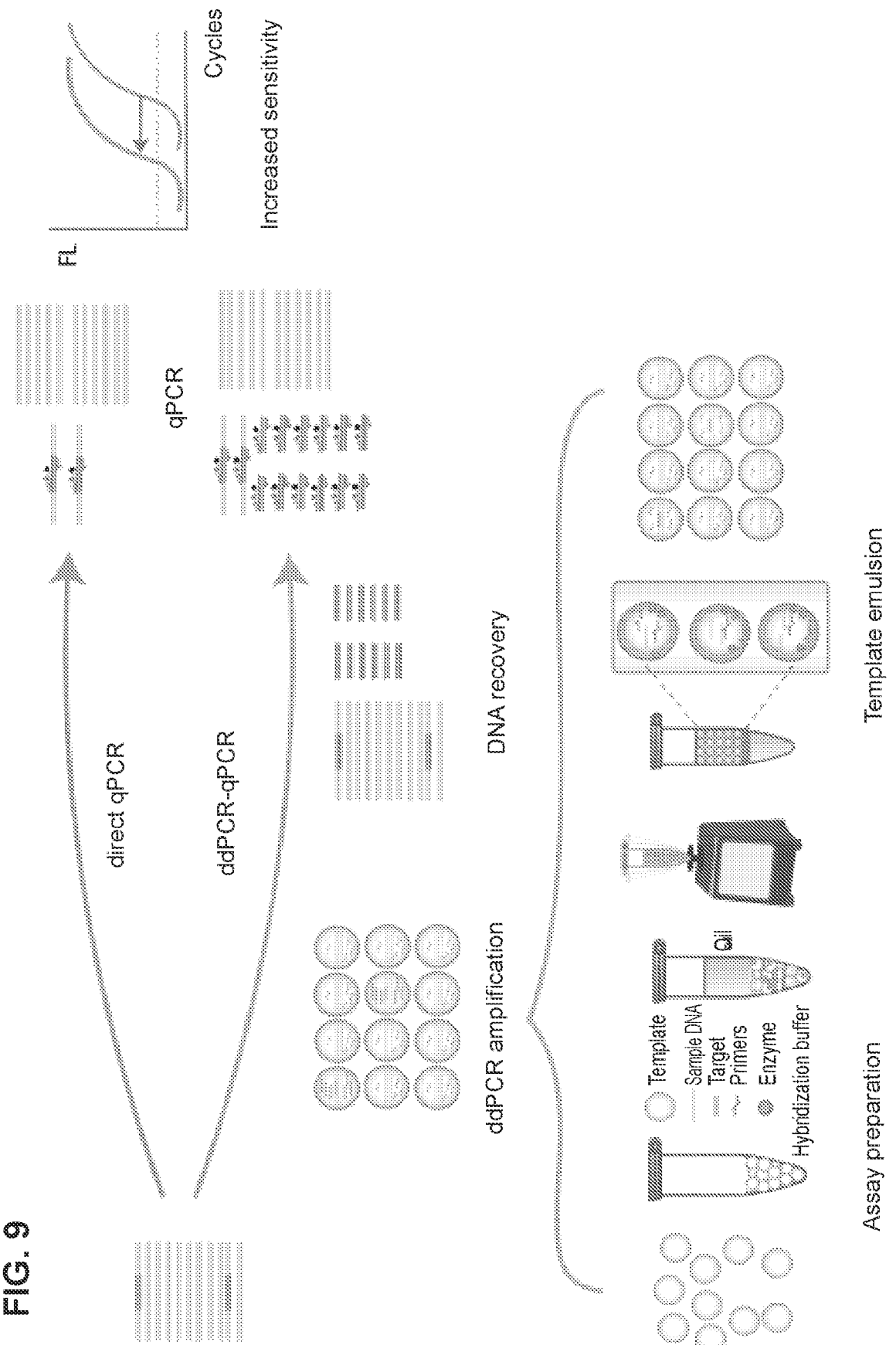
FIG. 9 shows the workflow for bulk readout of digital assays using qPCR.

The workflow of using qPCR to readout ddPCR is described in FIG. 9. ddPCR-qPCR can lead to the increased the sensitivity of direct qPCR by elevating the CT value. It also supplies an alternative method to replace droplet reader that quantifies droplet fluorescence in a single-file manner.

I. Exemplary Workflows and Conditions

A. Method ddPCR-qPCR

Step 1 ddPCR

PCR setup (20 ul per reaction) with 2×ddPCR mix 10 µl, N2 outprimers (10 µM) 1 µl, Template 1 µl and $H_2O$ 8 µl.

Generate 20,000 droplets per 20 µl PCR and carry out thermal cycling with 95° C. for 10 min and 45 cycles of 20 sec at 95° C. and 30 sec at 55° C.

19 ul $H_2O$ and 1 µl Proteinase K solution are added to each ddPCR before break emulsion with PFO followed by centrifugation. The samples are then incubated at 55° C. for 5 min (digestion step) and 95° C. for 10 min (deactivation of proteinase K).

Step 2 qPCR

Dilution with 2 from each ddPCR with 149 µl $H_2O$ for qPCR setup.

qPCR setup with 10 µl 2× master PCR mix, 2 µl diluted ddPCR solution, 1.5 µl N2 primer set (forward primer, reverse primer and probe) and 6.5 µl $H_2O$.

Use PCR condition as 95° C. 2 min followed by 40 cycles of 95° C. 15 s, 55° C. 60 s and 72° C. 30 s.

Results

Figure 10:
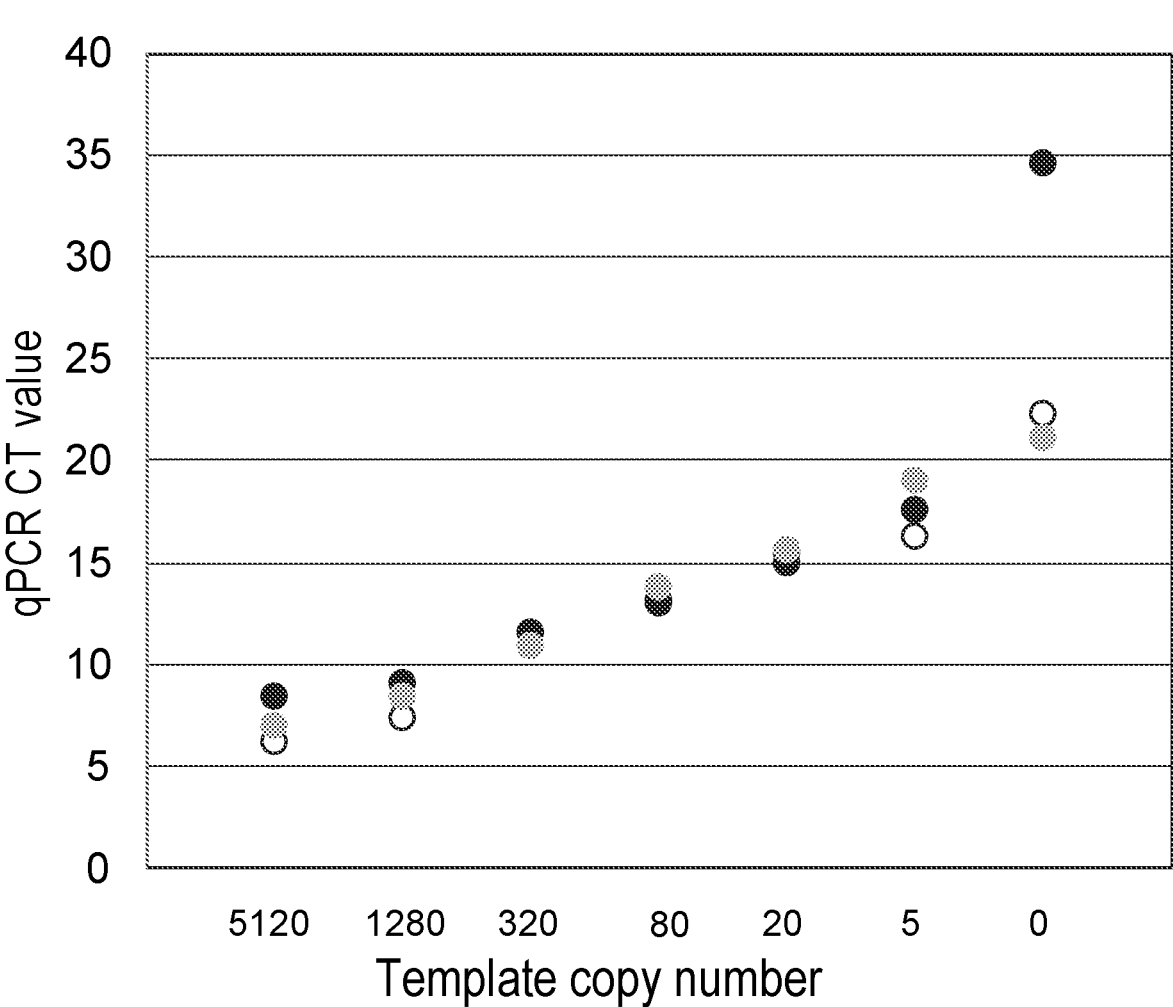
FIG. 10 shows that ddPCR-qPCR can reliably detect 40 copy targets and it follows good linear trend while increasing copy numbers.

Series dilution of samples containing 5, 20, 80, 320, 1280 and 5120 copies of COVID19 N gene plasmid per µl were used to carry out the workflow. qPCR results indicate that this ddPCR-qPCR can reliably detect 40 copy targets and it follows good linear trend while increasing copy numbers (FIG. 10).

B. Method ddPCR-BioA, or ddPCR-Qubit

The purpose of this method is to use bioanalyzer or Qubit to directly quantify the ddPCR products.

BioA=The Bioanalyzer (G2938A) is a chip-based capillary electrophoresis machine to analyze RNA, DNA, and protein. The chip used in this example is the Bioanalyzer High Sensitivity DNA Analysis kit (part number 5067-4626, Agilent).

Qubit=Qubit™ fluorometer. Qubit Fluorometers detects fluorescent dyes that are specific to the target of interest. These fluorescent dyes emit only when bound to the target molecules, even at low concentrations. The reagents used in this example is the Qubit™ dsDNA HS Assay Kit (Catalog number: Q32851, ThermoFisher).

1. Method ddPCR-BioA

Step 1 ddPCR

PCR setup (20 ul per reaction) with 2×ddPCR mix 10 µl, N2 outprimers (10 µM) 1 µl, Template 1 µl and $H_2O$ 8 µl Generate 20,000 droplets per 20 µl PCR and carry out thermal cycling with 95° C. for 10 min and 45 cycles of 20 sec at 95° C. and 30 sec at 55° C.

19 µl $H_2O$ and 1 ul Proteinase K solution are added to each ddPCR before break emulsion with PFO followed by centrifugation. The samples are then incubated at 55° C. for 5 min (digestion step) and 95° C. for 10 min (deactivation of proteinase K)

Step 2 BioA Readout

Load 1 µl of the products directly to bioA chip for bioA

Results-BioA

Figure 11:
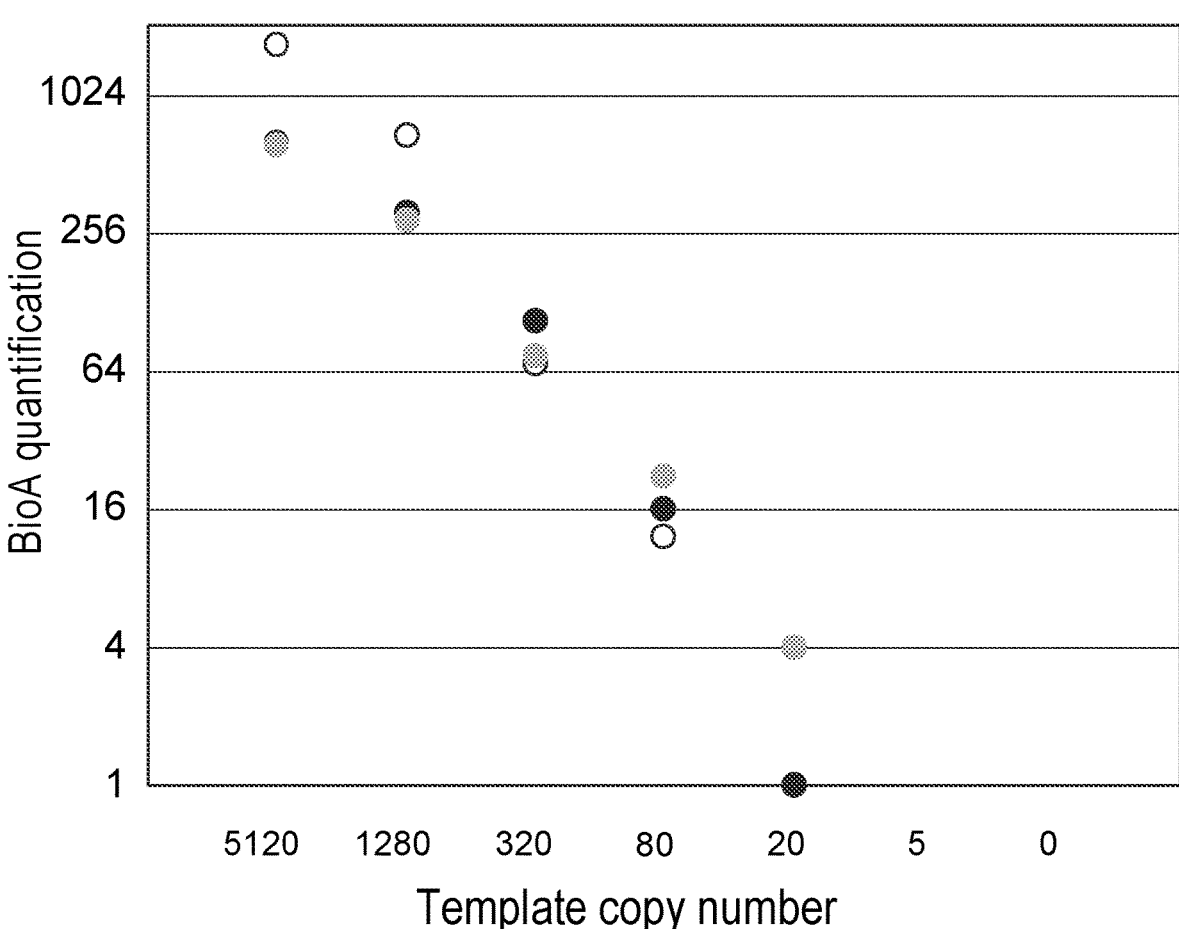
FIG. 11 shows the results for using a bioanalyzer to directly quantify the ddPCR products.

Series dilution of samples containing 5, 20, 80, 320, 1280 and 5120 copies per µl of COVID19 N gene plasmid were used to carry out the workflow. Bioanalyzer results indicate that this ddPCR-BioA can reliably detect 80 copy targets and it follows good linear trend while increasing copy numbers (FIG. 11).

2. Method ddPCR-Qubit

Step 1 ddPCR

PCR setup (20 µl per reaction) with 2×ddPCR mix 10 µl, N2 outprimers (10 µM) 1 µl, Template 1 µl and $H_2O$ 8 µl.

Generate 20,000 droplets per 20 ul PCR and carry out thermal cycling with 95° C. for 10 min and 45 cycles of 20 sec at 95° C. and 30 sec at 55° C. 19 µl $H_2O$ and 1 ul Proteinase K solution are added to each ddPCR before break emulsion with PFO followed by centrifugation. The samples are then incubated at 55° C. for 5 min (digestion step) and 95° C. for 10 min (deactivation of proteinase K).

Step 2 Qubit Readout

Use 1 ul of the products for Qubit reading

Results-Qubit

Figure 12:
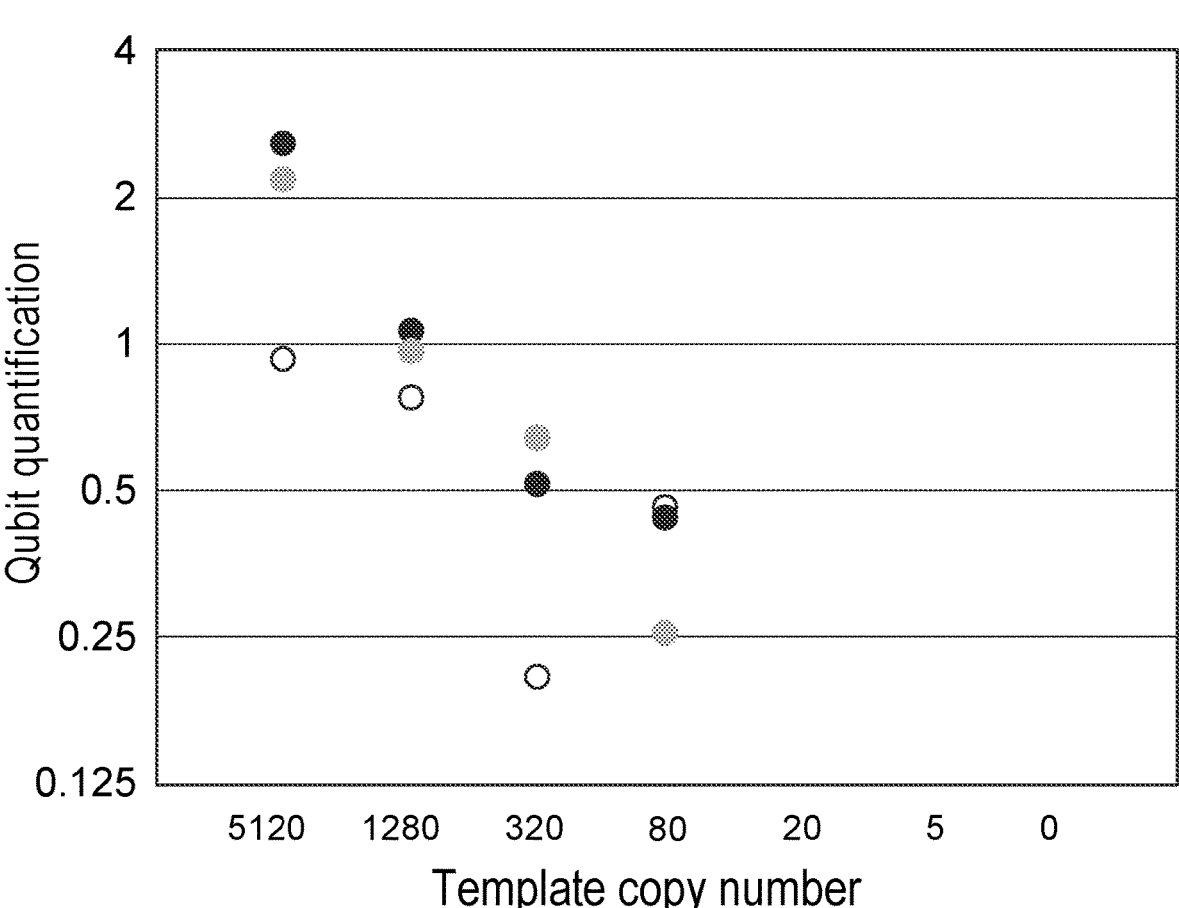
FIG. 12 shows the results for using Qubit to directly quantify the ddPCR products.

Series dilution of samples containing 5, 20, 80, 320, 1280 and 5120 copies per μl of COVID19 N gene plasmid were used to carry out the workflow. Bioanalyzer results indicate that this ddPCR-Qubit can reliably detect 80 copy targets and it follows good linear trend while increasing copy numbers (FIG. 12).

II. Accurate Bulk Quantitation of Droplet Diital PCR

The quantitation of nucleic acids is important for basic science and clinical applications. Quantitative PCR (qPCR) measures target concentration by monitoring the exponential rise of amplicons and is the gold standard due to its specificity and superb sensitivity (Heid, C. A.; et al., Genome Res. 1996, 6 (10), 986-994). By contrast, digital PCR (dPCR) subdivides the sample such that partitions contain one or no target molecule; after end-point amplification, positives are enumerated, yielding the target concentration (Vogelstein, B.; et al., *Proc. Natl. Acad. Sci. U.S.A.* 1999, 96 (16), 9236-9241; Quan, P. L.; et al., Sensors 2018, 18 (4), 27; and Heyries, K. A.; et al., *Nat. Methods* 2011, 8 (8), 649-U64). Digital PCR affords numerous advantages over qPCR, including absolute quantitation and enhanced accuracy for small concentration changes, making it especially valuable for clinical applications (Pohl, G.; et al., Expert Rev. Mol. Diagn. 2004, 4 (1), 41-47; Alteri, C.; et al., Plos One 2020, 15 (9); and Hayden, R. T.; et al., *J. Clin. Microbiol.* 2013, 51 (2), 540-546). It has secondary benefits, including increased resistance to inhibition (Dingle, T. C.; et al., Clin. Chem. 2013, 59 (11), 1670-1672; Hindson, C. M.; et al., *Nat. Methods* 2013, 10 (10), 1003-+) and the ability to differentiate intact from fragmented molecules (Lance, S. T.; et al., Virol. J. 2016, 13; Han, J.; et al., Biochim. Biophys. Acta, Gen. Subj. 2019, 1863 (8), 1235-1242), which are valuable in the identification of viable pathogens in minimally processed samples Deiana, M.; et al., Sci. Rep. 2020, 10 (1), 18764; Pavsic, J.; et al., Anal. Bioanal. Chem. 2016, 408 (1), 67-75 ( ).

Droplet digital PCR (ddPCR) uses microfluidics to partition samples in water droplets suspended in oil. While the approach is superbly accurate, the requirement of microfluidics is a barrier to its adoption, making it costly compared to qPCR, and difficult to integrate into clinical labs using standardized well plate formats. Particle-templated emulsification (PTE) partitions samples without microfluidics; the resultant emulsions are similar in monodispersity to microfluidically-generated ones and, thus, can be used to conduct most droplet assays, including ddPCR (Hatori, M. N.; et al., *Anal. Chem.* 2018, 90 (16), 9813-9820). While removal of microfluidic droplet generation is a great simplification, subsequent quantification still requires a custom droplet reader, negating much of the advantage (Baker, M., *Nat. Methods* 2012, 9 (6), 541-544; Hatch, A. C.; et al., Lab Chip 2011, 11 (22), 3838-3845; and Guo, M. T.; et al., Lab Chip 2012, 12 (12), 2146-2155). To realize the benefits of ddPCR in settings in which microfluidic instrumentation is impractical, a new approach for enumerating positive droplets that uses only common laboratory equipment and methods is needed.

The following demonstrates accurate bulk quantitation of droplet digital PCR with common lab equipment. To partition the samples, bulk homogenization with a vortexer is used. To quantitate the samples, different methods for bulk enumeration of positive droplets were compared, including fluorescence, gel electrophoresis, and qPCR. Of these, qPCR detection of droplet products yields the highest sensitivity and accuracy over the widest dynamic range. Thus, the approach described herein combines important attributes of ddPCR, including enhanced accuracy and robustness to inhibition, with the accessibility and scalability of bulk processing in well plates.

An important advantage of ddPCR over qPCR is its ability to accurately quantify small differences in target concentration, especially near the detection limit of the assay (Baker, M., Digital PCR hits its stride. Nat. Methods 2012, 9 (6), 541-544; and Suo, T.; et al., Emerg. Microbes Infect. 2020, 9 (1), 1259-1268. This benefit arises from the linear nature of ddPCR. Because qPCR is exponential, stochasticity in reaction initiation amplifies over cycles to limit the precision with which small differences in target concentration can be measured. By contrast, when cycled to endpoint, irrespective of when each droplet amplification initiates, the number of positive droplets in ddPCR is directly proportional to the number of input target molecules. This allows accurate measurement of target concentration, $$C = D_+/V \tag{1}$$

where C is the target concentration, $D_+$ the number of positive droplets, and V the total volume of the sample, and is the basis of ddPCR's ability to obtain an "absolute" count of target molecules, while qPCR returns only relative values unless a standard curve is provided (Hindson, C. M.; et al., Nat. Methods 2013, 10 (10), 1003-+). Thus, enumerating positive droplets is an essential step in ddPCR, and is typically accomplished using a droplet reader comprising a microfluidic optical instrument (Hatch, A. C.; et al., Lab Chip 2011, 11 (22), 3838-3845; Guo, M. T.; et al., Lab Chip 2012, 12 (12), 2146-2155). In addition to being costly, these instruments are difficult to integrate into high-volume testing because each sample must be manually processed; consequently, they are reserved primarily to settings that can bear the high labor and equipment costs (Quan, P. L.; et al., Sensors 2018, 18 (4), 27). A superior strategy would be to infer positive droplet number from a bulk measurement compatible with plate-processing of samples; this would significantly lower the barrier to adoption and enable high throughput processing in plates.

In principle, the total fluorescence of an emulsion provides a straightforward way to infer the number of positive droplets because it is the sum of the contributions of the positive $F_+$ and negative $F_-$ droplet fluorescence.

$$F = F_+ + F_- \tag{2}$$

$$F_+ = \Sigma_i f_i v_i \text{ and } F_- = \Sigma_j f_j v_j \tag{3}$$

with $f_i$ the fluorescence density and $v_i$ the volume of the ith positive droplet; and $f_j$ the fluorescence density and $v_j$ the volume of the jth negative droplet. In the limit $F_+ \gg F_-$, and assuming each positive droplet contributes an average quantum of fluorescence $\bar{f}$, the number of positive droplets $$D_+ \approx F/\bar{f} \tag{4}$$

Thus, for a suitable background fluorescence, it is possible to infer $D_+$ from bulk measurement of the fluorescence emerging from an emulsion (Morinishi, L. S.; et al., J. Vis. Exp. 2015, (103)). Nevertheless, bulk fluorescence is a poor observable due to the optical properties of ddPCR emulsions. Unless the carrier oil is index matched to the droplets, emulsions are opaque (Chantrapornchai, W.; et al., Food Res. Int. 2001, 34 (9), 827-835; and Liao, P. Y.; et al., Proc. Natl. Acad. Sci. U.S.A. 2020, 117 (41), 25628-25633); the amount of signal detected from a droplet deep within the emulsion may thus differ from one near the surface. In addition, common methods for measuring fluorescence in wells read from the bottom which limits reproducibility, since collection efficiency will depend on where the emulsion is in the tube and how long it has settled before being read. Most importantly, ddPCR assays have nonzero background ($f_j$ is not negligible compared to fti) such that the condition $F_+ \gg F_-$ is usually only met when the number of positive drops is large; this limits sensitivity for the most important low concentrations.

In addition to fluorescence, ddPCRs produce amplicons. In principle, if similar conditions are met of low background and uniform generation from droplets, bulk measurement of amplicons should allow inference of positives in analogy to Eq. (4), $$D_+ \approx A/a \qquad (5)$$

where A is the total number of amplicons generated by a ddPCR and a the average number generated per positive droplet. Like total fluorescence, this approximation is justified when the number of amplicons generated by the positive droplets is much greater than by the negatives ($A_+ \gg A_-$). In this respect, amplicon detection is superior to fluorescence because well-designed PCRs generate few off-target products. In addition, opacity of the emulsion is not a factor, and amplicons can be measured using a variety of common and sensitive techniques, including staining, on-chip electrophoresis, and qPCR (Heid, C. A.; et al., Genome Res. 1996, 6 (10), 986-994; Nakayama, Y.; et al., Plos One 2016, 11 (3); Le Roux, D.; et al., *Anal. Chem.* 2014, 86 (16), 8192-8199).

To investigate whether amplicon quantitation provides a suitable means for estimating $D_+$ in bulk, the efficacy of these methods was compared for a dilution series of SARS-CoV-2 nucleic acids (FIG. 14). All ddPCR assays were generated with commercially available microfluidics (Bio-Rad, Droplet digital PCR applications guide. <http://www.bio-rad.com/en-us/category/digital-pcr>2014), and each sample is divided into 20,000 droplets. As expected due to the high background, bulk fluorescence poorly quantifies ddPCR results, yielding a detection sensitivity of ~320 molecules (FIG. 13*a*). Recovering and staining DNA from the droplets and quantitating with a fluorescence reader yields a sensitivity of ~80 molecules; this technique, however, is nonspecific and detects all recovered DNA irrespective of sequence, yielding a suboptimal background (FIG. 13*b*). To reduce background, the amplicons for detection were targeted using on-chip gel electrophoresis, which allows quantitation of the peak representing the correct molecular length. The result is an improved detection sensitivity of ~20 molecules (FIG. 13*c*), which is nearly as good as direct qPCR analysis of the sample, also having a sensitivity of ~20 molecules (FIG. 13*d*, upper points). The measurement becomes less accurate at high concentrations due to multiple targets being encapsulated in the droplets. Importantly, since electrophoresis measures the lengths of all amplicons in the sample, it is readily multiplexed by designing amplicons of different length (Le Roux, D.; et al., Anal. Chem. 2014, 86 (16), 8192-8199). Moreover, when performed in an emulsion, multiplexed reactions tend to be robust because products do not compete for amplification (Dobnik, D.; et al., Sci. Rep. 2016, 6).

Below this detection limit, gel electrophoresis is ineffective because the recovered molecules are too few to be detected. To increase detection sensitivity further, a more sensitive amplicon quantitation approach was considered. qPCR is a sensitive technique for quantifying nucleic acids and has the benefits of being specific and multiplexable since primers can be targeted to different sequences. As such, with qPCR of ddPCR products, a detection of just ~5 molecules was achieved (FIG. 13*d*). Below this, detection becomes unreliable because there are so few molecules there is large variability due to statistical loading of targets in the sample (Basu, A. S., Slas Technol. 2017, 22 (4), 369-386). In concordance with this, increased standard deviation was observed when the sample has ~5 targets. Amplification was not observed in template controls in both direct qPCR and ddPCR+qPCR, likely due to airborne contamination or non-specific amplification. When targets are abundant, qPCR affords excellent quantitation (FIG. 13*d*). However, direct qPCR has higher $C_t$ values because it detects targets directly, while ddPCR+qPCR detects the amplicons generated by the droplets; the result is that much more DNA is present at the beginning of the qPCR analysis, yielding smaller $C_t$ values. This demonstrates that bulk quantitation of ddPCR-generated amplicons, like direct droplet enumeration, is ultimately limited by statistical loading of targets in the sample and not by the assay sensitivity or accuracy.

While ddPCR+qPCR affords the best sensitivity of all methods tested and even surpasses qPCR, the requirement of microfluidics to generate the emulsions is a major limitation. Indeed, emulsions can be generated by simpler methods, including bead beating, sonication, and pipetting (Hatori, M. N.; et al., Anal. Chem. 2018, 90 (16), 9813-9820; Gaikwad, S. G.; et al., Ultrason Sonochem. 2008, 15 (4), 554-563; and Yeung, A.; et al., Colloids Surf., A Physicochem. Eng. Asp. 2000, 174 (1-2), 169-181). Vortexing also produces emulsions, with the benefits of being simple, fast, and amenable to parallel processing. However, these bulk methods generate polydispersed emulsions in which droplet size varies substantially compared to microfluidics. While accurate ddPCR has been demonstrated in polydispersed emulsions when droplets are imaged and counted (Byrnes, S. A.; et al., Anal. Chem. 2018, 90 (15), 9374-9380), it is unclear whether this holds for bulk detection because, when cycled to end-point, the number of amplicons generated in a droplet scales with its volume. Thus, the total number of amplicons in the recovered pool will depend on the volumes of the positive droplets, which will vary, $$A = \Sigma_i a_i v_i \qquad (6)$$

with a$t$ the amplicon concentration and $v_i$ the volume produced by the ith positive droplet. In the limit of large $A_+$, however, the sum can be approximated in terms of the average d, simplifying the expression to $$A \approx D_+ \bar{a} \qquad (7)$$

such that Eq. (5) still holds. Below this limit, statistical variation in droplet volume dominates the measurement. Where this approximation holds will thus depend on the size distribution of the droplets, such that more polydispersed emulsions will lose their quantitativeness at higher $A_+$. To investigate this concept, another experiment was performed to quantify polydispersed ddPCR emulsions generated by vortexing (FIG. 14*a*). As expected, the emulsions are polydispersed, though positive droplets are clearly visible (FIG. 14*b*); in addition, the size distribution is much broader than for the microfluidic emulsion (FIG. 14*c*). When the recovered amplicons were measured, excellent quantitation was found, with minimal error down to 20 molecules. Below this, statistical variation in droplet size increases error (FIG. 14*d*, right) though the measurement remains quantitative down to ~5 molecules, and nearly as good as monodispersed emulsions (FIG. 13*d*). Furthermore, vortex-generated emulsions have smaller average droplet sizes than the microfluidic ones and, thus, the sample is subdivided into more partitions, increasing dynamic range at higher concentrations.

Conclusions

The approach described herein combines the benefits of ddPCR with the simplicity, accessibility, and scalability of plate processing. Bulk emulsification is achieved by vortexing to perform ddPCR, and bulk quantitation of generated amplicons to quantify the results, yielding a measurement accuracy superior to qPCR and similar to microfluidic ddPCR. In addition to its accuracy, our approach has benefits of ddPCR, including robustness to inhibition and efficient multiplexed reactions. Moreover, a variety of amplicon detection strategies can be used with distinct advantages, such as automated electrophoresis, which is simple, fast, and accurate down to a detection limit of ~20 molecules, and qPCR, with a sensitivity of ~5 molecules. While bulk emulsified samples afford high accuracy that surpass qPCR, statistical variation in droplet size results in increased measurement error for rare targets compared to monodispersed emulsions. In instances in which this error is unacceptable, particle-templated emulsification can generate monodispersed emulsions by vortexing (Hatori, M. N.; Anal. Chem. 2018, 90 (16), 9813-9820). This approach affords other valuable features, including the ability to tune droplet size to optimize the number of amplicons generated for bulk quantitation. Moreover, using droplets of different size to analyze the same sample increases dynamic range (Byrnes, S. A.; et al., Anal. Chem. 2018, 90 (15), 9374-9380). By implementing multiplexing, it is also possible to detect a variety of targets in the same sample (Dobnik, D.; et al., Sci. Rep. 2016, 6) and to estimate the intactness of molecules based on how their subsequences co-distribute (Lance, S. T.; et al., Virol. J. 2016, 13), which is important for clinical diagnostics in which differentiation of fragmented and intact pathogenic genomes may be important for reducing false positive test results. In addition, multiplexing by measuring ddPCR amplicons of different length should allow simultaneous detection and quantitation of insertion, deletion, and splice mutants in research or clinical samples. The present methods thus combines key benefits of ddPCR with the simplicity and scalability of plate processing and, thus, can be readily implemented to increase the accuracy and robustness of nucleic acid testing.

Materials and Methods

Droplet Formation by Commercial Droplet Generator

QX200 droplet generator (Bio-Rad, #1864002) was used to make emulsions following the manufacture's instruction. Briefly, 20 µL reaction mix was prepared using ddPCR Supermix for Probe (no dUTP) (Bio-Rad, #1863024), N2 outer primers (F: AAC ACA AGC TTT CGG CAG AC (SEQ ID NO: 1), R:CCC GAA GGT GTG ACT TCC AT (SEQ ID NO: 2); final concentration of 500 nM) and template (2019-nCoV_N_Positive Control, Integrated DNA Technologies, #10006625). The ddPCR reaction mix was added to the droplet generator and converted to droplets with the use of Droplet Generation Oil for Probes (Bio-Rad, #1863005) and DG8 Cartridges and Gaskets (Bio-Rad, #1864007).

ddPCR and Bulk Readouts

Emulsified samples were transferred to PCR tubes and thermocycled in a Thermal Cycler (Bio-Rad, T100 model). Thermal cycling was performed at: 10 min at 95° C.; 45 cycles of 20 s at 95° C., 30 s at 55° C. and 30 s at 72° C. After ddPCR, the droplets were transferred to a flat-bottom well plate and the bulk fluorescence was measured by a Microplate reader (Tecan, Infinite 200 PRO). For BioA and Qubit measurement, 1 µL Proteinase K (800 units/ml, NEB, #P8107S) was diluted in 20 µL $H_2O$ and added to the thermocycled emulsions. The emulsions were then broken using 10 µL of 10% (v/v) solution of perfluoro-octanol (Sigma-Aldrich, catalog no. 370533), followed by gentle vortexing for 5 s and centrifugation for 1 min (Benchmark Scientific, MyFuge Mini centrifuge). After droplet breaking, the tubes were incubated for 10 min at 55° C. to digest the remaining enzymes in the solution. Another incubation of 95° C. for 10 min was used to deactivate the Proteinase K. L of the resulting solution was added directly to Bioanalyzer (Agilent 2100) or Qubit (Invitrogen, Qubit 2.0 Fluorometer) to quantify the ddPCR products. The concentration of peak of the correct molecular length was readout from Bioanalyzer. The total DNA concentration in the sample was measured by Qubit.

For qPCR readout, 1 L of the PK treated solution was taken and diluted 100 times in DNA-free water. TaqMan PCR was used with primers and probe targeting the ddPCR amplicon. The 20 µL qPCR reaction was assembled from 10 µL Platinum Multiplex PCR Master Mix (Life Technologies, #4464269), 1.5 µL N2 primer set (2019-nCoV RUO Kit, Integrated DNA Technologies, #10006713), 1 µL diluted ddPCR products and 7.5 µL $H_2O$. The qPCR was performed in a QuantStudio 5 Real-Time PCR System (Thermo Fisher Scientific) using the following parameters: 95° C. for 2 min; 40 cycles of 95° C. for 15 s, 55° C. for 1 min and 72° C. for 30 s. Ct values for each sample was recorded as a measurement of the concentration of the target.

Droplet Formation by Vortexing

DDPCR reaction mix was prepared the same as above, using ddPCR Supermix for Probe (no dUTP), N2 outprimers (final concentration of 500 nM) and template (2019-nCoV_N_Positive Control). 30 µL Droplet Generation Oil for Probes was added to the 0.2 mL PCR tube containing 20 µL ddPCR reaction mix. The tube was then placed on a vortex (Scientific Industries, digital vortex-genie 2) and agitated at 3000 rpm for 10 min. After vortexing emulsification, the samples were thermal cycled for ddPCR and readout by qPCR as described above. For positive drop visualization, one ddPCR using TaqMan primer and probe (N2 primer set) was performed. Droplets were imaged using a EVOS microscope (Thermo Fisher) with EVOS FITC LED light sources. The emulsion breaking and qPCR quantitation of ddPCR are performed the same way as above.

III. Exemplary Workflow and Analysis of Bulk Quantification Droplet Digital LAMP Dilutions of a SARS-CoV-2 were prepared with the addition of 1, 10, 100, and 1000 copies added to DEPC purified water. Addition of WarmStart RTx Reverse Transcriptase (M0380L) reagents, Bst 2.0 WarmStart DNA Polymerase (M0538L), and the LAMP primers to the SARS-CoV-2 dilutions and mixing was followed by the addition of 2% 008-fluoroSurfactant (Ran Biotech) surfactant in HFE7500 oil. Agitation resulted in the formation of droplets containing these reagents and single molecules of the SARS-CoV-2 RNA. Following isothermal incubation in a thermocycler (Bio-Rad, T100 model) at 60° C. for 45 minutes, 0.1 volume of perfluoro-octanol (Sigma-Aldrich, catalog no.

370533) was added to each tube to break the emulsion. Once broken, 1 uL of each samples was used to determine concentration using a Qubit (Invitrogen, Qubit 2.0 Fluorometer) (FIG. 15a). Additionally, 1 uL of each sample was also loaded into the Bioanalyzer (Agilent 2100). The resulting Bioanalyzer data (FIG. 15b) between primer dimer peaks (100 bp) and the upper limit marker (10 kbp) was analyzed using two methods of analysis. Briefly, each sample was analyzed by integrating intensities within 0% (the maximum), 25%, 50%, and 100% (all) of the maximum or percentile. Plotting the integral of these intensities based on maximum intensity (FIG. 15c) or percentile (FIG. 15d) against the copy number. Logarithmic fits were made for each sample given each method of analysis and the corresponding R2 values plotted (FIG. 15e).

Conclusions

The Bioanalyzer provides a readout relating the amplicon size (time) and concentration (intensity). The high R2 values of the corresponding logarithmic fits suggests a relationship between the intensity integral and the copy number within the sample. Specifically, analysis based on the intensity percentile yielded the best fits.

Example 5

Digital Droplet LAMP Assay Detection at Point of Care—Imaging with a Microscope Versus an iPhone The following Example describes the fabrication of a dual-height 2-d chamber chip for droplet imaging.

Fabrication of the Dual-Height 2-d Chamber

Standard photolithography was used to make two-layered structures (80 and 190 m, respectively) on a 3-inch silicon wafer with SU-8 3025 photoresist (MicroChem, Westborough, MA, USA).

PDMS prepolymer and curing agent (Sylgard 184 silicone elastomer kit) were mixed at a ratio 1:10, de-gassed in a vacuum chamber, poured over the mold, de-gassed until no more bubbles were visible and baked at 65° C. overnight. PDMS replica was removed from the mold, inlets, and outlets punched with a custom made 0.75 mm biopsy puncher and individually plasma bonded to glass slides (75×25×1 mm, Fisher Scientific) by treating with oxygen plasma for 45 s at 1 mbar (PDC-001, Harrick Plasma). The device was baked at 65° C. for 24 h and treated with Aquapel (PPG Industries) with a contact time of about 1 minute and purged with HFE 7500 oil (3M™ Novec™ 7500 Engineered Fluid).

The bottom of the glass slide was covered with a black vinyl tape-based mask, with approximately 14 mm circular opening in the middle for the circular 2-d chamber (also known as the observation chamber), to limit the amount of light penetrating the PDMS chip.

A 470 nm excitation gel filter (25×35 mm Lee Filters, Deep Purple #797) was attached to the side of the PDMS chip closer to the shallower part of the 2-d chamber (80 m).

The volume of the shallower and the deeper part of the observation chamber was estimated as 1.7 µl, and 19 µl, respectively (with a total amount of approximately 22 µl).

In the shallower part of the chip, it is expected that a monolayer of droplets is observed, allowing quantification of the highly concentrated sample (with a higher number of positive droplets). The deeper part, due to its dimensions, is used for the detection and quantification of the less concentrated samples (with as low as only a few positive droplets). The droplets will fill this part of the observation chamber as a multilayer.

Droplet Sample and the Observation Chamber Handling

Directly before the use, the PDMS 2-d chamber was flushed twice with 201 of HFE 7500 oil with 2% (w/v) PEG-PFPE surfactant using a 201 pipette. Approximately ½ of the oil (v) was left in the chamber to protect the incoming sample droplets.

The outlet of the PDMS chip (in the deeper part of the dual-height 2-d chamber) was connected to a 2001 pipette through a polymer tubing. The sample emulsion was then aspirated with a 201 pipette and inserted the tip into the inlet of the PDMS chip (in the shallower part of the dual-height 2-d chamber). After disconnecting the pipette from the 201 tip, all remaining sample droplets were collected and pipetted them into the pipetting tip already inserted to the inlet of the PDMS element.

The chip was angled at about 750 with the outlet facing up, to allow the air to escape. The observation chamber was filled with the droplets, using negative pressure generated by turning the adjusting screw of the 200 µl pipette connected to the outlet of the chip. Once all the air was removed, and the continuous phase (the HFE oil) filled the 2-d chamber, the chip was flipped up-side-down, to allow the droplets to cream and fill up the whole volume of the observation chamber.

Finally, the tip and the tubing from the PDMS chip were simultaneously removed, preventing unwanted and uncontrolled drift of the droplets inside the 2-d chamber.

Imaging with an EVO Fluorescent Microscope

To scan the whole area of the dual-height 2-d chamber, a scanning feature of an EVO fluorescence microscope (EVOS Cell Imaging System, Thermo Fisher Scientific) was used. Typically 12 images were acquired within 2 minutes and stitched together, forming a full view of the observation chamber with 2× magnification.

Imaging with an iPhone-Based Fluorescent Microscope

A portable fluorescent microscope was built based on an iPhone8+ with a WF10X 18 mm lens and a 524/24 nm bandpass filter (Semrock, #FF01-524/24-25) attached directly to the smartphone.

As a fluorescent light source, a 470 nm LED (OSRAM Opto Semiconductors, #GB QSSPA1.13-HYJX-35-1) powered by a 3V coin battery was used. To filter out green light emitted by the LED, a 470 nm excitation gel filter that was added to the side of the individual PDMS chip was used.

During imaging, the LED was positioned at an approximately 45° angle, facing towards the corner of the PDMS element, closer to the shallower part of the 2-d chamber (80 m).

Adhesive was used to attach the observation chamber directly to the 10× lens.

An iPhone app (Moments by Moment Inc.) was used to capture a full scan of the observation chamber within 3 seconds. In the Moments iOS application, manual settings were used: ⅓s exposure time, ISO 486 or 2000, and manual focus set to 0. Before acquiring photos, the size of the captured image was manually adjusted by pinching out the field view to utilize the full display.

Quantification of the Data—Counting Fluorescent Droplets

To quantify the results, the acquired scans of the 2-d chambers (both, from EVO and the iPhone-based portable microscope) were analyzed, calculating the number of fluorescent droplets visible on the images.

To do that, either a manual method based on Fiji Cell Counter plug-in or custom made Python script for automated image processing—fluorescent droplet detection that also runs from the smartphone was used.

Quantification of the Data Using Droplet Single/Multilayer Imaging

The dual-height 2-d chamber was designed to consist of two connected microfluidic elements of different dimensions, to analyze droplets in a mono and multilayer format. The chip accommodates nearly 22 µl of the droplet sample, allowing for easy and fast quantification of the positive droplets found in the sample's whole volume.

It was found that displaying the droplets simultaneously as mono and multilayer allows us to analyze samples with a broader dynamic range of detection.

To detect a low number of positive droplets, the fluorescent droplets were counted in both the shallow and the deeper parts of the chamber. The deeper part of the chip allows accommodating, in the form of a multilayer, much higher number of droplets per surface area/volume, increasing the chance of finding a positive hit. This limits the size of the observation chamber and enables us to scan the chip's whole surface area using just one image without the need for a very complex imaging setup (e.g., a smart phone-based portable microscope). To analyze the same amount of droplets (22 µl) displayed as a monolayer, a over 10× bigger observation chamber is needed.

As the number of positive hits increases in the sample and exceeds the amount when a signal of two overlapping fluorescent droplets can't be separated (approximately 1000 droplets per sample), the shallower part of the chip was used to quantify and estimate the total number of fluorescent droplets. When droplets form a monolayer, they do not overlap, allowing the ability to count individual fluorescent droplets even in the samples with a very high number of positive hits.

FIG. 16 provides the following information and observations.

A) An overview of a portable smartphone-based fluorescent reader for the ddLAMP readouts—a current setup used in the experiments (real photo, left). The smartphone is used as a digital camera and an image processing unit and a portable fluorescent microscope. The microscope has an emission bandpass filter 524/24 nm and a 10× magnifying lens. A microfluidic PDMS dual-height observation chamber, with droplets with the ddLAMP assay, is attached directly to the 10× lens. The PDMS chip has an excitation gel filter that eliminates unwanted wavelengths emitted by the fluorescent light source, an LED, with a max emission at 470 nm (cartoon, middle). The portable smartphone-based fluorescent reader analyzes the whole sample (~22 µl) at one go due to the design of the dual-height observation chamber. The right part of the observation chamber (~1.7 µl in volume) is shallower, being about 80 m tall, and the left part of the PDMS chip (~19 µl in volume) is about 2.5× taller.

The height of the shallow part of the observation chamber forces the droplets to form a monolayer. The taller part of chip allows the droplets to form multiple layers (right).

B) The dual-height observation chamber increases the dynamic range of detection of the ddLAMP assay in a fixed area. In the case of the lower end of the range of detection, a relatively small number of highly fluorescent droplets are present in the whole sample. Therefore, a large pool of droplets needs to be analyzed to find a few positive droplets. Stacking droplets on top of others, in the form of a multilayer, is multiplexing the readout. On the high end of the dynamic range of detection, the number of positive droplets increases, reaching a threshold above which it's impossible to distinguish single droplets and quantify the assay results in multilayers of droplets. In this case, a monolayer of droplets allows quantifiable readouts as single droplets are easily identified.

C) The sensitivity experiments performed both on the EVOs fluorescent microscope, and a portable smartphone-based fluorescent reader provides visual confirmation of the concept of increasing the dynamic range of detection (in a small fixed area of the chip) by analyzing the ddLAMP assay in an observation chamber that allows the droplets to form both mono- and a multilayer. As the number of fluorescent droplets increases, up to a 10-4 dilution of the positive control, all the droplets are identifiable and easy to count in the whole chip. Above that threshold, the number of positive hits is so high that no longer it is possible to distinguish single droplets and quantify the assay results in part of the chip where the droplets form multilayer. In this case, as volumes of both parts of the chip are known, the total number of fluorescent droplets present in the whole sample is estimated by counting individual positive droplets in the observation chamber's shallow section.

D) The quantified results of the assay's sensitivity provide information on the performance of the portable smartphone-based fluorescent reader for the ddLAMP readouts. In most parts of the detection range, both readout methods, the EVOs, and the smartphone-based setup give similar outcomes. The data from EVOs-based images allow for a wider dynamic range of detection (5-folds) due to a better optical system. The portable smartphone-based fluorescent ddLAMP reader has a narrower (4-folds) dynamic range of detection based on the quality of the images provided by the smartphone. The detection limit is <10 copies/reaction.

Example 6

Digital Droplet PCR by Rehydrating Pre-Dried Polyacrylamide Beads

Figures 17A, 17B:
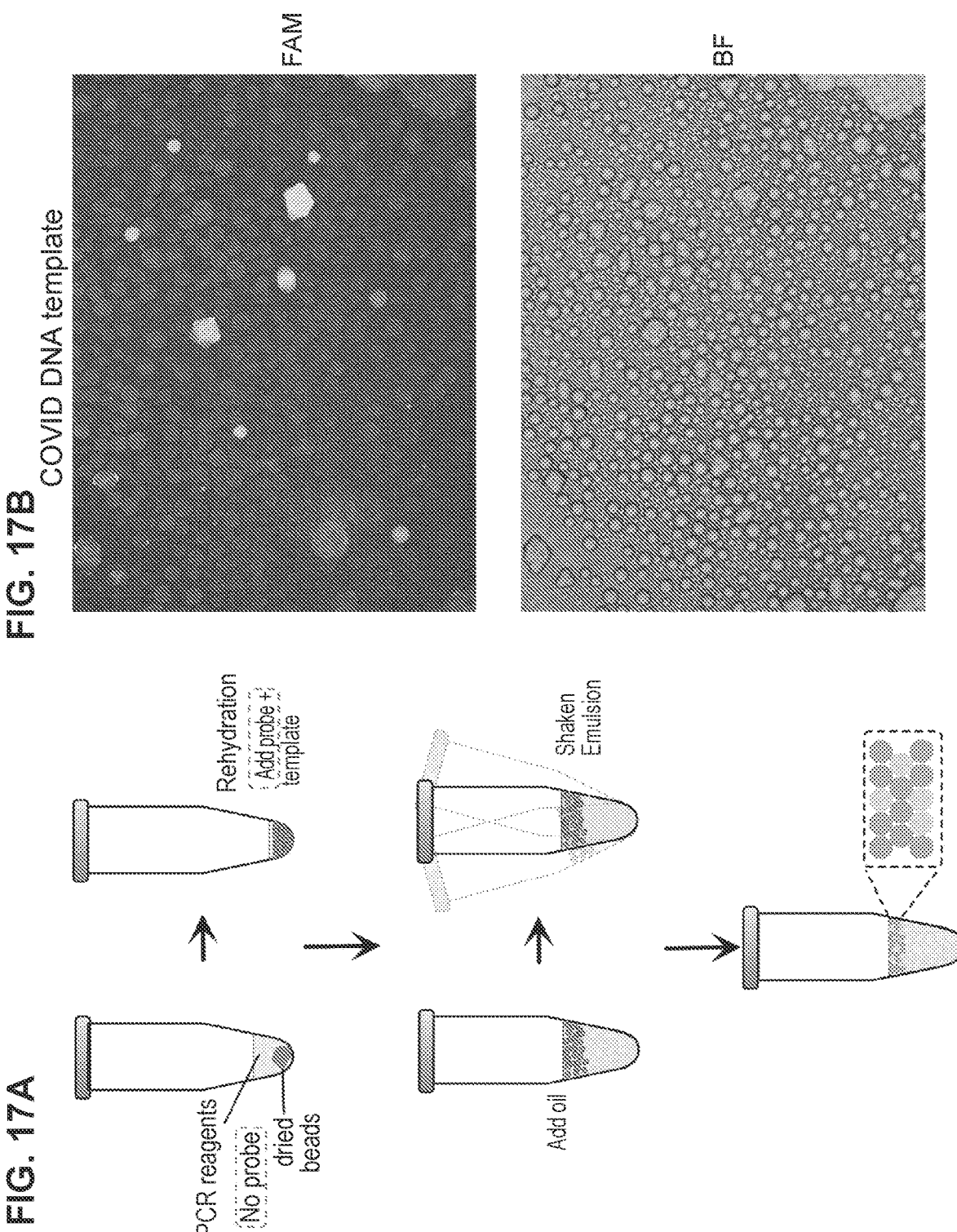
FIG. 17A and FIG. 17B shows the workflow and results of ddPCR by rehydrating pre-dried polyacrylamide beads.

The following Example describes the workflow and sample of performing ddPCR by re-hydration of pre-dried polyacrylamide beads. 25 µl polyacrylamide beads are pre-dried and then rehydrated by 25 µl PCR reagents containing the DNA template but without fluorescent probes. After the beads are fully re-hydrated, the fluorescent probes are added into the beads. After adding oil with surfactants, the tube is agitated by shaking or vortexing to create emulsion. The particle-based emulsion is then subjected to PCR thermocycling conditions to amplify the targets. After the ddPCR is done, the fluorescent signals of the emulsion are quantified by imaging. An example of the method is shown in FIG. 17. Plasmids carrying the SARS-COV-2 N gene fragments are used as the template and after the ddPCR by rehydration methods, the emulsion is imaged under fluorescent microscope. Top panel is the FAM channel and the bottom panel is the bright field channel. The images showing good amplification of the targets.

Example 7

Sonication of Particle-Based Shaken Emulsion Removes Satellite Droplets

The following Example describes the protocol and results for sonication of a particle-based, shaken emulsion.

Protocol:

0.02 g Bio Rad Bio-Gel P-60 beads are re-hydrated with 5001 PVP (0.35% w/v)

Leave for about 5-10 min,

Remove supernatant if possible,

Centrifuge for 180 s at 10 k rpm.

Remove supernatant (eliminate as much as possible non-absorbed aqueous phase)

Add 500 μl HFE of HFE 7500+2% surfactant

Vortex about 30 sec to create emulsion.

Figures 18A, 18B:
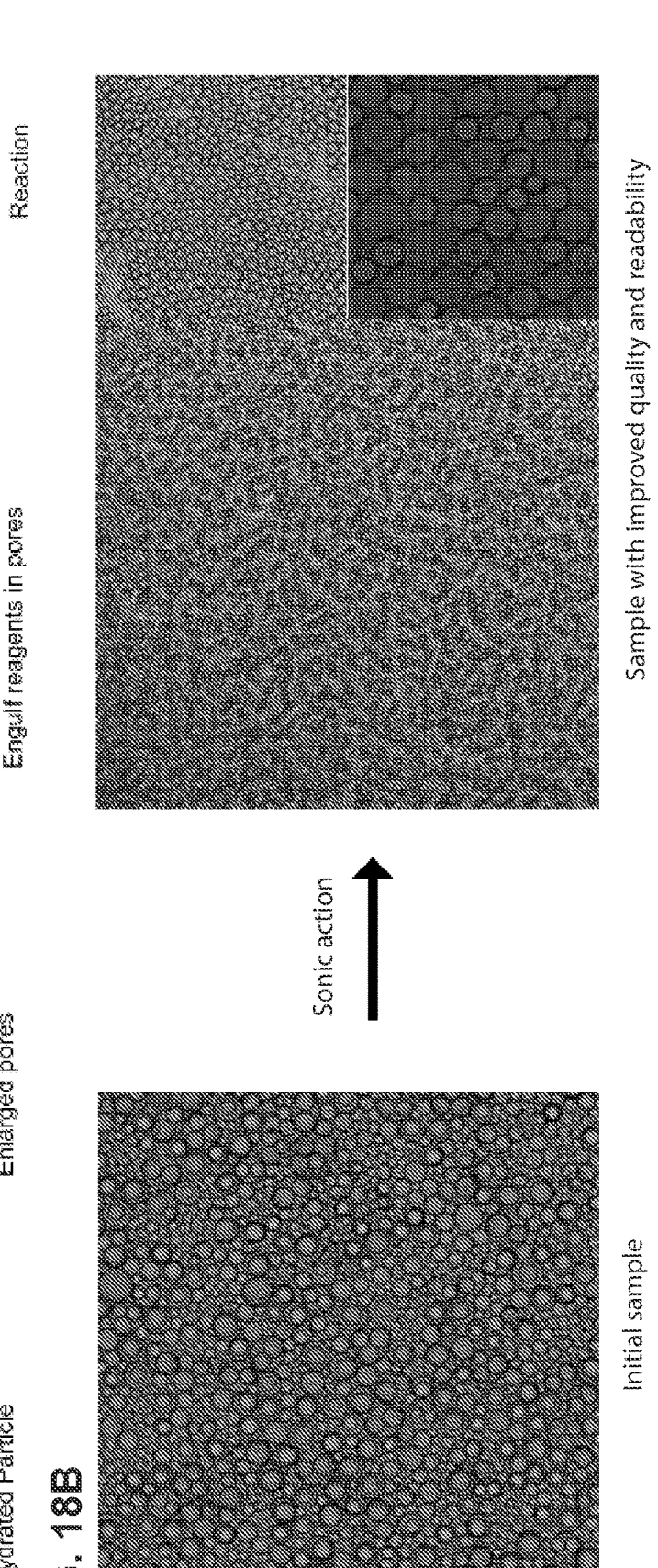
FIG. 18A and FIG. 18B shows that sonication of a particle-based, shaken emulsion removes satellite droplets.

Results: As shown in FIG. 18, which shows:

A) An overview of a workflow with rehydration-based hydrogel processing steps for polymer templated emulsification, PTE-based droplet digital assays. The preparation steps involve generating large pores in a hydrogel particle to accommodate all the necessary components of the assay inside the particle. The pores' formation includes a method based on freeze-drying, which reversely cracks the structure of the hydrogel. When dried, the particles can be stored for an extended time. When needed, the particles can be rehydrated with all the necessary components of the assay. During rehydration, the hydrogel "heals," allowing for successful polymer templated emulsification and functional assay.

B) Sonication of particle-based droplets improves sample quality and readability. When generated by hand, or with a simple shaker's aid, PTE-based droplets can be highly polydispersed, which decreases the quality of the readout of the assay. Short exposure to ultrasound improves the sample's quality and readability, by shredding down the satellite droplets (the leading cause of polydispersity). By exposure to ultrasound, the satellite droplets are transformed into a nanoemulsion, becoming invisible background, leaving only particle-based droplets with the assay fully visible, detectable, and readable.

Example 8

Differentiate Intact Viral Genomes from Fragmented Viral Genomes

The following Example describes methods for differentiating intact genome from fragments.

Figure 19:
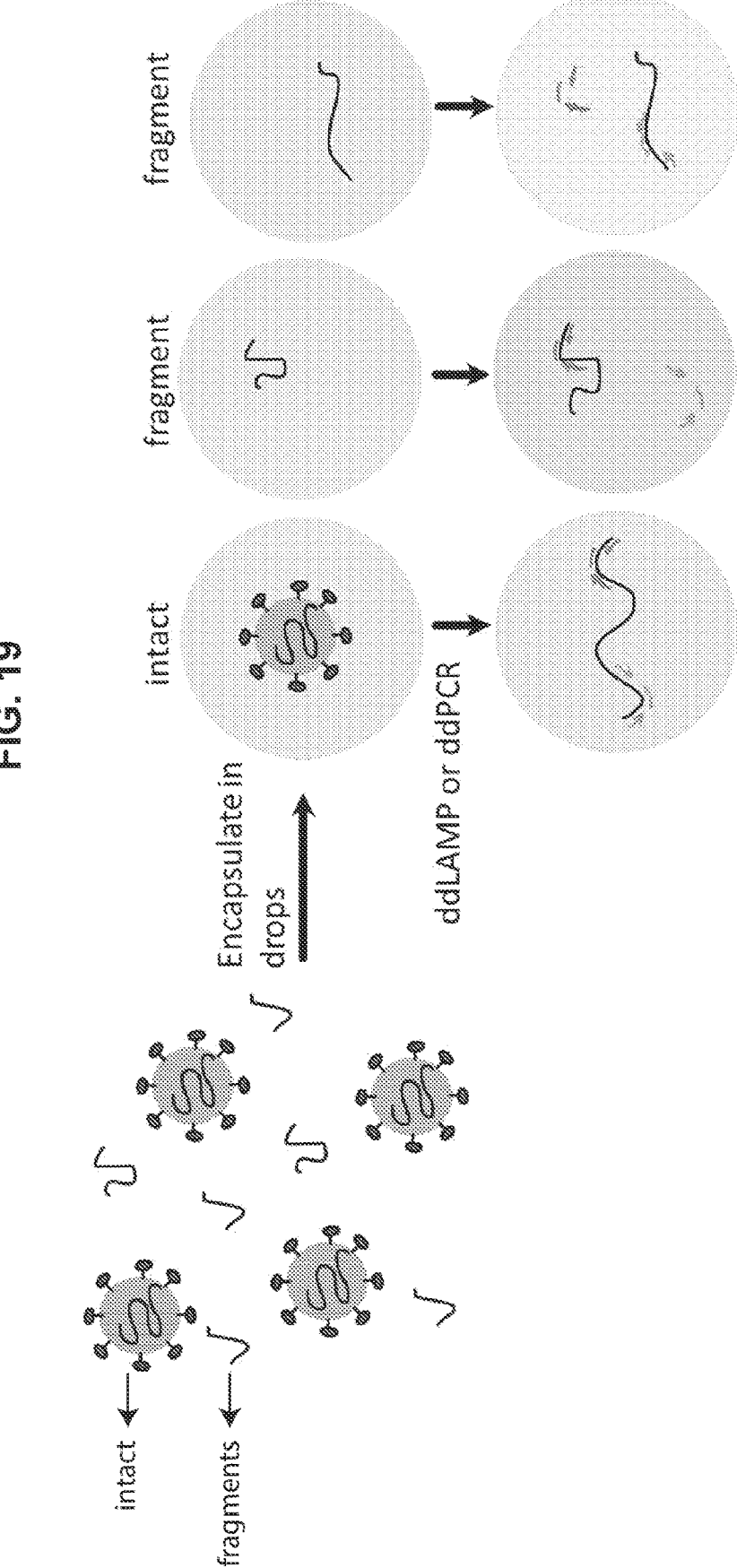
FIG. 19 shows a schematic overview for differentiating intact genomes from fragments using droplet PCR or LAMP.

FIG. 19 shows a schematic overview for differentiating intact genomes from fragments using droplet PCR or LAMP. The sample is co-encapsulated with PCR or LAMP reagents into droplets, which contain only one molecule (if any). Each droplet contains two sets of primers targeting two termini (5' and 3') of the genome. The two sets of primers or probes are labeled with fluorophores of two different colors. If the droplet contains an intact genome, the two termini of the genome will be amplified yielding both colors of fluorescence. If the droplet contains genome fragments, only one terminus of the genome will be amplified, yielding one color. By counting the droplets containing both colors, the number of intact genomes is quantified.

Figure 20:
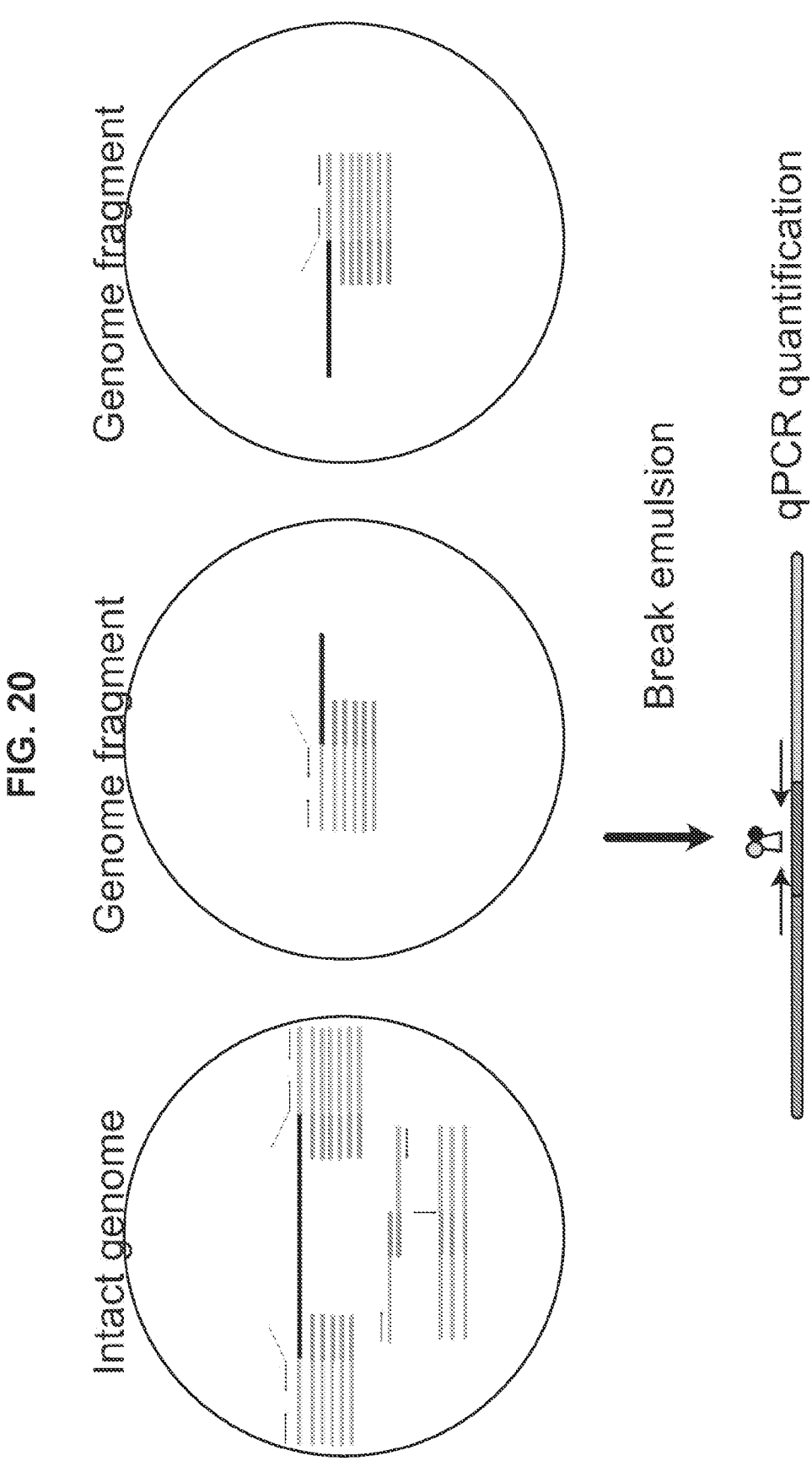
FIG. 20 shows a schematic overview of differentiating intact genome from fragments using qPCR bulk readout of droplet PCR reactions.

FIG. 20 shows a schematic overview of differentiating intact genome from fragments using qPCR bulk readout of droplet PCR reactions. Here, a sample is co-encapsulated with PCR reagents into droplets which contains only one molecule (if any). Each droplet contains two primer sets targeting two termini (5' and 3') of the genome. The reverse primer of the 5' region and the forward primer of the 3' region are fused with the same short artificial sequence. If the droplet contains an intact genome, the two termini of the genome will be amplified. The amplicons of the two primer sets have a short sequence in common, which becomes an overlapping region bridging the two amplicons and serves as a new template for the 5' forward primer and 3' reverse primer. A fusion PCR concatenates the two products into one. After droplet PCR and emulsion breaking, a bulk Taqman qPCR is performed to quantify the concatenated amplicon using a primer set that spans the junctions of the concatenated amplicon.

Example 9

Robust and Multiplexed Detection of Target Nucleic Acids Based on Subnanoliter Compartmentalized DNA Amplification and Amplicon Size or Fluorescence Analysis The following Example provides digital droplet assay methods for detecting the presence and quantifying the abundance of one or more biological entities (e.g, the detection of viruses, bacteria, cells, cancer, or any biological entity) based on multiplexing. As described herein and below, these methodologies are accomplished by running a nucleic acid reaction (e.g., LAMP, multi-primer or degenerate-primer PCR, HDR, RPA or other) and determining sample identity through reading out and deconvoluting the unique product signature that results from a multiplexed reaction. Specific forms of detection include (A) visualizing the resulting unique distribution of amplicon lengths that results for a given target or mixture of targets using eletrophoresis methods (e.g., Bioanaylzer chip or Capillary Electrophoresis instrument); (B) visualizing droplets that have multi-color fluorescent signal intensity profiles diagnostic of a given target due to molecular beacon or TaqMan hydrolysis probe mixtures; and (C) leveraging optical barcoding of droplets with fluorescent beads that specify the type of target being detected within the droplet and fluorescent detection of amplicons that indicate if target nucleic acids are present in the volume. In all methodologies A-C, droplets are essential as they facilitate the needed throughput, ensure accurate quantification of the sample through the principles of digital PCR, and allow for deconvolution of multiplex sample detection by preventing cross-talk between reactions.

A. Amplification Product Fingerprinting

The following Example describes methods for detecting and/or quantifying amplification products (e.g., amplicons) using a fingerprint associated with amplification products of different lengths (e.g., when LAMP amplification is used) or amplification products of the same/similar lengths (e.g., when PCR and the like is used). The fingerprint methodology leverages digital droplet amplification to create amplicon profiles (or fingerprints) unique to each amplification target. Targets include (but are not limited to) DNA, RNA, or tagged/barcoded with DNA or RNA. Each droplet amplification contributes an amplicon fingerprint unique to the target, and evaluation of the amplicon peaks allows for target identification while peak intensity denotes target concentration.

An Exemplary Protocol is as Follows:

1. Target(s), primer pool (all primers), and reagents (appropriate for amplification LAMP, PCR, RT-PCR, etc) are encapsulated in droplets via any number of methods (microfluidic, shaken emulsification, particle template emulsification, etc). The primer pool contains all primers for all targets, all primers and probes are equally represented in all droplets. Importantly, fluorescent probes/primers may be used but are not necessary. Preferably, the target encapsulation is performed such that up to one target per droplet is encapsulated.

2. Once emulsification has occurred, droplets are processed according to the desired amplification reaction (e.g., isothermal for LAMP, thermocycling for PCR/RT-PCR). These reactions proceed within the droplet. Importantly, performing the amplification in the droplet results in a contained reaction lowering amplification bias and preventing extensive amplification. This results in two advantages. First, each droplet contributes a consistent amplification/amplicons per target. Second, confinement to the droplet limits amplification, preventing random or uncharacterized amplification which may occur in bulk reactions that would obscure the amplification fingerprint.

3. The reaction is halted and all droplets are broken with all amplicons from all droplets collected into one aliquot. This aliquot is analyzed via, for example, capillary electrophoresis (Bioanalyzer, etc). Importantly, this is a bulk analysis. This is a simplifying aspect as opposed to analyzing each droplet individually, and represents a significant savings in time and effort.

The capillary electrophoresis analysis results in data of amplicon size vs concentration/abundance. Because each target produces a unique distribution of amplicon sizes and abundances (peaks or fingerprint). Analysis of the data (akin to x-ray diffraction, raman spectroscopy, mass spectrometry, etc) allows for each individual target fingerprint to be identified with the intensity of the fingerprint identifying the target concentration.

Figure 21:
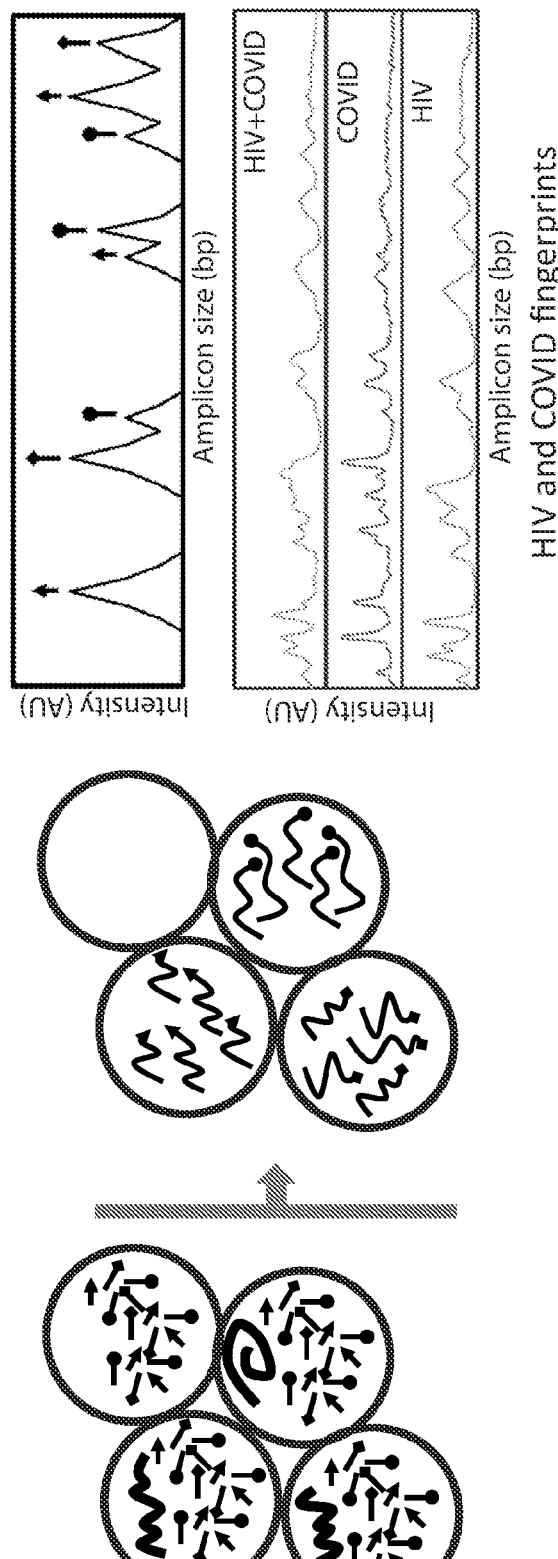
FIG. 21 shows the multiplex detection and quantification of target presence based on amplicon size and abundance distribution visualized by electrophoresis.

FIG. 21 shows the multiplex detection and quantification of target presence based on amplicon size and abundance distribution visualized by electrophoresis. Here different symbols (triangle, diamond, circle) indicate different primers with unique targets. As can be seen in FIG. 21, the resulting amplicons (lines terminating in triangle, diamond, circle) possess unique lengths measured and quantified by electrophoresis (peaks with triangle, diamond, circle correspond to amplicons with those lengths). Bioanalyzer analysis of ddLAMP targeting HIV, COVID, and the mixture of HIV and COVID amplicons yields unique and identifiable fingerprints that allow for the identification of each target within the mixture.

B. Fractional Amplification Probes (Color-Encoded Primers)

In this methodology, a unique primer set and probe is designed for each target. While the nucleotide sequence of any given probe remains the same, that probe may consist of different fluorescent molecules (e.g., X % Cy5, Y % FAM, Z % DAPI). Upon amplification, these fluorescent molecules are separated from their respective quenchers resulting in a fluorescent profile unique to molecular fraction (e.g., X % Cy5, Y % FAM, Z % DAPI). This extends the multiplexing capability beyond the number of fluorescent molecules to combinations of those fluorescent molecules.

An Exemplary Protocol is as Follows:

1. The target(s), primer pool (all primers), and reagents (appropriate for amplification LAMP, PCR, RT-PCR, etc) are encapsulated in droplets via any number of methods (microfluidic, shaken emulsification, particle template emulsification, etc). The primer pool contains all primers for all targets, all primers and probes are equally represented in all droplets. Loading should ensure that only zero-to-one target is present within each droplet. Essential to this methodology, each primer set consists of a unique fraction of fluorescent molecules. As an example, one primer set will target COVID with the associated 10% of probe FAM, 90% Cy5, and 0% DAPI, while a second primer set targeting Influenza and the associated probe consisting of 50% FAM, 50% Cy5, and 0% DAPI. Finally, a third primer set with a probe consisting of 0% FAM, 0% Cy5, and 100% DAPI will target HIV. The targets are not limited to viruses and, as described herein, can be related to any source/sample.

2. Once emulsification has occurred, droplets are processed according to the amplification reaction (isothermal for LAMP, thermocycling for PCR/RT-PCR). These reactions proceed within the droplet. As a general property of droplets, the amplification in the droplet results in a contained reaction lowering amplification bias. In the presence of a given target, all the associated fluorescent molecules will be separated from their quencher. This results in the droplet having a fluorescent profile consistent with the fraction of fluorescent molecules associated with that target. In the above example, droplet containing COVID would fluoresce mostly green (90% FAM) with a bit of red (10% Cy5) and no blue (0% DAPI). Similarly, droplets containing influenza will be yellow (50% green/FAM+50% red/Cy5+0% blue/DAPI), while droplets containing HIV would only be blue (100% DAPI). Empty droplets will have no fluorescence due to all fluorescent molecules being quenched in the absence of amplification.

3. Finally, an optical readout will assess the fluorescent profile this will enable the identification or absence of target(s) within each droplet. The number of droplets provides a method of quantification for the given target. The number of targets is determined by the number of fluorescent molecules employed as well as the ability to distinguish the fluorescent profiles.

Figure 22:
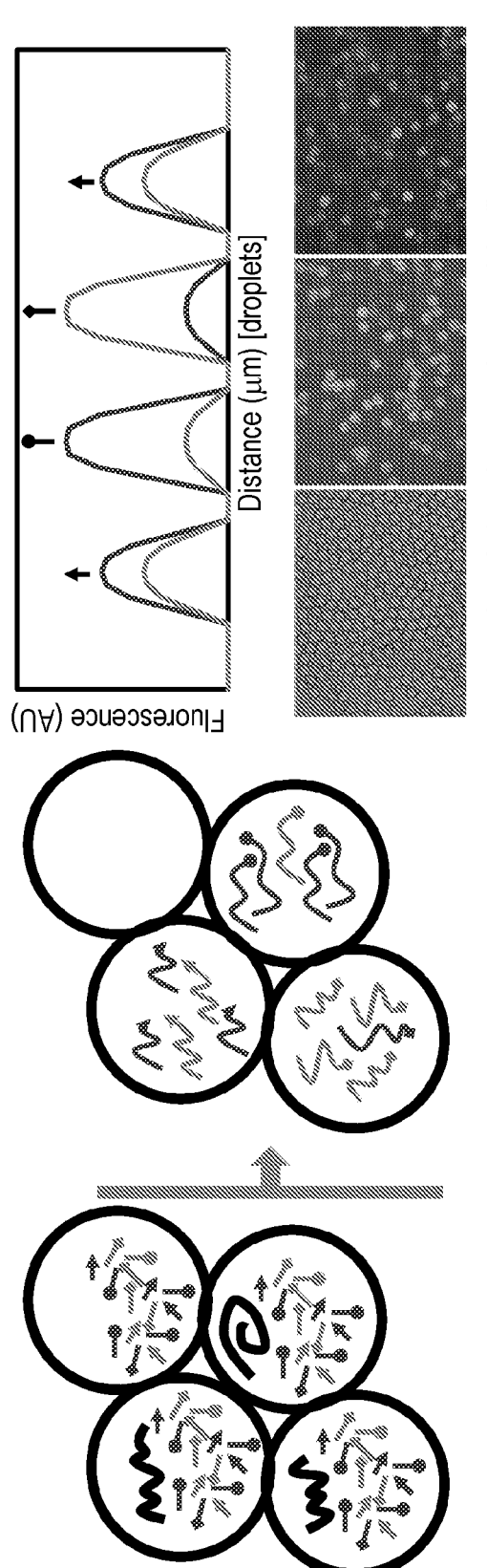
FIG. 22 shows the multiplex detection and quantification of target presence based on counting droplets with differing fluorescence profiles.

FIG. 22 shows the multiplex detection and quantification of target presence based on counting droplets with differing fluorescence profiles. The image shows that variable fluorescence can occur in droplets. Here each primer set (arrow, diamond, and circle) consists of multiple fluorescent probes (black and gray) in a unique fraction. The resulting reaction results in a droplet fluorescence proportional to the target probe fraction. This results in a droplet fluorescence unique to each target dictated by the corresponding primer set's fluorescent probe fraction.

C. Fractional Amplification Probes (Bead-Encoded and Color-Encoded Primers)

The final method involves the introduction of primers using a fluorescently labelled bead. Here each target has numerous corresponding beads. These beads all have a unique fluorescent profile that associated that bead with the target, and these beads are used to deliver part (or all) of a primer set unique to that target (any remaining fraction of the primer set may be ubiquitously present in all droplets but will be unable to amplify. The probe associated with all targets is a single color that does not overlap with any fluorescent profiles. As a result, a droplet containing a given target and its associated bead will fluoresce the probe color (indicating amplification) while the bead fluorescence indicates the target present and responsible for the amplification.

An Exemplary Protocol is as Follows:

1. The target(s), beads (containing part or all of a given primer set and probe), any remaining primer set/probe that will not amplify alone, and reagents (appropriate for amplification LAMP, PCR, RT-PCR, etc) are encapsulated in droplets via any number of methods (microfluidic, shaken emulsification, particle template emulsification, etc). For example, all target probes (HIV, COVID, influenza) consist of a constant (single or unique mixture) of fluorescence and are quenched unless amplification with that probe occurs. All probes are also uniformly present in all droplets (for example: 100% blue/DAPI). Each bead has a unique fluorescence signature (for example: COVID 0% green/FAM, 100% red/Cy5; HIV 100% green/FAM, 0% red/Cy5; influenza 50% green/FAM, 50% red/Cy5) along with the corresponding primers for amplification.

Preferably, the target encapsulation is performed such that up to one target per droplet is encapsulated. Similarly, bead encapsulation also occurs such that up to one target is present in each drop.

2. Once emulsification has occurred, droplets are processed according to the amplification reaction (isothermal Application Data Sheet are incorporated herein by reference, in their entirety. Aspects of the embodiments can be modified if necessary to employ concepts of the various patents, applications, and publications to provide yet further embodiments.

These and other changes can be made to the embodiments in light of the above-detailed description. In general, in the following claims, the terms used should not be construed to limit the claims to the specific embodiments disclosed in the specification and the claims but should be construed to include all possible embodiments along with the full scope of equivalents to which such claims are entitled. Accordingly, the claims are not limited by the disclosure.

---

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1
aacacaagct ttcggcagac                                        20

<210> SEQ ID NO 2
<211> LENGTH: 20
<212> TYPE: DNA
<213> ORGANISM: Artificial Sequence
<220> FEATURE:
<223> OTHER INFORMATION: synthetic

<400> SEQUENCE: 2
cccgaaggtg tgacttccat                                        20
```

--- for LAMP, thermocyclying for PCR/RT-PCR). These reactions proceed within the droplet.

3. Evaluation of the results occurs optically, evaluating the fluorescent profile of the droplets. In the case of positive amplification the droplet will fluoresce according to the probe signal (in this example 100% blue/DAPI. For such droplets (probe positive), the fluorescent signature of the bead will be determined. The bead signature will determine which target was amplified in the droplet. An analysis of the number of droplets will determine the concentration of the targets within the sample.

Figure 23:
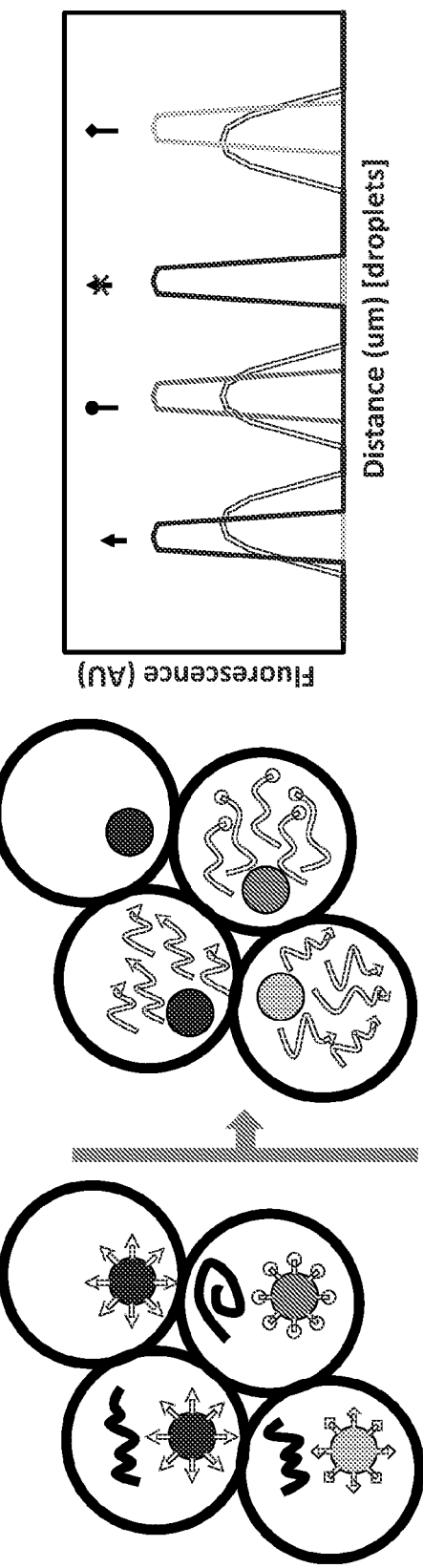
FIG. 23 shows the multiplex detection and quantification of target presence by counting droplets based on the fluorescent bead they carry and the presence or absence of fluorescence from target nucleic acid amplification.

FIG. 23 shows the multiplex detection and quantification of target presence by counting droplets based on the fluorescent bead they carry and the presence or absence of fluorescence from target nucleic acid amplification. Here primer sets are introduced into the droplet/reaction using beads. These beads possess a fluorescent profile unique to their primer target. In the presence of the correct target, the primers will react producing a positive fluorescence droplet. Positive droplets can then be identified by droplet fluorescence (binary) with the corresponding target identified by the bead fluorescence.

The various embodiments described above can be combined to provide further embodiments. All U.S. patents, U.S. patent application publications, U.S. patent application, foreign patents, foreign patent application and non-patent publications referred to in this specification and/or listed in the

What is claimed is:

1. A method of detecting a target nucleic acid in a sample from a patient collected at a point of care comprising:
   (a) combining in a vessel (i) a sample comprising a target nucleic acid; (ii) a solution comprising reagents for amplifying and detecting the target nucleic acid; and (iii) an immiscible carrier, thereby forming a combined solution;
   (b) agitating the combined solution of (a) under conditions that allow encapsulation of the target nucleic acid with the reagents for amplifying and detecting the target nucleic acid in multiple individual droplets, thereby forming a polydispersed emulsion;
   (c) incubating the polydispersed emulsion of step (b) under conditions that allow amplification of the target nucleic acid in the multiple individual droplets; and
   (d) detecting the target nucleic acid in the polydispersed emulsion;
   wherein steps (a)-(d) occur at the point of care, and
   wherein the detecting comprises simultaneously quantifying detection signals from (I) multiple layers of the multiple individual droplets and (II) a monolayer of the multiple individual droplets, and
   wherein the detecting occurs in a dual-height 2-d chamber.

2. The method according to claim 1, wherein the method does steps de not use a microwell, microdroplet array or microfluidic device.

3. The method according to claim 1, wherein the sample comprising the target nucleic acid has not undergone purification steps prior to combining in the vessel of step (a).

4. The method according to claim 1, wherein the detecting comprises quantifying a detection signal comprising a quantitation assay selected from the group consisting of sequencing, fluorescent signal reading, and turbidity reading.

5. The method according to claim 1, wherein the target nucleic acid is present in the sample at 1 to 50 copies.

6. The method according to claim 1, wherein the agitating comprises mixing the reagents by pipetting, shaking by hand, stirring, beating, bubbling, vortexing and sonicating.

7. The method according to claim 1, wherein the sample comprising the target nucleic acid is a sample obtained from a human subject.

8. The method according to claim 7, wherein the sample is a saliva sample, blood sample, urine sample, or tissue sample.

9. The method according to claim 1, wherein the target nucleic acid is from a virus, a bacteria, or a parasite.

10. The method according to claim 9, wherein the target nucleic acid is coronavirus, SARS-COV-2, human immunodeficiency virus (HIV), herpes simplex virus (HSV), human papilloma virus (HPV), influenza virus, or respiratory syncytial virus (RSV).

11. The method according to claim 1, wherein the target nucleic acid is amplified by PCR, RT-PCR, qPCR, digital droplet PCR (ddPCR), LAMP, or NASBA.

12. A method of detecting a target nucleic acid in a sample from a patient comprising:

(a) combining in a vessel (i) a sample comprising a target nucleic acid; (ii) a solution comprising reagents for amplifying and detecting the target nucleic acid; and (iii) an immiscible carrier, thereby forming a combined solution;

(b) agitating the combined solution of (a) under conditions that allow encapsulation of the target nucleic acid with the reagents for amplifying and detecting the target nucleic acid in multiple individual droplets, thereby forming a polydispersed emulsion;

(c) incubating the polydispersed emulsion of step (b) under conditions that allow amplification of the target nucleic acid in the multiple individual droplets; and (d) detecting the target nucleic acid in the polydispersed emulsion;

wherein the detecting comprises simultaneously quantifying detection signals from (I) multiple layers of the multiple individual droplets and (II) a monolayer of the multiple individual droplets, and wherein the detecting occurs in a dual-height 2-d chamber.

* * * * *